United States Patent
Vasavada et al.

(10) Patent No.: US 11,662,692 B2
(45) Date of Patent: May 30, 2023

(54) ELECTRONIC DEVICES AND SYSTEMS

(71) Applicant: META PLATFORMS TECHNOLOGIES, LLC, Menlo Park, CA (US)

(72) Inventors: Pranav Vasavada, San Ramon, CA (US); Derek William Wright, San Francisco, CA (US); Timothy Lowe, Newark, CA (US); Joseph Moak, San Carlos, CA (US); Peter Wesley Bristol, Seattle, WA (US); Nishant Srinivasan, San Francisco, CA (US); Chunli Chen, Seattle, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 0 days.

(21) Appl. No.: 17/544,610

(22) Filed: Dec. 7, 2021

(65) Prior Publication Data
US 2022/0091564 A1   Mar. 24, 2022

Related U.S. Application Data

(63) Continuation of application No. 17/210,547, filed on Mar. 24, 2021.
(Continued)

(51) Int. Cl.
*G04B 37/14*   (2006.01)
*A44C 5/14*   (2006.01)
(Continued)

(52) U.S. Cl.
CPC ........ *G04B 37/1486* (2013.01); *A44C 5/0007* (2013.01); *A44C 5/147* (2013.01);
(Continued)

(58) Field of Classification Search
CPC ............. G04B 37/1486; A44C 5/0007; A44C 5/147; A61B 5/4519; A61B 5/681; A61B 2562/16; G04G 21/025
(Continued)

(56) References Cited

U.S. PATENT DOCUMENTS 6,619,835 B2   9/2003  Kita
8,725,842 B1 *  5/2014  Al-Nasser ............. G04G 17/08
                                               709/219
(Continued)

FOREIGN PATENT DOCUMENTS

CN    206282085 U    6/2017
EP    2733579 A2    5/2014

OTHER PUBLICATIONS

International Search report and Written Opinion for International Application No. PCT/US2021/029002, dated Sep. 23, 2021, 17 pages.
Invitation to Pay AdditionalFees received for International Application No. PCT/US2021/029002, dated Aug. 2, 2021, 12 pages.

*Primary Examiner* — Edwin A. Leon
(74) *Attorney, Agent, or Firm* — Greenberg Traurig, LLP

(57) ABSTRACT

Systems may include a watch band, a watch body including at least one image sensor configured to capture a wide-angle image, a coupling mechanism configured to detachably couple the watch body to the watch band, and at least one biometric sensor on at least one of the watch band or the watch body. Various other related methods and systems.

21 Claims, 22 Drawing Sheets

Related U.S. Application Data

(60) Provisional application No. 63/056,345, filed on Jul. 24, 2020, provisional application No. 63/015,410, filed on Apr. 24, 2020.

(51) Int. Cl.
*A44C 5/00* (2006.01)
*A61B 5/00* (2006.01)
*G04G 21/02* (2010.01)

(52) U.S. Cl.
CPC ............ *A61B 5/4519* (2013.01); *A61B 5/681* (2013.01); *G04G 21/025* (2013.01); *A61B 2562/16* (2013.01)

(58) Field of Classification Search
USPC ........................................................ 368/282
See application file for complete search history.

(56) References Cited

U.S. PATENT DOCUMENTS

| | | | |
|---|---|---|---|
| 9,318,907 B2* | 4/2016 | Huang | G06F 1/1613 |
| 9,563,234 B2 | 2/2017 | Popalis et al. | |
| 10,129,503 B1 | 11/2018 | Kim et al. | |
| 10,866,619 B1 | 12/2020 | Bushnell et al. | |
| 10,878,959 B1 | 12/2020 | Reykhert | |
| 11,181,863 B2 | 11/2021 | Ely et al. | |
| 11,194,298 B2 | 12/2021 | Roach et al. | |
| 11,347,189 B1 | 5/2022 | Herrera et al. | |
| 2015/0131216 A1* | 5/2015 | Huang | G06F 3/014 |
| | | | 361/679.03 |
| 2015/0309535 A1 | 10/2015 | Connor | |
| 2016/0070234 A1* | 3/2016 | Lee | G06F 1/163 |
| | | | 368/282 |
| 2017/0237459 A1 | 8/2017 | Kim et al. | |
| 2018/0348815 A1 | 12/2018 | Popalis et al. | |
| 2020/0111260 A1 | 4/2020 | Osborn et al. | |
| 2021/0333759 A1 | 10/2021 | Vasavada et al. | |

* cited by examiner

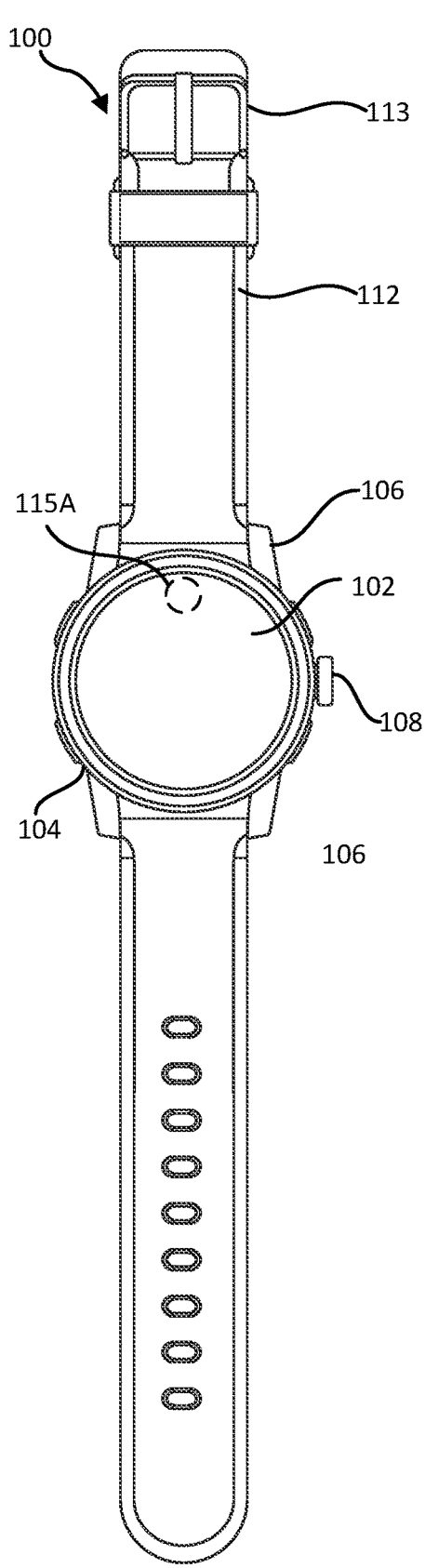
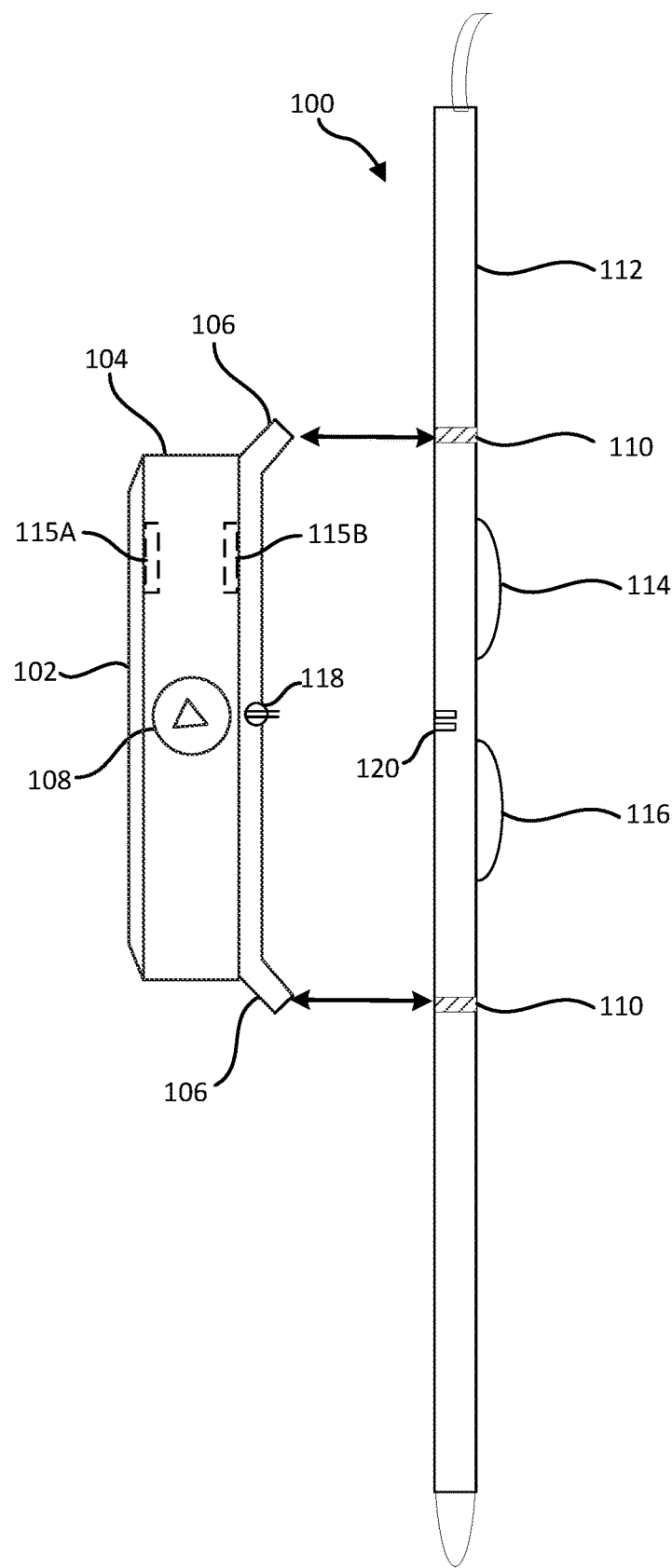
FIG. 1A
FIG. 1B

1500

```
┌─────────────────────────────────────────────┐
│ Determine at least one computing task of a  │
│ head-mounted display (HMD) that is suitable │
│ for processing on available computing       │
│ resources of a watch body                   │
│ 1510                                        │
└─────────────────────────────────────────────┘
                     │
                     ▼
┌─────────────────────────────────────────────┐
│ Selectively offload the at least one        │
│ computing task of the HMD that is suitable  │
│ for processing on the available computing   │
│ resources of the watch body to the watch    │
│ body                                        │
│ 1520                                        │
└─────────────────────────────────────────────┘
                     │
                     ▼
┌─────────────────────────────────────────────┐
│ Process, by the available computing         │
│ resources of the watch body, the at least   │
│ one computing task                          │
│ 1530                                        │
└─────────────────────────────────────────────┘
                     │
                     ▼
┌─────────────────────────────────────────────┐
│ Send results of the processed at least one  │
│ computing task to the HMD                   │
│ 1540                                        │
└─────────────────────────────────────────────┘
```

*FIG. 15*

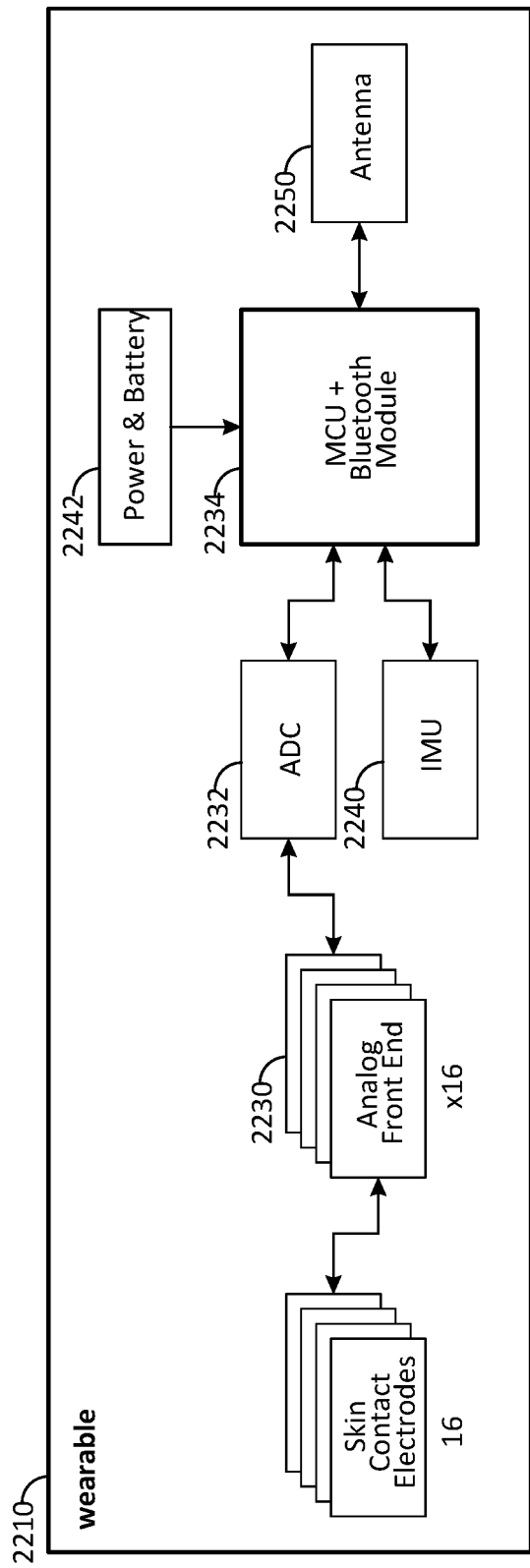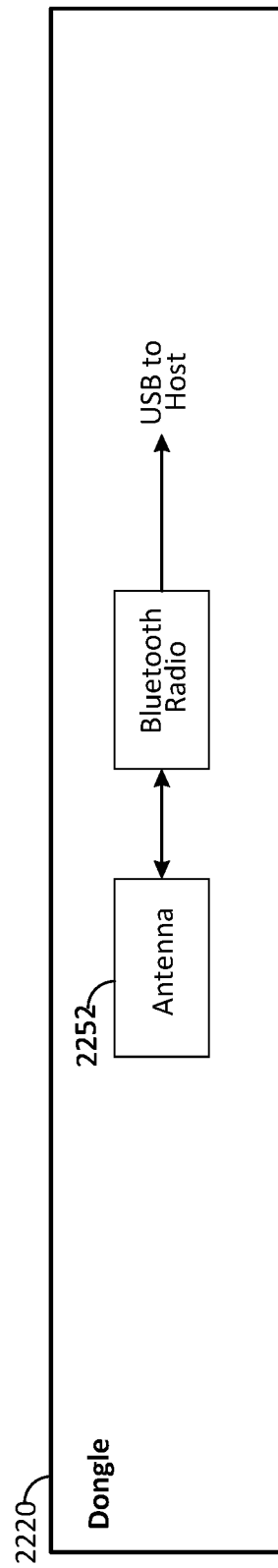
FIG. 22A
FIG. 22B

ELECTRONIC DEVICES AND SYSTEMS

CROSS REFERENCE TO RELATED APPLICATIONS

This application is a continuation of U.S. Non-Provisional patent application Ser. No. 17/210,547, titled "ELECTRONIC SYSTEM AND RELATED DEVICES AND METHODS," filed Mar. 24, 2021, which claims the benefit of U.S. Provisional Patent Application No. 63/015,410, titled "SPLIT ARCHITECTURE FOR A WRISTBAND SYSTEM AND RELATED DEVICES AND METHODS," filed on Apr. 24, 2020, and U.S. Provisional Patent Application No. 63/056,345, titled "SPLIT ARCHITECTURE FOR A WRISTBAND SYSTEM AND RELATED DEVICES AND METHODS," filed on Jul. 24, 2020, the disclosure of each of which is incorporated, in its entirety, by this reference.

BRIEF DESCRIPTION OF THE DRAWINGS

The accompanying drawings illustrate a number of example embodiments and are a part of the specification. Together with the following description, these drawings demonstrate and explain various principles of the present disclosure.

FIG. 1A is a plan view of an example wristband system, according to at least one embodiment of the present disclosure.

FIG. 1B is a side view of the example wristband system of FIG. 1A, according to at least one embodiment of the present disclosure.

FIG. 15 is a flow diagram illustrating an example method of decoupling a watch body from a watch band, according to at least one embodiment of the present disclosure.

FIGS. 22A and 22B are illustrations of an exemplary schematic diagram illustrating internal components of a wearable system.

Figure 2A:
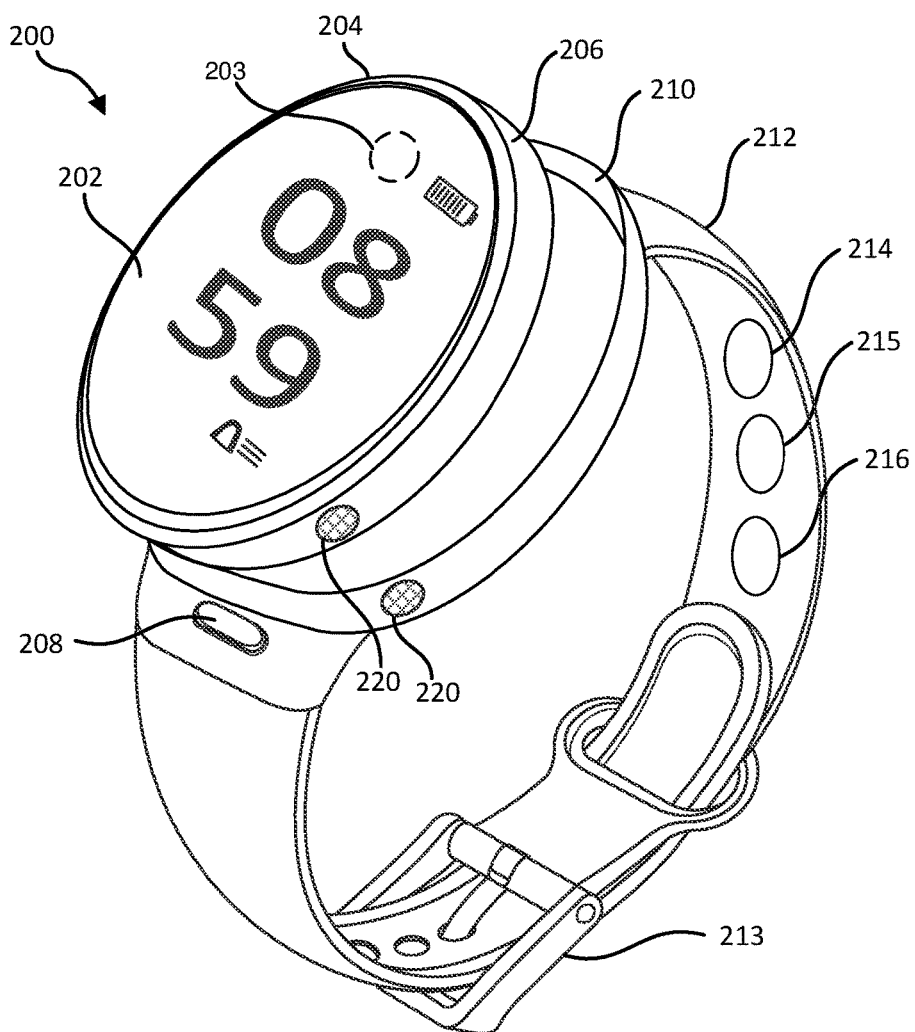
FIG. 2A is a perspective view of an example wristband system, according to at least one embodiment of the present disclosure.

Throughout the drawings, identical reference characters and descriptions indicate similar, but not necessarily identical, elements. While the example embodiments described herein are susceptible to various modifications and alternative forms, specific embodiments have been shown by way of example in the drawings and will be described in detail herein. However, the example embodiments described herein are not intended to be limited to the particular forms disclosed. Rather, the present disclosure covers all modifications, equivalents, and alternatives falling within the scope of the appended claims.

DETAILED DESCRIPTION OF EXAMPLE EMBODIMENTS

Wearable devices may be configured to be worn on a user's body part, such as a user's wrist or arm. Such wearable devices may be configured to perform various functions. A wristband system may be an electronic device worn on a user's wrist that performs functions such as delivering content to the user, executing social media applications, executing artificial-reality applications, messaging, web browsing, sensing ambient conditions, interfacing with head-mounted displays, monitoring the health status associated with the user, etc. However, since wearable devices are typically worn on a body part of a user, a wristband system may present an encumbrance to the user, such as when the user is sleeping or engaged in a sporting activity.

The present disclosure details systems, devices, and methods related to a wristband system that includes a watch band that detachably couples to a watch body. The watch body may include a coupling mechanism for electrically and mechanically coupling the watch body to the watch band. The wristband system may have a split architecture that allows the watch band and the watch body to operate both independently and in communication with one another. The mechanical architecture may include a coupling mechanism on the watch band and/or the watch body that allows a user to conveniently attach and detach the watch body from the watch band. Advantages of the present disclosure may include reducing an encumbrance to a user donning the watch band when the watch body is decoupled from the watch band as compared to when the watch body is coupled to the watch band. Advantages of the present disclosure may also include reducing an overall power consumption and extending battery charge time of the wristband system by enabling each of the watch body and watch band to have independent power consumption modes.

The wristband system may be used in conjunction with an artificial-reality (AR) system. Sensors of the wristband system (e.g., image sensors, inertial measurement unit (IMU), etc.) may be used to enhance an AR application running on the AR system. Further, the watch band may include sensors that measure biometrics of the user. For example, the watch band may include neuromuscular sensors (e.g., neuromuscular sensors 2110 of FIG. 21A) disposed on an inside surface of the watch band contacting the user that detects the muscle intentions of the user. The AR system may include a head-mounted display that is configured to enhance a user interaction with an object within the AR environment based on the muscle intentions of the user. Signals sensed by the neuromuscular sensors may be processed and used to provide a user with an enhanced interaction with a physical object and/or a virtual object in an AR environment. For example, the AR system may operate in conjunction with the neuromuscular sensors to overlay one or more visual indicators on or near an object within the AR environment such that the user could perform "enhanced" or "augmented" interactions with the object.

In some examples, the wristband system may have sufficient processing capabilities (e.g., CPU, memory, bandwidth, battery power, etc.) to offload computing tasks from a head-mounted display (HMD) to the wristband system. Methods of the present disclosure may determine a computing task of the HMD that is suitable for processing on available computing resources of the watch body. The computing task to be offloaded may be determined based on computing requirements, power consumption, battery charge level, latency requirements, or a combination thereof. The tasks offloaded to the watch body may include processing images captured by image sensors of the HMD, a location determining task, a neural network training task, etc. The watch body may process the computing task and return the results to the HMD. In some examples, offloading computing tasks from the HMD to the wristband system may reduce heat generation, reduce power consumption and/or decrease computing task execution latency in the HMD.

In some examples, a head-mounted display (HMD) may have sufficient processing capabilities (e.g., central processing unit (CPU), memory, bandwidth, battery power, etc.) to offload computing tasks from the wristband system (e.g., a watch body, a watch band) to the HMD. Methods of the present disclosure may include determining a computing task of the wristband system that is suitable for processing on available computing resources of the HMD. By way of example, the computing task to be offloaded may be determined based on computing requirements, power consumption, battery charge level, latency requirements, or a combination thereof. The tasks offloaded to the HMD may include processing images captured by image sensors of the wristband system, a location determining task, a neural network training task, etc. The HMD may process the computing task(s) and return the results to the wristband system. In some examples, offloading computing tasks from the wristband system to the HMD may reduce heat generation, reduce power consumption and/or decrease computing task execution latency in the wristband system.

In some examples, the wristband system may include multiple electronic devices including, without limitation, a smartphone, a server, a HMD, a laptop computer, a desktop computer, a gaming system, Internet of things devices, etc. Such electronic devices may communicate with the wristband system (e.g., via a personal area network). The wristband system may have sufficient processing capabilities (e.g., CPU, memory, bandwidth, battery power, etc.) to offload computing tasks from each of the multiple electronic devices to the wristband system. Additionally or alternatively, each of the multiple electronic devices may have sufficient processing capabilities (e.g., CPU, memory, bandwidth, battery power, etc.) to offload computing tasks from the wristband system to the electronic device(s).

The following will provide, with reference to FIGS. 1-22B, detailed descriptions of a split architecture for a wristband system including related devices and methods. First, a description of a wristband system including a watch band, a watch body, and a method of decoupling the watch body from the watch band is presented in reference to FIGS. 1A and 1B. A description of integrating neuromuscular sensors of the watch body with an AR system is presented in reference to FIGS. 2A, 2B, and 2C. An example block diagram of a split architecture for a wristband system is presented in reference to FIG. 3. Various types of mechanisms for detachably coupling a watch body to a watch band are presented in reference to FIGS. 4-14. A method of selectively offloading a computing task of a head-mounted display to a watch body is presented in reference to FIG. 9. Various types of example artificial-reality devices that may be used in conjunction with a wristband system are presented in reference to FIGS. 16-22B.

FIG. 1A illustrates an example wristband system 100 that includes a watch body 104 coupled to a watch band 112. Watch body 104 and watch band 112 may have any size and/or shape that is configured to allow a user to wear wristband system 100 on a body part (e.g., a wrist). Wristband system 100 may include a retaining mechanism 113 (e.g., a buckle) for securing watch band 112 to the user's wrist. Wristband system 100 may also include a coupling mechanism 106, 110 for detachably coupling watch body 104 to watch band 112. Wristband system 100 may perform various functions associated with the user. The functions may be executed independently in watch body 104, independently in watch band 112, and/or in communication between watch body 104 and watch band 112. Watch band 112 may be configured to operate independently (e.g., execute functions independently) from watch body 104. Additionally or alternatively, watch body 104 may be configured to operate independently (e.g., execute functions independently) from watch band 112. As will be described in more detail below with reference to the block diagram of FIG. 3, watch band 112 and/or watch body 104 may each include the independent resources required to independently execute functions. For example, watch band 112 and/or watch body 104 may each include a power source (e.g., a battery), a memory, data storage, a processor (e.g., a CPU), communications, a light source (e.g., at least one infrared LED for tracking watch body 104 and/or watch band 112 in space with an external sensor), and/or input/output devices.

As will be described in more detail below with reference to FIG. 3, functions that may be independently executed by watch body 104, by watch band 112, or by wristband system 100 may include, without limitation, display of visual content to the user (e.g., visual content displayed on display screen 102), sensing user input (e.g., sensing a touch on button 108, sensing biometric data with sensor 114, sensing neuromuscular signals with sensor 115, etc.), messaging (e.g., text, speech, video, etc.), image capture (e.g., with a front-facing image sensor 115A and/or a rear-facing image sensor 115B), wireless communications (e.g., cellular, near field, WiFi, personal area network, etc.), location determination, financial transactions, providing haptic feedback, etc. Functions may be independently executed by watch body 104, by watch band 112, or on wristband system 100 in conjunction with an artificial-reality system such as the artificial-reality systems described in FIGS. 16-22B. In some examples, wristband system 100 may include vibrotactile system 1800 of FIG. 18, haptic device 2030 of FIG. 20, and/or neuromuscular sensors 2110 of FIG. 21A.

In some examples, display screen 102 may display visual content to the user. In some examples, watch body 104 may determine an orientation of display screen 102 of watch body 104 relative to an eye gaze direction of a user and may orient content viewed on display screen 102 to the eye gaze direction of the user. The displayed visual content may be oriented to the eye gaze of the user such that the content is easily viewed by the user without user intervention. Traditional displays on wristband systems may orient the visual content in a static manner such that when a user moves or rotates the wristband system, the content may remain in the same position relative to the watch band system causing difficulty for the user to view the content.

Embodiments of the present disclosure may orient (e.g., rotate, flip, stretch, etc.) the displayed content such that the displayed content remains in substantially the same orientation relative to the eye gaze of the user (e.g., the direction in which the user is looking). The displayed visual content may also be modified based on the eye gaze of the user without user intervention. For example, in order to reduce the power consumption of wristband system 100, display screen 102 may dim the brightness of the displayed content, pause the displaying of video content, or power down display screen 102 when it is determined that the user is not looking at display screen 102. In some examples, a sensor(s) of wristband system 100 may determine an orientation of display screen 102 relative to an eye gaze direction of the user.

Embodiments of the present disclosure may measure the position, orientation, and/or motion of eyes of the user in a variety of ways, including through the use of optical-based eye-tracking techniques, ultrasound-based eye-tracking techniques, etc. For example, front-facing image sensor 115A and/or rear-facing image sensor 115B may capture images of the user's eyes and determine the eye gaze direction based on processing of the captured images. The captured images may be processed using CPU 326, microcontroller unit 352 (see FIG. 3), a processor in communication with wristband system 100 (e.g., a processor of a head-mounted display (HMD)), or a combination thereof.

In some examples, sensors other than sensors of wristband system 100 may be used to determine the user's eye gaze direction. For example, an eye-tracking subsystem of an HMD (e.g., augmented-reality system 1600 of FIG. 16, virtual-reality system 1700 of FIG. 17, head-mounted display 1902 of FIG. 19, or augmented-reality glasses 2020 in FIG. 20) in communication with wristband system 100 may include a variety of different sensors, such as two-dimensional (2D) or three-dimensional (3D) cameras, time-of-flight depth sensors, single-beam or sweeping laser rangefinders, 3D LiDAR sensors, that may be used to determine and track the eye gaze of the user. In this example, a processing subsystem may process data from one or more of these sensors to measure, detect, determine, and/or otherwise monitor the position, orientation, and/or motion of the user's eye(s). Display screen 102 may receive the eye tracking information from the HMD, CPU 326, microcontroller unit 352, or a combination thereof, and orient the displayed content based on the user's eye gaze direction.

Figure 16:
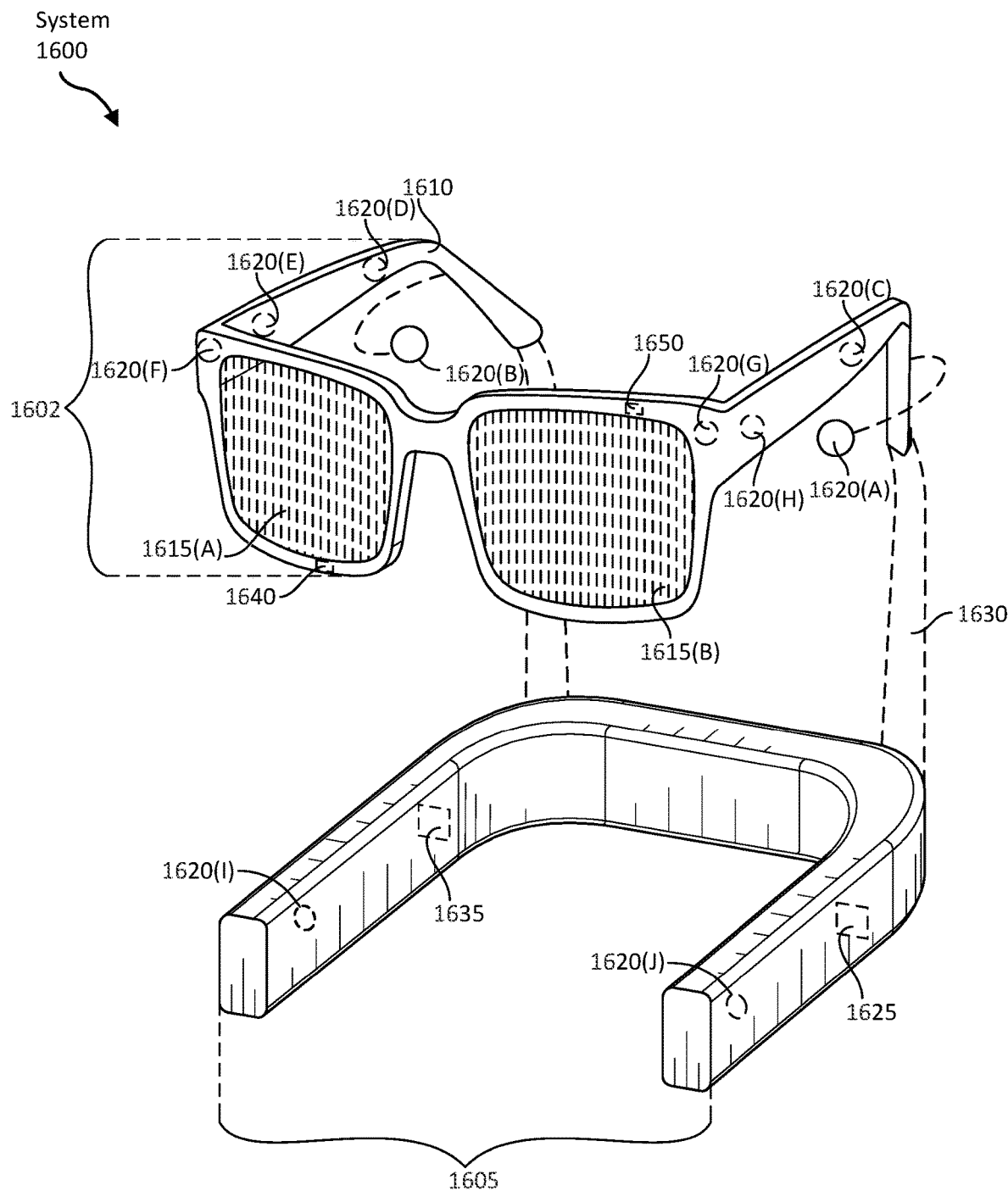
FIG. 16 is an illustration of exemplary augmented-reality glasses that may be used in connection with embodiments of this disclosure.
Figure 17:
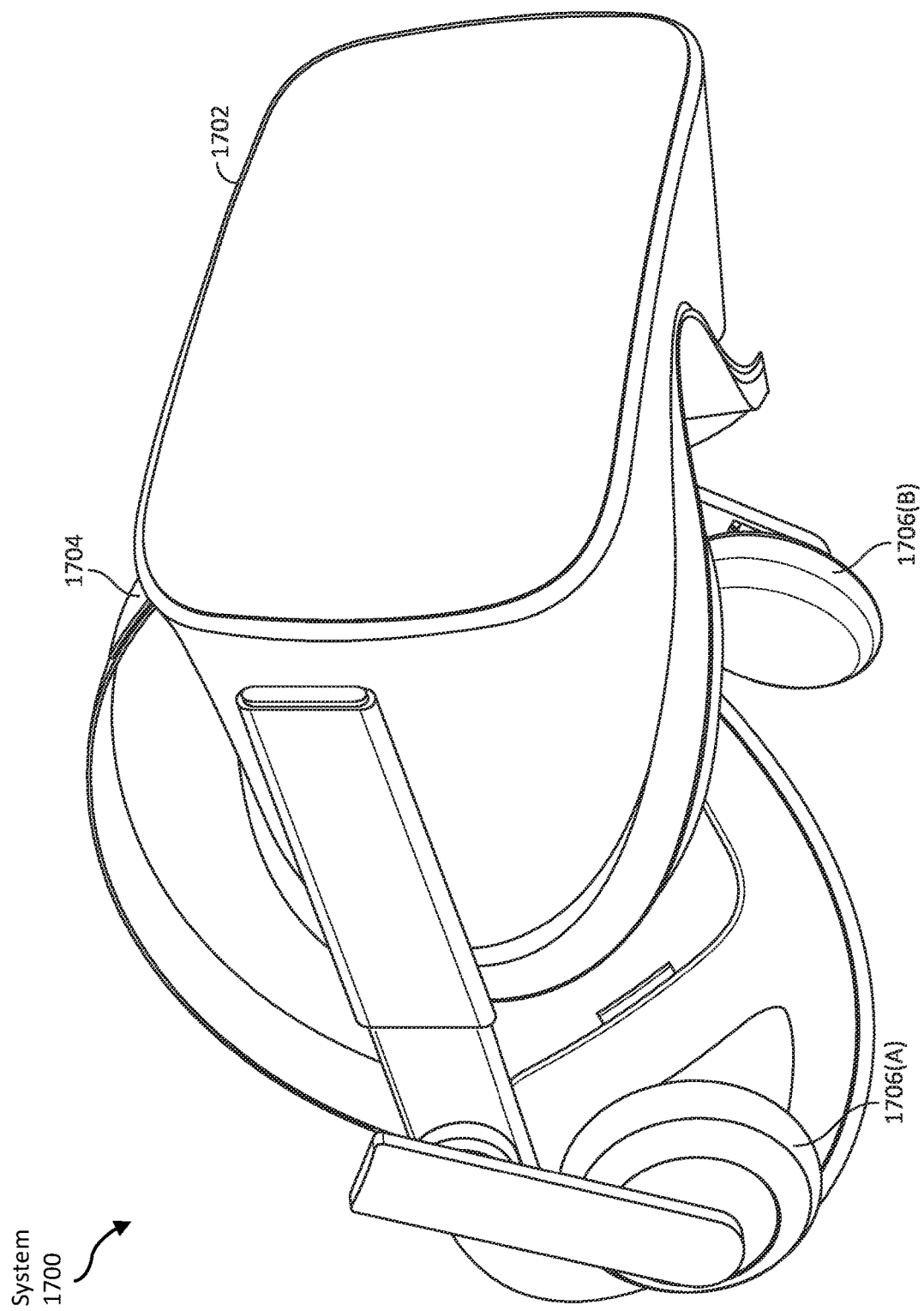
FIG. 17 is an illustration of an exemplary virtual-reality headset that may be used in connection with embodiments of this disclosure.
Figure 19:
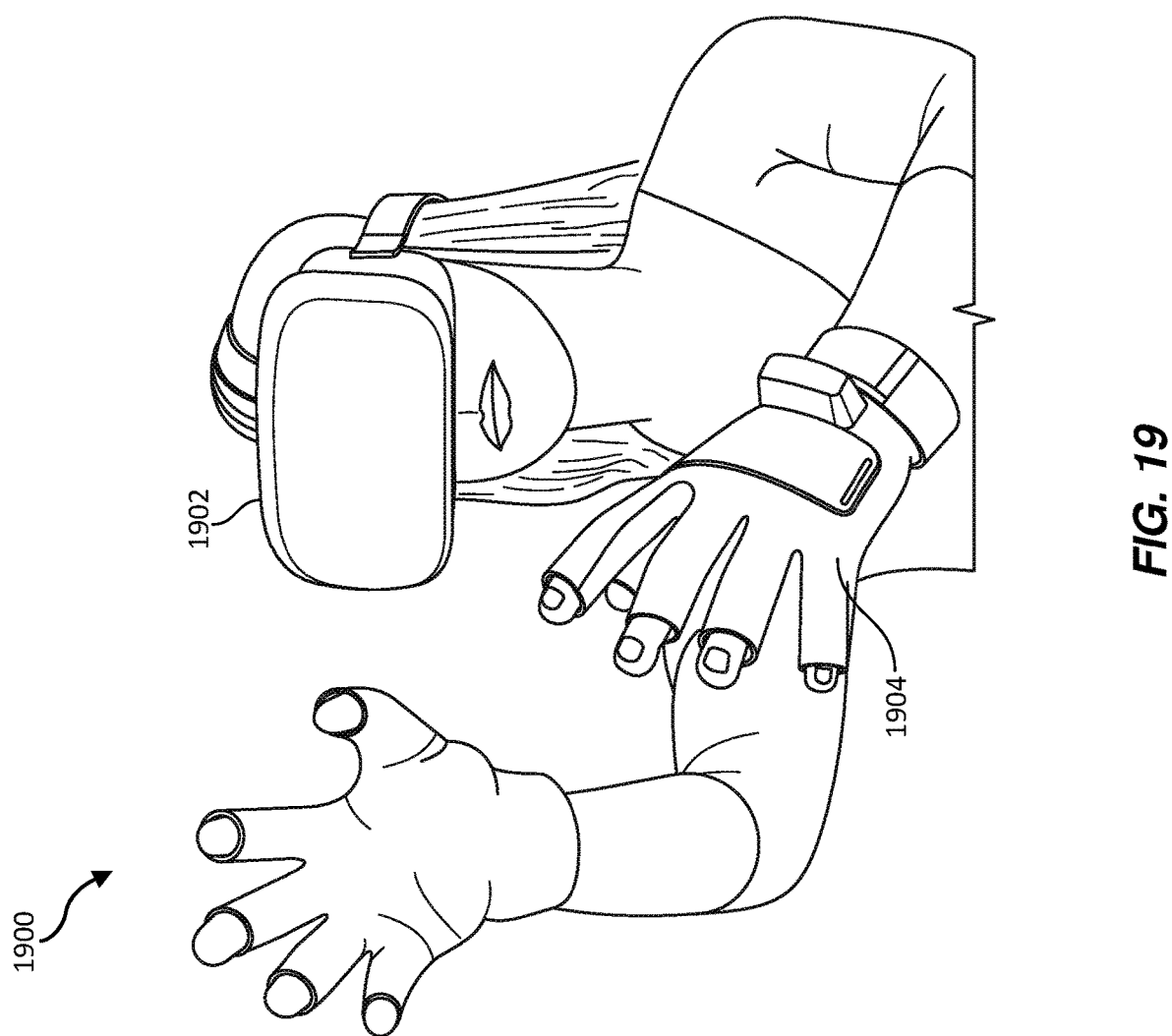
FIG. 19 is an illustration of an exemplary virtual-reality environment according to embodiments of this disclosure.
Figure 20:
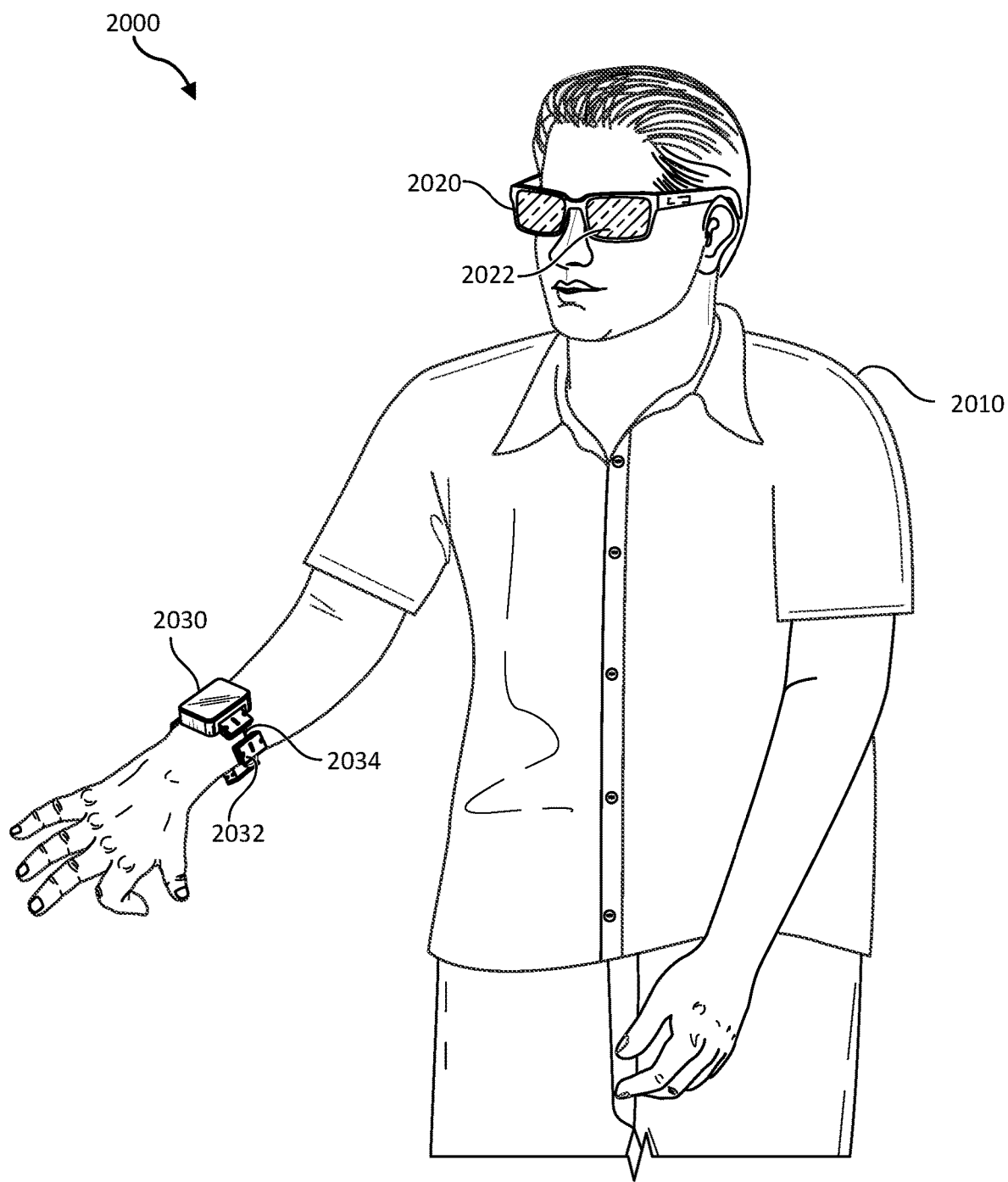
FIG. 20 is an illustration of an exemplary augmented-reality environment according to embodiments of this disclosure.

In some examples, watch body 104 may be communicatively coupled to an HMD (e.g., augmented-reality system 1600 of FIG. 16, virtual-reality system 1700 of FIG. 17, head-mounted display 1902 of FIG. 19, or augmented-reality glasses 2020 in FIG. 20). Front-facing image sensor 115A and/or rear-facing image sensor 115B may capture wide-angle images of the area surrounding front-facing image sensor 115A and/or rear-facing image sensor 115B such as hemispherical images (e.g., at least hemispherical, substantially spherical, etc.), 180-degree images, 360-degree area images, panoramic images, ultra-wide area images, or a combination thereof. In some examples, front-facing image sensor 115A and/or rear-facing image sensor 115B may be configured to capture images having a range between 45 degrees and 360 degrees. In some examples, watch body 104 may be communicatively coupled to the HMD and the HMD may be configured to display at least a portion of a captured image (e.g., a wide-angle image). The captured images may be communicated to the HMD and at least a portion of the captured images may be displayed to the user on the HMD. The images may be captured in 2D and/or 3D and displayed to the user in 2D and/or 3D. In some examples, the captured images may be displayed to the user in conjunction with an artificial-reality application. Images captured by front-facing image sensor 115A and/or rear-facing image sensor 115B may be processed before displaying on the HMD. For example, certain features and/or objects (e.g., people, faces, devices, backgrounds, etc.) of the captured image may be subtracted, added, and/or enhanced before displaying on the HMD.

FIG. 1B illustrates an example wristband system 100 that includes a watch body 104 decoupled from a watch band 112. Watch band 112 may be donned (e.g., worn) on a body part (e.g., a wrist) of a user and may operate independently from watch body 104. For example, watch band 112 may be configured to be worn by a user and an inner surface of watch band 112 may be in contact with the user's skin. When worn by a user, sensor 114 may be in contact with the user's skin. Sensor 114 may be a biosensor that senses a user's heart rate, bioimpedance, saturated oxygen level, temperature, sweat level, muscle intentions, steps taken, or a combination thereof. Watch band 112 may include multiple sensors 114 that may be distributed on an inside surface, in an interior volume, and/or on an outside surface of watch band 112. Sensor 114 may also include a sensor that provides data about a user's environment including a user's motion (e.g., an IMU), altitude, location, orientation, gait (e.g., a pedometer), or a combination thereof. Watch band 112 may transmit the data acquired by sensor 114 to watch body 104 using a wired communication method (e.g., a Universal Asynchronous Receiver Transmitter (UART), a Universal Serial Bus (USB) transceiver, etc.) and/or a wireless communication method (e.g., near field communication, Bluetooth™, etc.). In some examples, watch body 104 may include an electrical connector 118 that mates with connector 120 of watch band 112 for wired communication and/or power transfer. In some examples, watch body 104 and watch band 112 may include wireless communication devices such as those described with reference to FIG. 3 below.

Watch band 112 and/or watch body 104 may include a haptic device 116 (e.g., a vibratory haptic actuator) that is configured to provide haptic feedback (e.g., a cutaneous and/or kinesthetic sensation) to the user's skin. Watch band 112 and/or watch body 104 may include a haptic actuator that is configured to provide haptic feedback to a user based on at least one of instructions from watch body 104 or instructions from a head-mounted display of an artificial-reality system. Sensor 114 and/or haptic device 116 may be configured to operate in conjunction with multiple applications including, without limitation, health monitoring, social media, game playing, and artificial reality (e.g., the applications associated with artificial reality as described below with reference to FIGS. 16-22B). As described in detail below with reference to FIG. 2A, an electromyography sensor (e.g., neuromuscular sensor 2110 of FIG. 21A) integrated into watch band 112 and/or watch body 104 may sense a user's muscle intention. The sensed muscle intention may be transmitted to an artificial-reality system (e.g., the augmented-reality system 1600 in FIG. 16 or the virtual-reality system 1700 in FIG. 17) to perform an action in an associated artificial-reality environment, such as to control a physical and/or virtual object displayed to the user. Further, the artificial-reality system may provide haptic feedback to the user in coordination with the artificial reality application via haptic device 116.

Wristband system 100 may include a coupling mechanism for detachably coupling watch body 104 to watch band 112. A user may detach watch body 104 from watch band 112 in order to reduce the encumbrance of wristband system 100 to the user. Detaching watch body 104 from watch band 112 may reduce a physical profile and/or a weight of wristband system 100. Wristband system 100 may include a watch body coupling mechanism(s) 106 and/or a watch band coupling mechanism(s) 110. Any method or coupling mechanism may be used for detachably coupling watch body 104 to watch band 112. For example, the mechanisms described below with reference to FIGS. 4-14C may be used for detachably coupling watch body 104 to watch band 112. A user may perform any type of motion to couple watch body 104 to watch band 112 and to decouple watch body 104 from watch band 112. For example, a user may twist, slide, turn, push, pull, or rotate watch body 104 relative to watch band 112, or a combination thereof, to attach watch body 104 to watch band 112 and to detach watch body 104 from watch band 112.

Watch body coupling mechanism(s) 106 and/or watch band coupling mechanism(s) 110 may include any type of mechanism that allows a user to repeat cycles of coupling and decoupling of watch body 104 relative to watch band 112. Watch body coupling mechanism(s) 106 and/or watch band coupling mechanism(s) 110 may include, without limitation, a rotation-based connector, a shear-pin coupler, a retention spring, one or more magnets, a clip, a pin shaft, a hook and loop fastener, or a combination thereof.

As illustrated in FIG. 1B, in some examples, watch body 104 may include front-facing image sensor 115A and rear-facing image sensor 115B. Front-facing image sensor 115A may be located in a front face of watch body 104 and rear-facing image sensor 115B may be located in a rear face of watch body 104. In some examples, a level of functionality of at least one of watch band 112 or watch body 104 may be modified when watch body 104 is detached from watch band 112. The level of functionality that may be modified may include the functionality of front-facing image sensor 115A and/or rear-facing image sensor 115B. By way of example, a user may use front-facing image sensor 115A to capture an image (e.g., a still image or a video) of the user, for a so-called "selfie view," when watch body 104 is attached to or detached from watch band 112. When watch body 104 is detached from watch band 112, the user may use rear-facing image sensor 115B to capture an image (e.g., a still image or a video) of a scene or object away from the user, for a so-called "world view." Although FIG. 1B shows a single front-facing image sensor 115A and a single rear-facing image sensor 115B, the present disclosure is not so limited. Rather, watch body 104 may include multiple front-facing image sensors 115A and/or multiple rear-facing image sensors 115B. Additionally or alternatively, watch band 112 may include at least one front-facing image sensor 115A and at least one rear-facing image sensor 115B. Of course, the orientation at which the user holds watch body 104 may alter whether the image sensors 115A and 115B are respectively used for a selfie view or a world view.

In some examples, image sensors 115A and/or 115B may be oriented to capture a first wide-angle image in a first direction. In some examples, image sensors 115A and/or 115B may be oriented to capture a second wide-angle image in a second direction opposite the first direction. The system may be configured to stitch the first wide-angle image and the second wide-angle image together to create a combined image. In some embodiments, images from front-facing image sensor 115A and from rear-facing image sensor 115B may be stitched together (e.g., with a processor) to provide a single, wide-angle image (e.g., at least hemispherical, substantially spherical, a wide-angle view, etc.), a 180-degree image, 360-degree image, a panoramic image, an ultra-wide area image, an image within the range of 45 degrees and 360 degrees, or a combination thereof, surrounding watch body 104. In some embodiments, front-facing image sensor 115A may be a wide-angle image sensor that may alone be configured to capture at least a hemispherical view surrounding watch body 104. In some examples, when watch body 104 is attached to watch band 112, rear-facing image sensor 115B or a portion thereof (e.g., certain pixels thereof) may be used to optically sense biometric data of the user.

FIG. 2A illustrates a perspective view of an example wristband system 200 that includes a watch body 204 decoupled from a watch band 212. Wristband system 200 may be structured and/or function similarly to wristband system 100 of FIGS. 1A and 1B. Watch body 204 and watch band 212 may have a substantially rectangular or circular shape and may be configured to allow a user to wear wristband system 200 on a body part (e.g., a wrist). Wristband system 200 may include a retaining mechanism 213 (e.g., a buckle, a hook and loop fastener, etc.) for securing watch band 212 to the user's wrist. Wristband system 200 may also include a coupling mechanism 206 for detachably coupling watch body 204 to watch band 212 such as the mechanisms described below with reference to FIGS. 4-14C.

Wristband system 200 may perform various functions associated with the user as described above with reference to FIGS. 1A and 1B. As will be described in more detail with reference to FIG. 3, functions executed by wristband system 200 may include, without limitation, display of visual content to the user (e.g., visual content displayed on display screen 202), sensing user input (e.g., sensing a touch on button 208, sensing biometric data on sensor 214, sensing neuromuscular signals on neuromuscular sensor 215, etc.), messaging (e.g., text, speech, video, etc.), image capture (e.g., with a front-facing image sensor 203 and/or a rear-facing image sensor), wireless communications (e.g., cellular, near field, WiFi, personal area network, etc.), location determination, financial transactions, providing haptic feedback, alarms, notifications, biometric authentication, health monitoring, sleep monitoring, etc. These functions may be executed independently in watch body 204, independently in watch band 212, and/or in communication between watch body 204 and watch band 212. Functions may be executed on wristband system 200 in conjunction with an artificial-reality system such as the artificial-reality systems described in FIGS. 16-22B. In some examples, wristband system 200 may include vibrotactile system 1800 of FIG. 18 and/or haptic device 1930 of FIG. 19.

Watch band 212 may be configured to be worn by a user such that an inner surface of watch band 212 may be in contact with the user's skin. When worn by a user, sensor 214 may be in contact with the user's skin. Sensor 214 may be a biosensor that senses a user's heart rate, saturated oxygen level, temperature, sweat level, muscle intentions, or a combination thereof. Watch band 212 may include multiple sensors 214 that may be distributed on an inside and/or an outside surface of watch band 212. Additionally or alternatively, watch body 204 may include the same or different sensors than watch band 212. For example, multiple sensors may be distributed on an inside and/or an outside surface of watch body 204. As described below with reference to FIG. 3, watch body 204 may include, without limitation, front-facing image sensor 115A, rear-facing image sensor 115B, a biometric sensor, an IMU, a heart rate sensor, a saturated oxygen sensor, a neuromuscular sensor(s) (e.g., neuromuscular sensors 2110 of FIG. 21A), an altimeter sensor, a temperature sensor, a bioimpedance sensor, a pedometer sensor, an optical sensor, a touch sensor, a sweat sensor, etc. Sensor 214 may also include a sensor that provides data about a user's environment including a user's motion (e.g., an IMU), altitude, location, orientation, gait, or a combination thereof. Sensor 214 may also include a light sensor (e.g., an infrared light sensor, a visible light sensor) that is configured to track a position and/or motion of watch body 204 and/or watch band 212. Watch band 212 may transmit the data acquired by sensor 214 to watch body 204 using a wired communication method (e.g., a UART, a USB transceiver, etc.) and/or a wireless communication method (e.g., near field communication, Bluetooth™, etc.). Watch band 212 may be configured to operate (e.g., to collect data using sensor 214) independent of whether watch body 204 is coupled to or decoupled from watch band 212.

Watch band 212 and/or watch body 204 may include a haptic device 216 (e.g., a vibratory haptic actuator) that is configured to provide haptic feedback (e.g., a cutaneous and/or kinesthetic sensation, etc.) to the user's skin. Sensor 214 and/or haptic device 216 may be configured to operate in conjunction with multiple applications including, without limitation, health monitoring, social media, game playing, and artificial reality (e.g., the applications associated with artificial reality as described below with reference to FIGS. 16-22B).

In some examples, watch band 212 may include a neuromuscular sensor 215 (e.g., an electromyography (EMG) sensor, a mechanomyogram (MMG) sensor, a sonomyography (SMG) sensor, etc.). Neuromuscular sensor 215 may sense a user's muscle intention. Neuromuscular sensor 215 may include neuromuscular sensor 2110 of FIG. 21A. The sensed muscle intention may be transmitted to an artificial-reality (AR) system (e.g., augmented-reality system 1600 of FIG. 16, virtual-reality system 1700 of FIG. 17, head-mounted display 1902 of FIG. 19, or augmented-reality glasses 2020 in FIG. 20) to perform an action in an associated artificial-reality environment, such as to control the motion of a virtual device displayed to the user. Further, the artificial-reality system may provide haptic feedback to the user in coordination with the artificial-reality application via haptic device 216.

Signals from neuromuscular sensor 215 may be used to provide a user with an enhanced interaction with a physical object and/or a virtual object in an AR environment generated by an AR system (e.g., augmented-reality system 1600 of FIG. 16, virtual-reality system 1700 of FIG. 17, head-mounted display 1902 of FIG. 19, or augmented-reality glasses 2020 in FIG. 20). Signals from neuromuscular sensor 215 may be obtained (e.g., sensed and recorded) by one or more neuromuscular sensors 215 of watch band 212. Although FIG. 2A shows one neuromuscular sensor 215, watch band 212 may include a plurality of neuromuscular sensors 215 arranged circumferentially on an inside surface of watch band 212 such that the plurality of neuromuscular sensors 215 contact the skin of the user. Watch band 212 may include a plurality of neuromuscular sensors 215 arranged circumferentially on an inside surface of watch band 212 as shown in wearable system 2100 of FIG. 21A. Neuromuscular sensor 215 may sense and record neuromuscular signals from the user as the user performs muscular activations (e.g., movements, gestures, etc.). The muscular activations performed by the user may include static gestures, such as placing the user's hand palm down on a table; dynamic gestures, such as grasping a physical or virtual object; and covert gestures that are imperceptible to another person, such as slightly tensing a joint by co-contracting opposing muscles or using sub-muscular activations. The muscular activations performed by the user may include symbolic gestures (e.g., gestures mapped to other gestures, interactions, or commands, for example, based on a gesture vocabulary that specifies the mapping of gestures to commands).

An AR system (e.g., the AR systems of FIGS. 16-22B) may operate in conjunction with neuromuscular sensor 215 to overlay one or more visual indicators on or near a physical and/or virtual object within the AR environment. The visual indicators may instruct the user that the physical and/or virtual object (e.g., a sporting object, a gaming object) is an object that has a set of virtual controls associated with it such that, if the user interacted with the object (e.g., by picking it up), the user could perform one or more "enhanced" or "augmented" interactions with the object. The visual indicator(s) may indicate that it is an object capable of enhanced interaction.

In another example, an indication of a set of virtual controls for the physical or virtual object, which may be activated by the user to control the object, may be overlaid on or displayed near the object in the AR environment. The user may interact with the indicator(s) of the set of virtual controls by, for example, performing a muscular activation to select one of the virtual controls. Neuromuscular sensor 215 may sense the muscular activation and in response to the interaction of the user with the indicator(s) of the set of virtual controls, information relating to an interaction with the object may be determined. For example, if the object is a virtual sword (e.g., a sword used in an AR game), the user may perform a gesture to select the virtual sword's functionality, such that, when the user picks up the virtual sword, it may be used to play a game within the AR environment.

Information relating to an interaction of the user with the physical and/or virtual object may be determined based on the neuromuscular signals obtained by the neuromuscular sensor 215 and/or information derived from the neuromuscular signals (e.g., information based on analog and/or digital processing of the neuromuscular signals). Additionally or alternatively, auxiliary signals from one or more auxiliary device(s) (e.g., front-facing image sensor 115A, rear-facing image sensor 115B, IMU 342, microphone 308, heart rate sensor 358, image sensors of the AR systems of FIGS. 16-22B, etc.) may supplement the neuromuscular signals to determine the information relating to the interaction of the user with the physical and/or virtual object. For example, neuromuscular sensor 215 may determine how tightly the user is grasping the physical and/or virtual object, and a control signal may be sent to the AR system based on an amount of grasping force being applied to the physical object. Continuing with the example above, the object may be a virtual sword, and applying different amounts of grasping and/or swinging force to the virtual sword (e.g., using data gathered by the IMU 342) may change (e.g., enhance) the functionality of the virtual sword while interacting with a virtual game in the AR environment.

Wristband system 200 may include a coupling mechanism for detachably coupling watch body 204 to watch band 212. A user may detach watch body 204 from watch band 212 in order to reduce the encumbrance of wristband system 200 to the user. Wristband system 200 may include a watch body coupling mechanism(s) 206 and/or watch band coupling mechanism(s) 210 (e.g., a cradle, a tracker band, a support base, a clasp). Any method or coupling mechanism may be used for detachably coupling watch body 204 to watch band 212 such as the mechanism described with reference to FIGS. 4-14C. A user may perform any type of motion to couple watch body 204 to watch band 212 and to decouple watch body 204 from watch band 212. For example, a user may twist, slide, turn, push, pull, or rotate watch body 204 relative to watch band 212, or a combination thereof, to attach watch body 204 to watch band 212 and to detach watch body 204 from watch band 212.

As shown in the example of FIG. 2A, watch band coupling mechanism 210 may include a type of frame or shell that allows watch body coupling mechanism 206 to be retained within watch band coupling mechanism 210. Watch body 204 may be detachably coupled to watch band 212 through a friction fit, magnetic coupling, a rotation-based connector, a shear-pin coupler, a retention spring, one or more magnets, a clip, a pin shaft, a hook and loop fastener, or a combination thereof. In some examples, watch body 204 may be decoupled from watch band 212 by actuation of release mechanism 220. Release mechanism 220 may include, without limitation, a button, a knob, a plunger, a handle, a lever, a fastener, a clasp, a dial, a latch, or a combination thereof.

Figure 4:
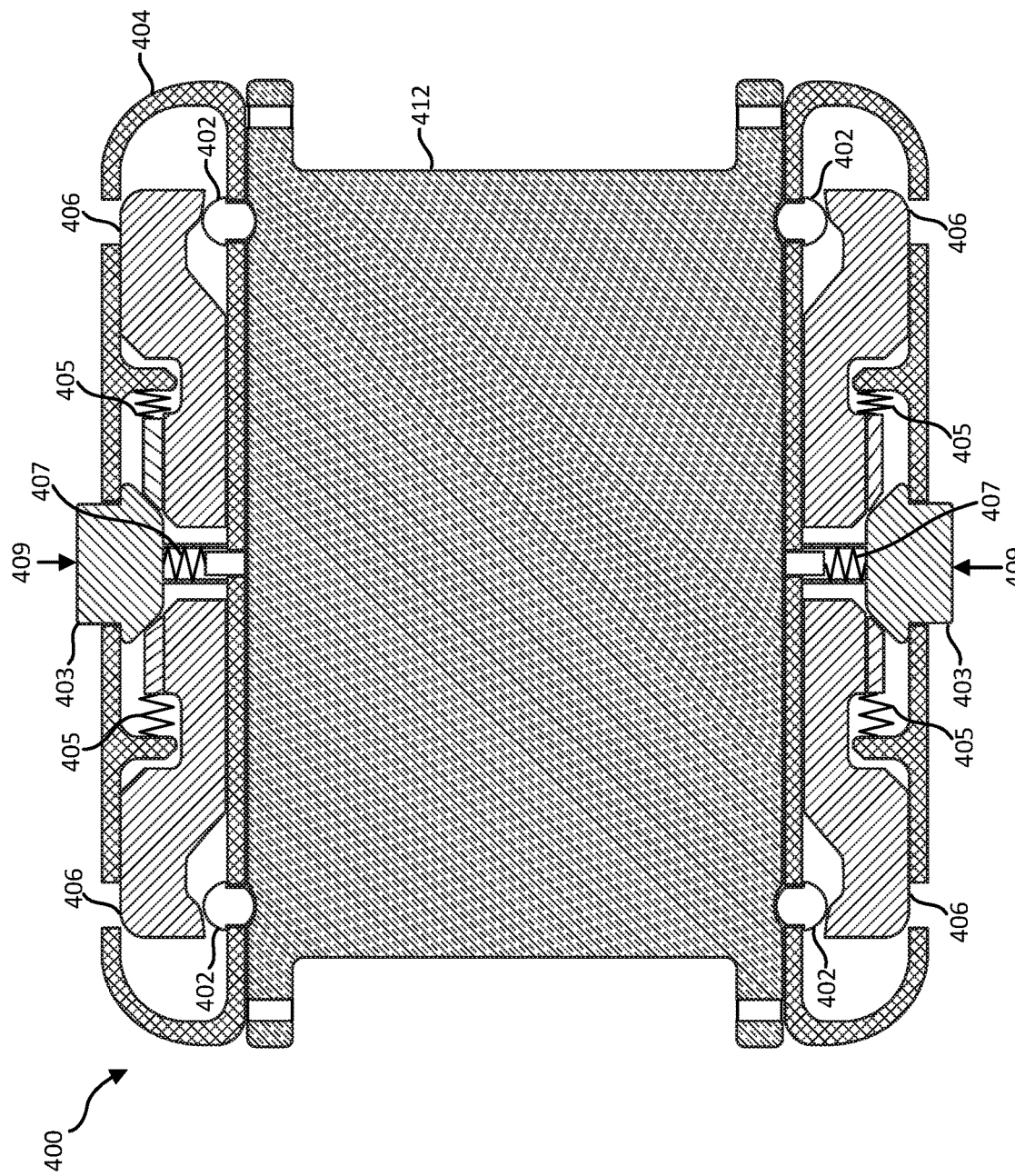
FIG. 4 is a cross-sectional plan view of a detachable wristband system, according to at least one embodiment of the present disclosure.

Wristband system 200 may include a single release mechanism 220 or multiple release mechanisms 220 (e.g., two release mechanisms 220 positioned on opposing sides of wristband system 200 such as spring-loaded buttons 403 of FIG. 4). As shown in FIG. 2A, release mechanism 220 may be positioned on watch body 204 and/or watch band coupling mechanism 210. Although FIG. 2A shows release mechanism 220 positioned at a corner of watch body 204 and at a corner of watch band coupling mechanism 210, release mechanism 220 may be positioned anywhere on watch body 204 and/or watch band coupling mechanism 210 that is convenient for a user of wristband system 200 to actuate. A user of wristband system 200 may actuate release mechanism 220 by pushing, turning, lifting, depressing, shifting, or performing other actions on release mechanism 220. Actuation of release mechanism 220 may release (e.g., decouple) watch body 204 from watch band coupling mechanism 210 and watch band 212 allowing the user to use watch body 204 independently from watch band 212. For example, decoupling watch body 204 from watch band 212 may allow the user to capture images using rear-facing image sensor 115B.

Figure 2B:
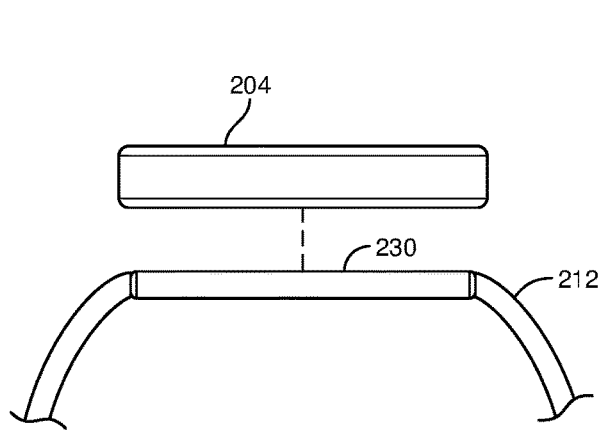
FIG. 2B is a side view of another example wristband system, according to at least one embodiment of the present disclosure.
Figure 2C:
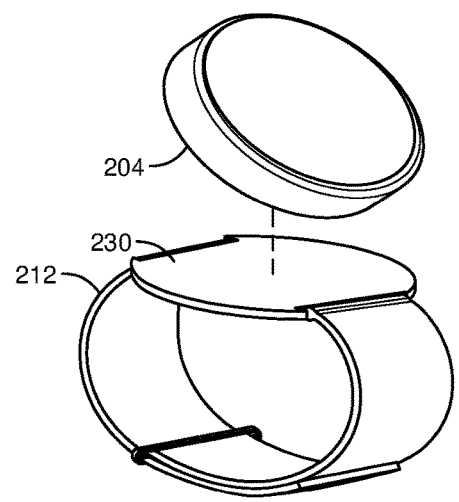
FIG. 2C is a perspective view of another example wristband system, according to at least one embodiment of the present disclosure.

FIG. 2B is a side view and FIG. 2C is a perspective view of another example wristband system. The wristband systems of FIGS. 2B and 2C may include a watch body interface 230. Watch body 204 may be detachably coupled to watch body interface 230. Watch body 204 may be detachably coupled to watch body interface 230 as described in detail with reference to FIGS. 2A and 4-13. Watch body 204 may be detachably coupled to watch body interface 230 through a friction fit, magnetic coupling, a rotation-based connector, a shear-pin coupler, a retention spring, one or more magnets, a clip, a pin shaft, a hook and loop fastener, or a combination thereof.

In some examples, watch body 204 may be decoupled from watch body interface 230 by actuation of a release mechanism. The release mechanism may include, without limitation, a button, a knob, a plunger, a handle, a lever, a fastener, a clasp, a dial, a latch, or a combination thereof. In some examples, the wristband system functions may be executed independently in watch body 204, independently in watch body interface 230, and/or in communication between watch body 204 and watch body interface 230. Watch body interface 230 may be configured to operate independently (e.g., execute functions independently) from watch body 204. Additionally or alternatively, watch body 204 may be configured to operate independently (e.g., execute functions independently) from watch body interface 230. As will be described in more detail below with reference to the block diagram of FIG. 3, watch body interface 230 and/or watch body 204 may each include the independent resources required to independently execute functions. For example, watch body interface 230 and/or watch body 204 may each include a power source (e.g., a battery), a memory, data storage, a processor (e.g., a CPU), communications, a light source, and/or input/output devices.

In this example, watch body interface 230 may include all of the electronic components of watch band 212. In additional examples, one or more electronic components may be housed in watch body interface 230 and one or more other electronic components may be housed in portions of watch band 212 away from watch body interface 230.

Figure 3:
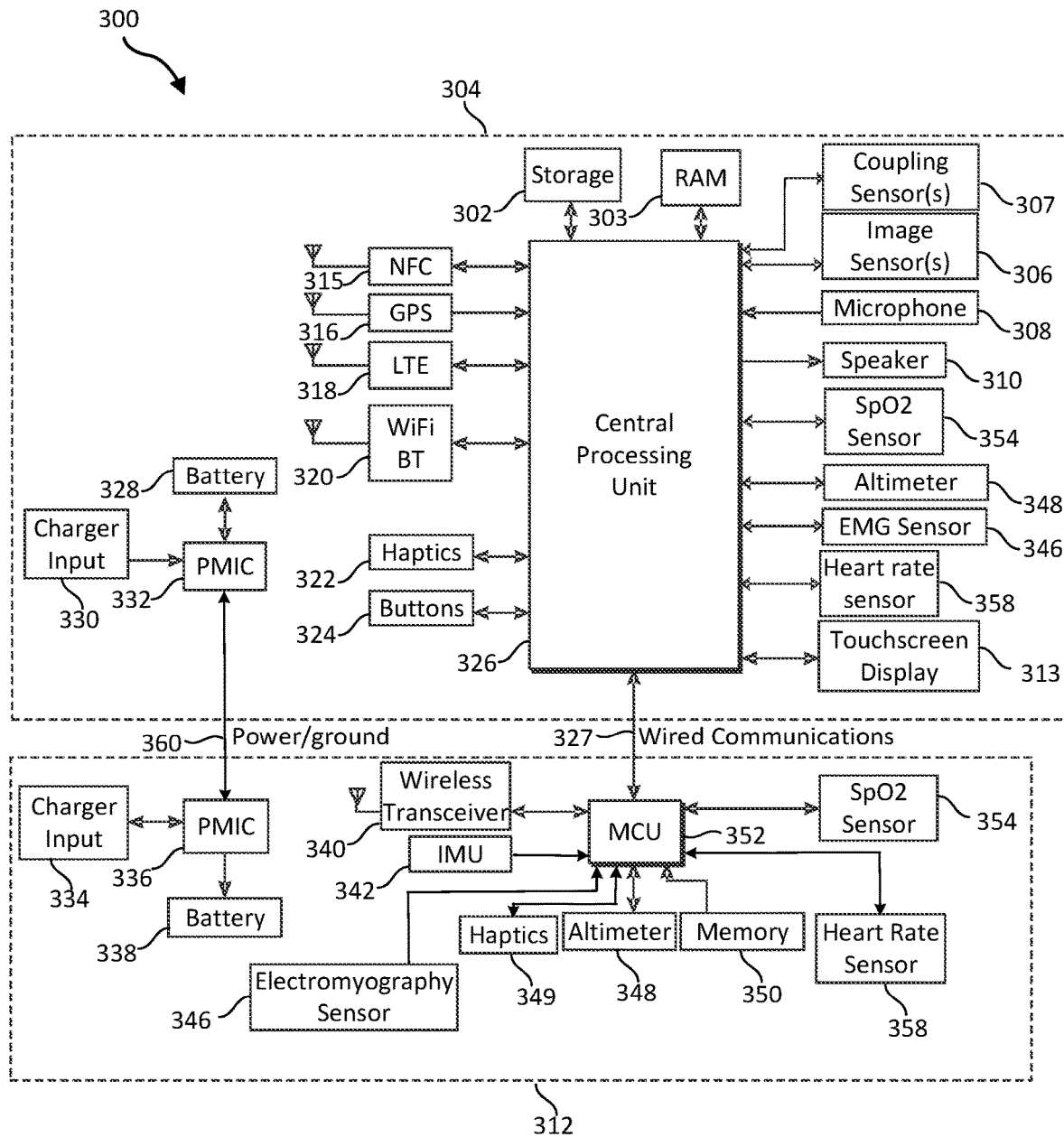
FIG. 3 is an example block diagram of a wristband system, according to at least one embodiment of the present disclosure.

FIG. 3 is a block diagram of an example wristband system 300, according to at least one embodiment of the present disclosure. Referring to FIG. 3, wristband system 300 may have a split architecture (e.g., a split mechanical architecture, a split electrical architecture) between a watch body 304 and a watch band 312, as discussed above with reference to FIGS. 1 and 2. Each of watch body 304 and watch band 312 may have a power source, a processor, a memory, sensors, a charging device, and a communications device that enables each of watch body 304 and watch band 312 to execute computing, controlling, communication, and sensing functions independently in watch body 304, independently in watch band 312, and/or in communication between watch body 304 and watch band 312.

For example, watch body 304 may include battery 328, CPU 326, storage 302, heart rate sensor 358, EMG sensor 346, SpO2 sensor 354, altimeter 348, random access memory 303, charging input 330 and communication devices NFC 315, LTE 318, and WiFi/Bluetooth™ 320. Similarly, watch band 312 may include battery 338, microcontroller unit 352, memory 350, heart rate sensor 358, EMG sensor 346, SpO2 sensor 354, altimeter 348, charging input 334 and wireless transceiver 340. In some examples, a level of functionality of at least one of watch band 312 or watch body 304 may be modified when watch body 304 is detached from watch band 312. The level of functionality that may be modified may include the functionality of at least one sensor (e.g., heart rate sensor 358, EMG sensor 346, etc.). Each of watch body 304 and watch band 312 may execute instructions stored in storage 302 and memory 350 respectively that enables at least one sensor (e.g., heart rate sensor 358, EMG sensor 346, etc.) in watch band 312 to acquire data when watch band 312 is detached from watch body 304 and when watch band 312 is attached to watch body 304.

Watch body 304 and watch band 312 may further execute instructions stored in storage 302 and memory 350 respectively that enables watch band 312 to transmit the acquired data to watch body 304 (or an HMD) using wired communications 327 and/or wireless transceiver 340. As described above with reference to FIGS. 1A and 1B, wristband system 300 may include a user interface. For example, watch body 304 may display visual content to a user on touchscreen display 313 and play audio content on speaker 310. Watch body 304 may receive user inputs such as audio input from microphone 308 and touch input from buttons 324. Watch body 304 may also receive inputs associated with a user's location and/or surroundings. For example, watch body 304 may receive location information from GPS 316 and/or altimeter 348 of watch band 312.

Watch body 304 may receive image data from at least one image sensor 306 (e.g., a camera). Image sensor 306 may include front-facing image sensor 115A and/or rear-facing image sensor 115B. Front-facing image sensor 115A and/or rear-facing image sensor 115B may capture wide-angle images of the area surrounding front-facing image sensor 115A and/or rear-facing image sensor 115B such as hemispherical images (e.g., at least hemispherical, substantially spherical, etc.), 180-degree images, 360-degree area images, panoramic images, ultra-wide area images, or a combination thereof. In some examples, front-facing image sensor 115A and/or rear-facing image sensor 115B may be configured to capture images having a range between 45 degrees and 360 degrees. Certain input information received by watch body 304 (e.g., user inputs, etc.) may be communicated to watch band 312. Similarly, certain input information (e.g., acquired sensor data, neuromuscular sensor data, etc.) received by watch band 312 may be communicated to watch body 304.

Watch body 304 and watch band 312 may receive a charge using a variety of techniques. In some embodiments, watch body 304 and watch band 312 may use a wired charging assembly (e.g., power cords) to receive the charge. Alternatively or in addition, watch body 304 and/or watch band 312 may be configured for wireless charging. For example, a portable charging device may be designed to mate with a portion of watch body 304 and/or watch band 312 and wirelessly deliver usable power to a battery of watch body 304 and/or watch band 312.

Watch body 304 and watch band 312 may have independent power and charging sources to enable each to operate independently. Watch body 304 and watch band 312 may also share power (e.g., one may charge the other) via power management IC 332 in watch body 304 and power management IC 336 in watch band 312. Power management IC 332 and power management IC 336 may share power over power and ground conductors and/or over wireless charging antennas.

Wristband system 300 may operate in conjunction with a health monitoring application that acquires biometric and activity information associated with the user. The health monitoring application may be designed to provide information to a user that is related to the user's health. For example, wristband system 300 may monitor a user's physical activity by acquiring data from IMU 342 while simultaneously monitoring the user's heart rate via heart rate sensor 358 and saturated blood oxygen levels via SpO2 sensor 354. CPU 326 may process the acquired data and display health related information to the user on touchscreen display 313.

Wristband system 300 may detect when watch body 304 and watch band 312 are connected to one another (e.g., mechanically connected and/or electrically connected) or detached from one another. For example, pin(s) 505, power/ground connections 360, wireless transceiver 340, and/or wired communications 327, may detect whether watch body 304 and watch band 312 are mechanically and/or electrically connected to one another (e.g., detecting a disconnect between the one or more electrical contacts of power/ground connections 360 and/or wired communications 327). In some examples, when watch body 304 and watch band 312 are mechanically and/or electrically disconnected from one another (e.g., watch body 312 has been detached from watch band 312 as described with reference to FIGS. 4-14C), watch body 304 and/or watch band 312 may operate with modified level of functionality (e.g., reduced functionality) as compared to when watch body 304 and watch band 312 are mechanically and/or electrically connected to one another. The modified level of functionality (e.g., switching from full functionality to reduced functionality and from reduced functionality to full functionality) may occur automatically (e.g., without user intervention) when wristband system 300 determines that watch body 304 and watch band 312 are mechanically and/or electrically disconnected from one another and connected to each other, respectively.

Modifying the level of functionality (e.g., reducing the functionality in watch body 304 and/or watch band 312) may reduce power consumption in battery 328 and/or battery 338. For example, any of the sensors (e.g., heart rate sensor 358, EMG sensor 346, SpO2 sensor 354, altimeter 348, etc.), processors (e.g., CPU 326, microcontroller unit 352, etc.), communications elements (e.g., NFC 315, GPS 316, LTE 318, WiFi/Bluetooth™ 320, etc.), or actuators (e.g., haptics 322, 349, etc.) may reduce functionality and/or power consumption (e.g., enter a sleep mode) when watch body 304 and watch band 312 are mechanically and/or electrically disconnected from one another. Watch body 304 and watch band 312 may return to full functionality when watch body 304 and watch band 312 are mechanically and/or electrically connected to one another. The level of functionality of each of the sensors, processors, actuators, and memory may be independently controlled.

As described above, wristband system 300 may detect when watch body 304 and watch band 312 are coupled to one another (e.g., mechanically connected and/or electrically connected) or decoupled from one another. In some examples, watch body 304 may modify a level of functionality (e.g., activate and/or deactivate certain functions) based on whether watch body 304 is coupled to watch band 312. For example, CPU 326 may execute instructions that detect when watch body 304 and watch band 312 are coupled to one another and activate front-facing image sensor 115A. CPU 326 may activate front-facing image sensor 115A based on receiving user input (e.g., a user touch input from touchscreen display 313, a user voice command from microphone 308, a user gesture recognition input from EMG sensor 346, etc.).

When CPU 326 detects that watch body 304 and watch band 312 are decoupled from one another, CPU 326 may modify a level of functionality (e.g., activate and/or deactivate additional functions). For example, CPU 326 may detect when watch body 304 and watch band 312 are decoupled from one another and activate rear-facing image sensor 115B. CPU 326 may activate rear-facing image sensor 115B automatically (e.g., without user input) and/or based on receiving user input (e.g., a touch input, a voice input, an intention detection, etc.). Automatically activating rear-facing image sensor 115B may allow a user to take wide-angle images without having to provide user input to activate rear-facing image sensor 115B.

In some examples, rear-facing image sensor 115B may be activated based on an image capture criterion (e.g., an image quality, an image resolution, etc.). For example, rear-facing image sensor 115B may receive an image (e.g., a test image). CPU 326 and/or rear-facing image sensor 115B may analyze the received test image data and determine whether the test image data satisfies the image capture criterion (e.g., the image quality exceeds a threshold, the image resolution exceeds a threshold, etc.). Rear-facing image sensor 115B may be activated when the test image data satisfies the image capture criterion. Additionally or alternatively, rear-facing image sensor 115B may be deactivated when the test image data fails to satisfy the image capture criterion.

In some examples, CPU 326 may detect when watch body 304 is coupled to watch band 312 and deactivate rear-facing image sensor 115B. CPU 326 may deactivate rear-facing image sensor 115B automatically (e.g., without user input) and/or based on receiving user input (e.g., a touch input, a voice input, an intention detection, etc.). Deactivating rear-facing image sensor 115B may automatically (e.g., without user input) reduce the power consumption of watch body 304 and increase the battery charge time in watch body 304. In some examples, wristband system 300 may include a coupling sensor 307 that senses whether watch body 304 is coupled to or decoupled from watch band 312. Coupling sensor 307 may be included in any of watch body 304, watch band 312, or watch band coupling mechanism 210 of FIG. 2A. Coupling sensor 307 (e.g., a proximity sensor) may include, without limitation, an inductive proximity sensor, a limit switch, an optical proximity sensor, a capacitive proximity sensor, a magnetic proximity sensor, an ultrasonic proximity sensor, or a combination thereof. CPU 326 may detect when watch body 304 is coupled to watch band 312 or decoupled from watch band 312 by reading the status of coupling sensor 307.

FIG. 4 is a cross-sectional plan view of a detachable wristband system 400, according to at least one embodiment of the present disclosure. Wristband system 400 may include watch body 404 that is detachable from, and attachable to, watch band 412. Watch body 404 may detach from watch band 412 by simultaneously pressing buttons 403 inward towards watch band 412 as indicated by direction arrows 409. Buttons 403 may be disposed on opposite sides of watch body 404 and biased to an outward position from watch band 412 by springs 407 (e.g., helical compression springs). When spring-loaded buttons 403 are pressed inward, pins 402 may retract from an indentation in watch band 412 such that a retaining force exerted by pins 402 on watch body 404 is removed. The removal of the retaining force allows watch body 404 to be easily decoupled from watch band 412. In some examples, pins 402 may be spring-loaded and configured to retract away from watch band 412 when the retaining force is removed.

Although FIG. 4 shows four pins 402 that detachably couple watch body 404 to watch band 412, the present disclosure is not so limited and any number of pins 402 may be used. In some examples, by simultaneously pressing buttons 403 inward towards watch band 412 as indicated by direction arrows 409, buttons 403 may exert a force on lock bars 406 causing lock bars 406 to shift in position such that pins 402 may retract from an indentation in watch band 412 and the retaining force exerted by pins 402 on watch body 404 is removed.

Buttons 403 may include an angled surface disposed adjacent to an angled surface on lock bars 406. Pressing on buttons 403 in a direction indicated by direction arrows 409 may cause the angled surface of buttons 403 to slide along the angled surface of lock bars 406 thereby causing lock bars 406 to laterally shift to align pins 402 with respective recesses in lock bars 406. Pins 402 may retract from the indentation in watch band 412 and into the respective recesses in lock bars 406. Coupling watch body 404 to watch band 412 may be accomplished by application of a substantially linear force to watch body 404 towards watch band 412. An angled (e.g., curved) face of pins 402 may engage with watch band 412 to cause pins 402 to retract and engage the indentations on watch band 412. When buttons 403 are not pressed, springs 407 may maintain buttons 403 in a retracted position and springs 405 may maintain lock bars 406 in a position that applies the retaining force to pins 402 as described in detail below with reference to FIG. 5.

As described above and shown in FIG. 4, watch band 412 may include indentations with which pins 402 of watch body 404 engage to retain watch body 404 on watch band 412. However, the present disclosure is not limited to this configuration. In some embodiments, the configuration may be reversed in that watch body 404 may include indentations and watch band 412 may include pins 402, lock bars 406, and buttons 403.

Figure 5:
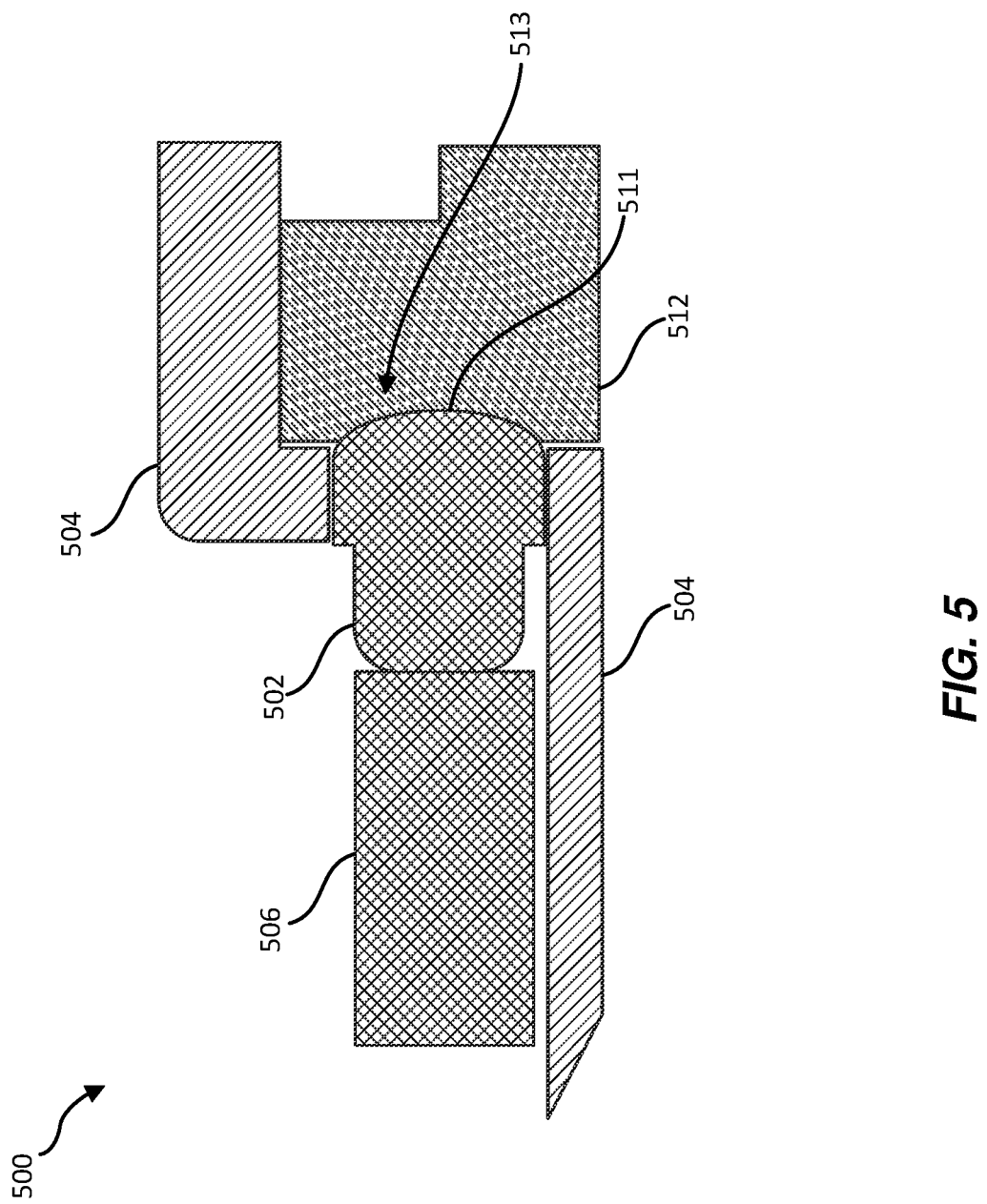
FIG. 5 is a detailed cross-sectional view of a wristband coupling mechanism, according to at least one embodiment of the present disclosure.

FIG. 5 is a detailed cross-sectional view of a wristband coupling mechanism 500, according to at least one embodiment of the present disclosure. Wristband coupling mechanism 500 may include watch body 504 that is detachable from, and attachable to, watch band 512. FIG. 5 shows a cross section of one of multiple wristband coupling mechanisms described above with reference to FIG. 4. By simultaneously pressing buttons (e.g., buttons 403 of FIG. 4) inward towards watch band 512, the buttons may exert a force on lock bar 506 causing lock bar 506 to shift in position such that pin 502 may retract from an indentation 511 in watch band 512 and the retaining force exerted by pin 502 on watch body 504 is removed.

In some examples, the geometry of region 513 of indentation 511 may be configured such that a net force is created by pin 502 that drives watch band 512 toward watch body 504 (e.g., upward from the perspective of FIG. 5) causing mechanical stability to be maintained between watch band 512 and watch body 504. The contoured surface of pin 502 in region 513 may be shaped to create the net force when lock bar 506 exerts a retaining force on pin 502. In some examples, watch band 512 and watch body 504 may have complementary electrical contacts (e.g., pogo pin contacts or pin 502) to allow electrical power and/or signals to pass between watch band 512 and watch body 504 as described above with reference to FIG. 3. In addition to providing mechanical stability, the net force created by pin 502 may maintain the integrity of the electrical contacts between watch band 512 and watch body 504.

Figure 6:
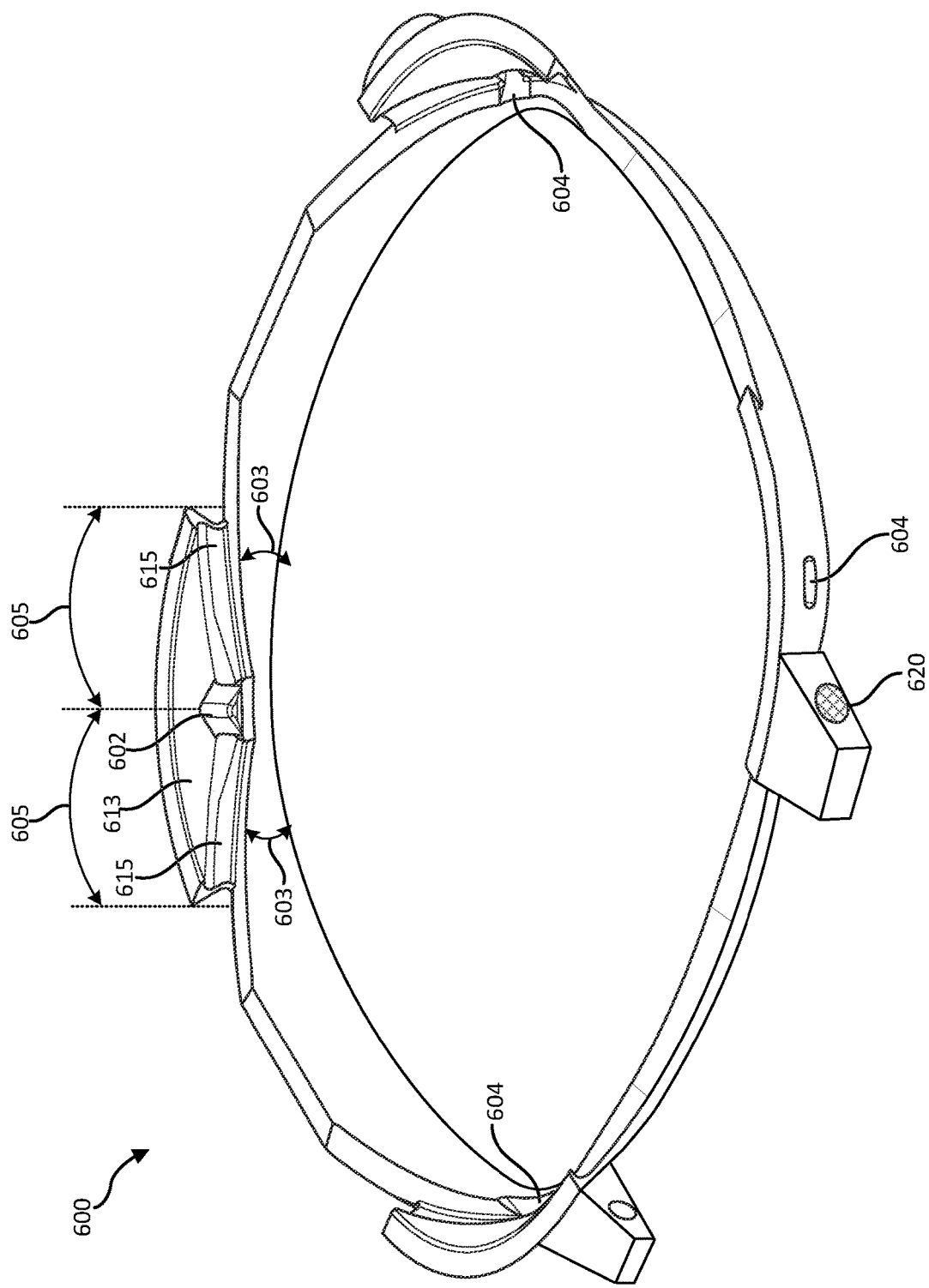
FIG. 6 is a perspective view of a wristband coupling mechanism, according to at least one embodiment of the present disclosure.

FIG. 6 is a perspective view of coupling mechanism 600, according to at least one embodiment of the present disclosure. Coupling mechanism 600 may be part of a watch band that is detachably coupled to a watch body. For example, coupling mechanism 600 may be watch band coupling mechanism 210 of FIG. 2A that detachably couples watch body 204 to watch band 212. A watch body may be coupled to coupling mechanism 600 by applying a substantially linear force on the watch body towards coupling mechanism 600 (e.g., downward in the perspective of FIG. 6) such that at least one spring loaded pawl on the watch body engages lock surfaces 602 and 604 of coupling mechanism 600.

Coupling mechanism 600 may include at least one lock surface 602 that prevents rotation of the watch body when the watch body is coupled to the watch band. Coupling mechanism 600 may include at least one vertical lock surface 604 that prevents vertical movement of the watch body relative to coupling mechanism 600 when the watch body is coupled to the watch band. In some examples, coupling mechanism 600 may include one lock surface 602 to prevent rotational movement and three vertical lock surfaces 604 arranged in a plane to prevent vertical movement.

A watch body may be decoupled from coupling mechanism 600 by applying a rotational force to the watch body such that the at least one spring loaded pawl on the watch body disengages from lock surfaces 602 and 604 of coupling mechanism 600. In some examples, the watch body may be decoupled from coupling mechanism 600 by actuation of release mechanism 620. Release mechanism 620 may include, without limitation, a button, a knob, a plunger, a handle, a lever, a fastener, a clasp, a dial, a latch, or a combination thereof. Coupling mechanism 600 may include a single release mechanism 620 or multiple release mechanisms 620 (e.g., two release mechanisms 620 positioned on opposing corners of coupling mechanism 600).

Although FIG. 6 shows release mechanism 620 positioned at a corner of coupling mechanism 600, release mechanism 620 may be positioned anywhere on coupling mechanism 600 that is convenient for a user to actuate. A user may actuate release mechanism 620 by pushing, turning, lifting, depressing, shifting, or performing other actions on release mechanism 620. Actuation of release mechanism 620 may release (e.g., decouple) the watch body from coupling mechanism 600 allowing the user to use the watch body independently from coupling mechanism 600 and the watch band.

Coupling mechanism 600 may include ramp surfaces (e.g., tapered surfaces) in the corners of coupling mechanism 600 to aid in the coupling. For example, ramp surface 613 is shown in FIG. 6 in one corner of coupling mechanism 600. Each of the corners of coupling mechanism 600 may include ramp surface 613. Additionally or alternatively, coupling mechanism 600 may include slots in the corners of coupling mechanism 600 to aid in the rotational decoupling of the watch body from the watch band. For example, coupling mechanism 600 may include two slots 615 in each corner of coupling mechanism 600. Slots 615 may include one end disposed next to lock surface 602 and/or 604.

Slots 615 may be angled away from lock surface 602 and/or 604 such that a rotating motion (e.g., a twisting motion) of the watch body relative to coupling mechanism 600 allows the watch body to be rotated off coupling mechanism 600 in either a clockwise or counterclockwise direction. Slots 615 may be angled as they extend away from lock surface 602 and/or 604 at an angle 603. Angle 603 may be defined as an angle from a bottom plane of the coupling mechanism 600. Angle 603 may be configured to allow the watch body to be rotated smoothly off coupling mechanism 600 in either a clockwise or counterclockwise direction. For example, angle 603 may be between about 5 degrees and about 30 degrees, such as between about 10 degrees and 20 degrees (e.g., about 10 degrees, about 12 degrees, about 14 degrees, about 16 degrees, about 18 degrees, or about 20 degrees). In some examples, slots 615 may have a length such that rotation of the watch body may cause the watch body to be detached from the coupling mechanism 600 when a pin of the watch body reaches an end of slots 615.

For example, rotation of the watch body in either a clockwise or counterclockwise direction by an angle 605 may cause the pin to reach the end of slots 615 and watch body to be detached from the coupling mechanism 600. Angle 605 may be between about 5 degrees and about 30 degrees, such as between about 10 degrees and about 20 degrees (e.g., about 10 degrees, about 12 degrees, about 14 degrees, about 16 degrees, about 18 degrees, or about 20 degrees). The mechanisms and methods for coupling and decoupling the watch body to coupling mechanism 600 will be described in more detail below with reference to FIGS. 7 and 8.

Figure 7:
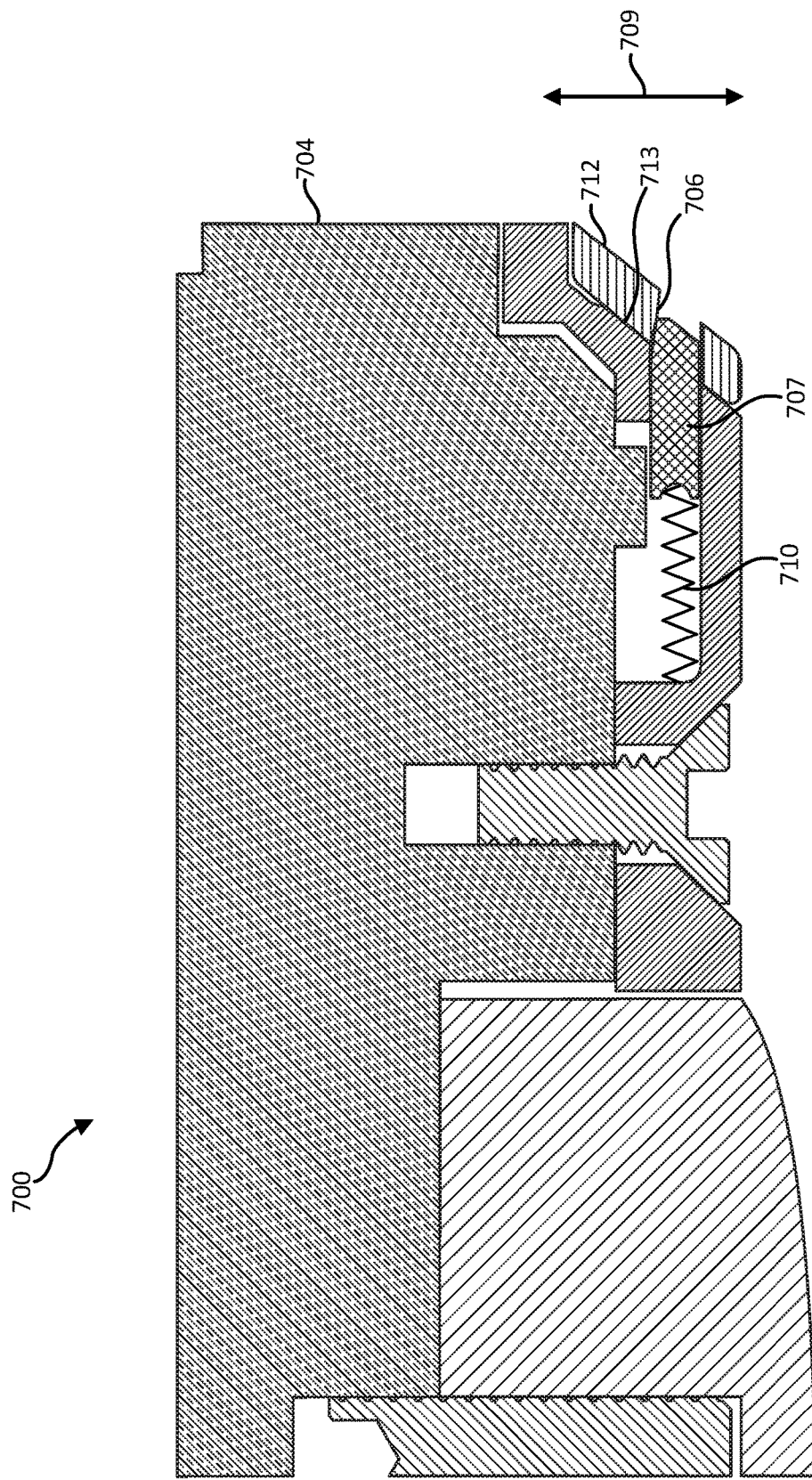
FIG. 7 is a partial cross-sectional view of a wristband coupling mechanism that prevents vertical movement, according to at least one embodiment of the present disclosure.

FIG. 7 is a cross-sectional view of a wristband coupling mechanism 700 that prevents vertical movement, according to at least one embodiment of the present disclosure. FIG. 7 shows watch body 704 coupled to watch band 712. Watch body 704 may be coupled to watch band 712 by applying a substantially linear force to watch body 704 towards watch band 712 such that spring-loaded pawl 707 on watch body 704 engages vertical lock surface 706. When watch body 704 is coupled to watch band 712, vertical lock surface 706 may prevent vertical movement, as indicated by direction arrow 709, of watch body 704 relative to watch band 712. Spring 710 (e.g., a helical compression spring, a leaf spring, or a torsion spring) may exert a radially-outward force on pawl 707 towards vertical lock surface 706 such that an angled surface disposed on an upper end of pawl 707 is configured to engage vertical lock surface 706 to secure watch body 704 to the watch band in a linear direction (e.g., a vertical direction).

When coupling watch body 704 to watch band 712, a substantially linear force may be applied to watch body 704 towards watch band 712 causing pawl 707 to initially contact ramp surface 713. Spring 710 may be compressed radially inward and pawl 707 may travel inward until pawl 707 contacts vertical lock surface 706 and secures watch band 712 to watch body 704. When decoupling watch body 704 from watch band 712, a rotating motion (e.g., a twisting motion) is applied to watch body 704 relative to watch band 712 causing an upper end of pawl 707 to travel in an angled slot (e.g., slot 615 of FIG. 6) such that pawl 707 becomes disengaged from vertical lock surface 706. Thus, the rotating motion may allow watch body 704 to be rotated off watch band 712 in either a clockwise or counterclockwise direction.

As explained above, watch body 704 may be secured to watch band 712 via pawl 707 and spring 710. However, this disclosure is not limited to this securing mechanism. For example, in additional embodiments, watch body 704 may be at least partially secured to watch band 712 with one or more magnets as described below with reference to FIGS. 9-13. In some examples, magnets may be used in addition to pawl 707 and spring 710 to increase a force by which watch body 704 is secured to watch band 712 when engaged.

Figure 8:
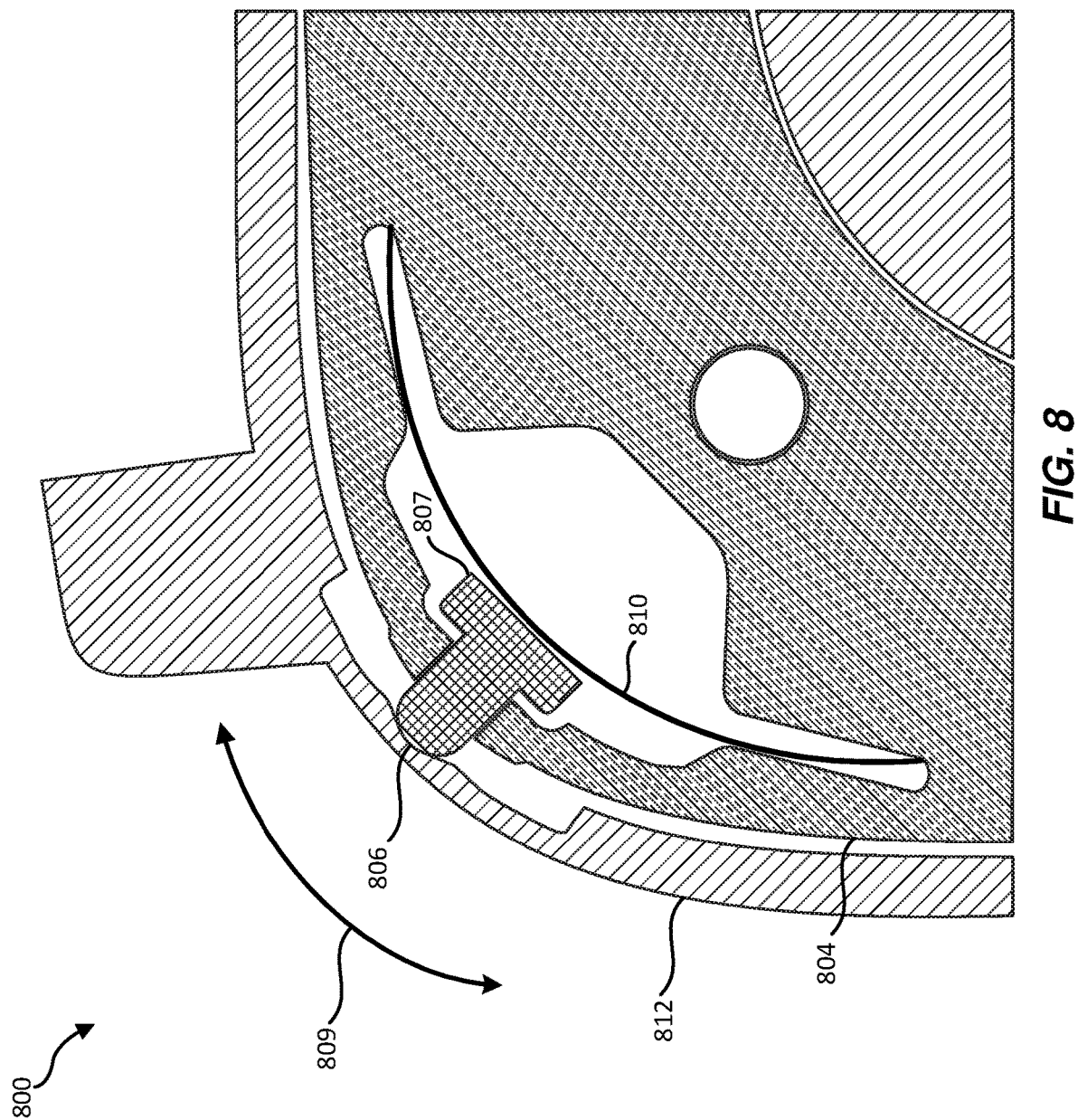
FIG. 8 is a partial cross-sectional view of a wristband coupling mechanism that prevents rotational movement, according to at least one embodiment of the present disclosure.

FIG. 8 is a cross-sectional view of a wristband coupling mechanism 800 that inhibits rotational movement between watch body 804 and watch band 812, according to at least one embodiment of the present disclosure. FIG. 8 shows watch body 804 coupled to watch band 812. Watch body 804 may be coupled to watch band 812 by applying a substantially linear force to watch body 804 towards watch band 812 such that spring-loaded pawl 807 engages rotational lock surface 806. When watch body 804 is coupled to watch band 812, rotational lock surface 806 may inhibit rotational movement, as indicated by direction arrow 809, of watch body 804 relative to watch band 812. Spring 810 (e.g., a torsion spring) may exert a radially outward force on pawl 807 towards rotational lock surface 806 such that an angled (e.g., contoured) surface disposed on an upper end of pawl 807 engages rotational lock surface 806 to secure watch body 804 to watch band 812 in a rotational direction.

When coupling watch body 804 to watch band 812, a substantially linear force may be applied to watch body 804 towards watch band 812 causing pawl 807 to contact a ramp surface (e.g., such as ramp surface 613 of FIG. 6) such that spring 810 is compressed radially inward and pawl 807 travels inward until pawl 807 contacts rotational lock surface 806 and secures watch band 812 to watch body 804. In other words, watch body 804 may be coupled to watch band 812 by linearly pushing watch body 804 down into engagement with watch band 812 with or without rotation of watch body 804 relative to watch band 812. When decoupling watch body 804 from watch band 812, a rotating force (e.g., a twisting force) may be applied to watch body 804 relative to watch body 804 to overcome a spring force from spring 810, causing pawl 807 to retract away from rotational lock surface 806. An upper end of pawl 807 may travel in an angled slot (e.g., such as slot 615 of FIG. 6) such that the rotating motion allows watch body 804 to be rotated off watch band 812 in either a clockwise or counterclockwise direction.

Watch body 804 may have a shape that is complementary to watch band 812. For example, watch body 804 and watch band 812 may each be substantially rectangular, square, circular, hexagonal, octagonal, rectangular with rounded corners (as illustrated in FIG. 8), or any other suitable shape.

Figure 9:
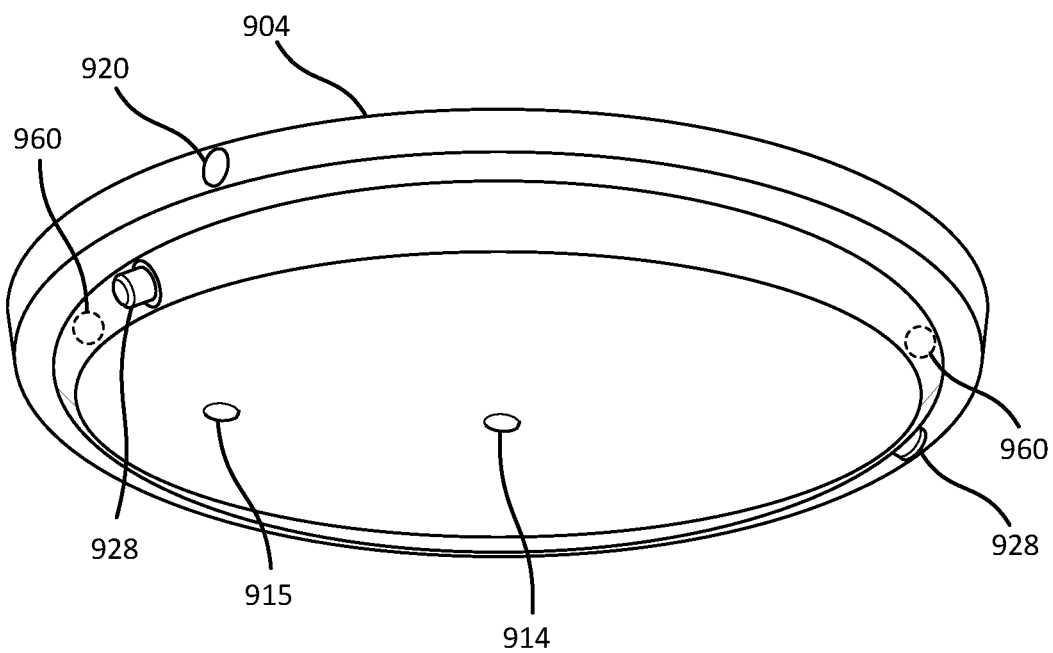
FIG. 9 is a bottom perspective view of an example watch body, according to at least one embodiment of the present disclosure.
Figure 10:
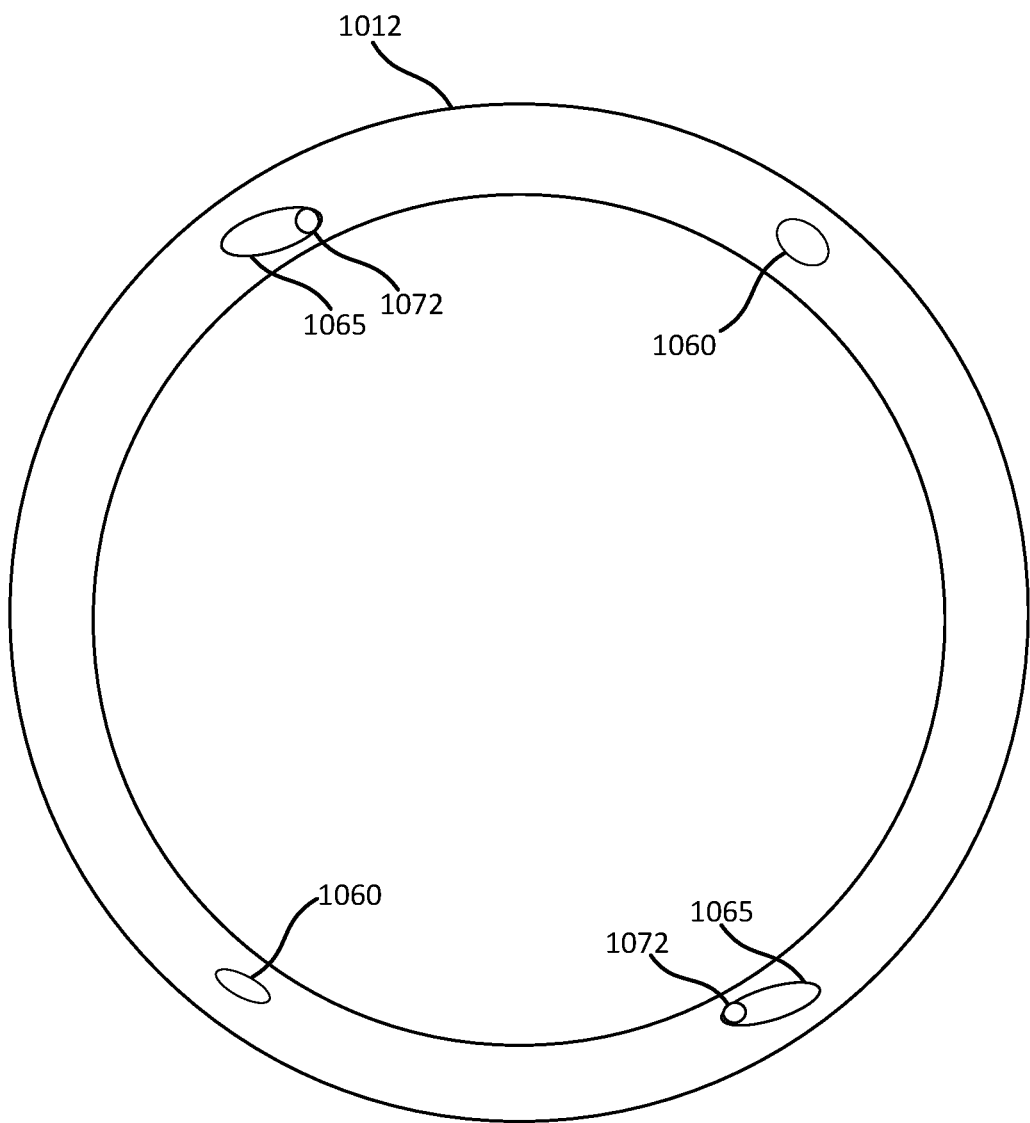
FIG. 10 is a top perspective view of an example watch band, according to at least one embodiment of the present disclosure.

FIG. 9 is a bottom perspective view of a bottom portion of watch body 904 uncoupled from a watch band, according to at least one embodiment of the present disclosure. FIG. 10 is a top perspective view of a watch band 1012 to which watch body 904 of FIG. 9 may be coupled or uncoupled, according to at least one embodiment of the present disclosure. Watch body 904 may be coupled and/or uncoupled from watch band 1012 using any type motion and/or mechanism. For example, watch body 904 may be coupled to and/or uncoupled from watch band 1012 by applying a twisting motion, a linear motion, a turning motion, a shaking motion, a bending motion, a pushing motion, a pulling motion, a helical motion, or a combination thereof. In some examples, watch body 904 may be coupled and/or uncoupled from watch band 1012 using a sequence of the aforementioned motions. For example, watch body 904 may couple to and/or uncouple from watch band 1012 by a twisting motion of watch body 904 relative to watch band 1012. For example, a user may place watch body 904 proximate to watch band 1012. At least one watch body magnet 960 may be attracted to a watch band magnet 1060 when watch body 904 is close to watch band 1012 (e.g., when the center of watch body 904 is placed approximately on top of the center of watch band 1012). The attraction between watch body magnet 960 and watch band magnet 1060 may align watch body 904 to a pre-couple position relative to watch band 1012. The pre-couple position of watch body 904 to watch band 1012 may be a position in which a coupling mechanism between watch body 904 and watch band 1012 is pre-engaged. In some examples, the attraction between watch body magnet 960 and watch band magnet 1060 may couple (e.g., secure) watch body 904 to watch band 1012.

Subsequent to the pre-coupled alignment of watch body 904 to watch band 1012, the user may rotate watch body 904 relative to watch band 1012 in order to couple watch body 904 to watch band 1012. For example, the user may rotate watch body 904 in a clockwise direction as described in detail below with reference to FIGS. 11 and 12. In some examples, the user may rotate watch body 904 relative to watch band 1012 in a clockwise direction by less than 5 degrees, by about 5 degrees to 10 degrees, by about 10 degrees to 15 degrees, or by more than 15 degrees. As described in detail below with reference to FIGS. 11-13, latch pin 928 may be configured to engage a recess 1072 (e.g., a hole, a slot) in watch band 1012 to inhibit movement of watch body 904 when watch body 904 is coupled to watch band 1012.

In some examples, watch body 904 may be decoupled from watch band 1012 by applying a rotational force to watch body 904 while pressing a button 920. Pressing button 920 may actuate a push-button decoupling mechanism (e.g., push-button decoupling mechanism 1100 as described in detail below with reference to FIG. 11) allowing watch body 904 to rotate off of watch band 1012. In some examples, a sensor 914 (e.g., a proximity sensor, a heart rate monitor sensor) may be configured to sense when watch body 904 is decoupled from watch band 1012. A processor (e.g., CPU 326 of FIG. 3) of watch body 904 may be configured to detect the decoupled status and modify a function of watch body 904. For example, the processor may execute instructions to enable an image sensor (e.g., rear-facing image sensor 915) and/or change a power consumption setting when watch body 904 is decoupled from watch band 1012. Additionally or alternatively, a processor of watch body 904 may be configured to detect a coupled status and execute instructions to disable rear-facing image sensor 915 and/or change a power consumption setting.

In some examples, button 920 may also be used to couple watch body 904 to watch band 1012. For example, a user may press button 920 to enable watch body 904 to shift into the pre-coupled position in which watch body magnet 960 is aligned with watch band magnet 1060. As the user twists watch body 904 from the pre-coupled position to the coupled position, the user may release button 920 to enable latch pin 928 to engage recess 1072 of watch band 1012. In some examples, watch band 1012 may include a latching mechanism and watch body 904 may include a recess configured to accept a latch pin disposed on watch band 1012.

Figure 11:
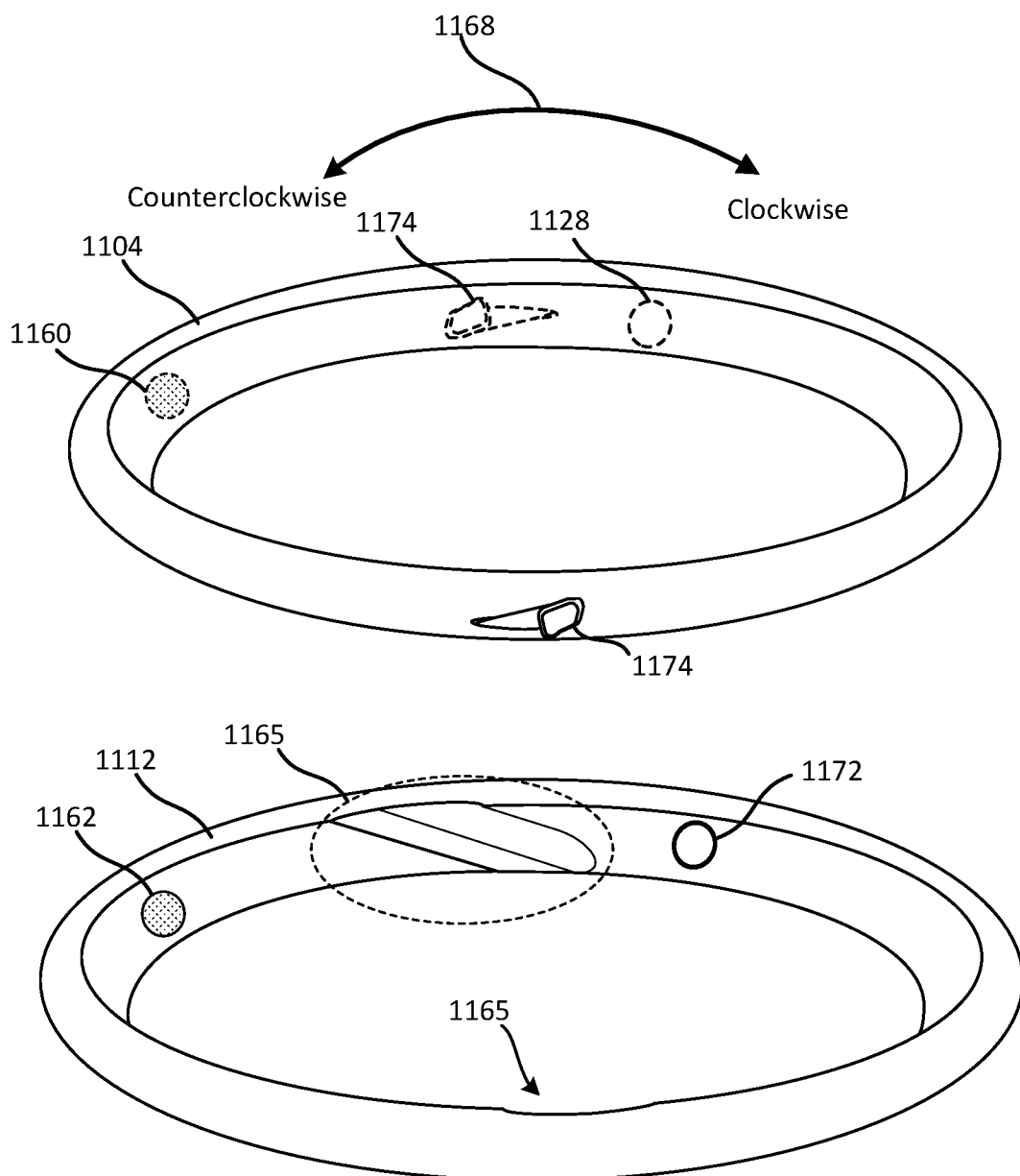
FIG. 11 is a perspective view of an example watch body uncoupled from an example watch band, according to at least one embodiment of the present disclosure.

FIG. 11 is a perspective view of a bottom portion of a watch body 1104 uncoupled from a watch band 1112, according to at least one additional embodiment of the present disclosure. Watch body 1104 may couple to and/or uncouple from watch band 1112 by a twisting motion of watch body 1104 relative to watch band 1112. For example, to couple watch body 1104 to watch band 1112, a user may place watch body 1104 on top of watch band 1112. At least one watch body magnet 1160 may be attracted to at least one watch band magnet 1162 when the center of watch body 1104 is placed approximately on top of the center of watch band 1112. The attraction between watch body magnet(s) 1160 and watch band magnet(s) 1162 may align watch body 1104 to a pre-coupled position relative to watch band 1112. After aligning watch body 1104 to watch band 1112 to the pre-coupled position, the user may rotate watch body 1104 relative to watch band 1112 in order to couple watch body 1104 to watch band 1112.

In some examples, a tab 1174 of watch body 1104 may be configured to travel along a slot 1165 of watch band 1112 thereby drawing watch body 1104 closer to watch band 1112 and into a coupled position. Although FIG. 11 shows two sets of tabs 1174 and slots 1165 disposed in opposite corners, the present disclosure is not so limited and any number of sets of tabs 1174 and slots 1165 may be used. For example, each corner may include a set of tabs 1174 and slots 1165 or only one corner may include a set of tabs 1174 and slots 1165. The user may rotate watch body 1104 relative to the watch band in a clockwise direction as indicated by direction arrow 1168. In some examples, the user may rotate watch body 1104 relative to the watch band in a clockwise direction by less than 5 degrees, by about 5 degrees to 10 degrees, by about 10 degrees to 15 degrees, or by more than 15 degrees. Although FIG. 11 shows watch body 1104 coupling to watch band 1112 by a clockwise twisting motion, the present disclosure is not so limited and watch body 1104 may couple to watch band 1112 by a counter-clockwise twisting motion as indicated by direction arrow 1168.

As described in detail below with reference to FIG. 13, a latch pin 1128 may be configured to engage a recess 1172 (e.g., a hole, a slot) in watch band 1112 to inhibit movement of watch body 1104 when watch body 1104 is coupled to watch band 1112.

In some examples, watch body 1104 may be decoupled from watch band 1112 by twisting watch body 1104 in a counterclockwise direction (or clockwise direction) as indicated by direction arrow 1168 while a button is depressed on watch band 1104. Pressing a button may actuate a push-button decoupling mechanism (e.g., push-button decoupling mechanism 1100 of FIG. 11) allowing watch body 1104 to rotate off of watch band 1112. In additional embodiments, latch pin 1128 may be spring-biased into a coupled position and a decoupling button may be omitted. In this case, the user may decouple watch body 1104 from watch band 1112 by twisting watch body 1104 in a counterclockwise direction relative to watch band 1112 with sufficient force to overcome a spring force biasing the latch pin 1128 into the coupled position.

Figure 12:
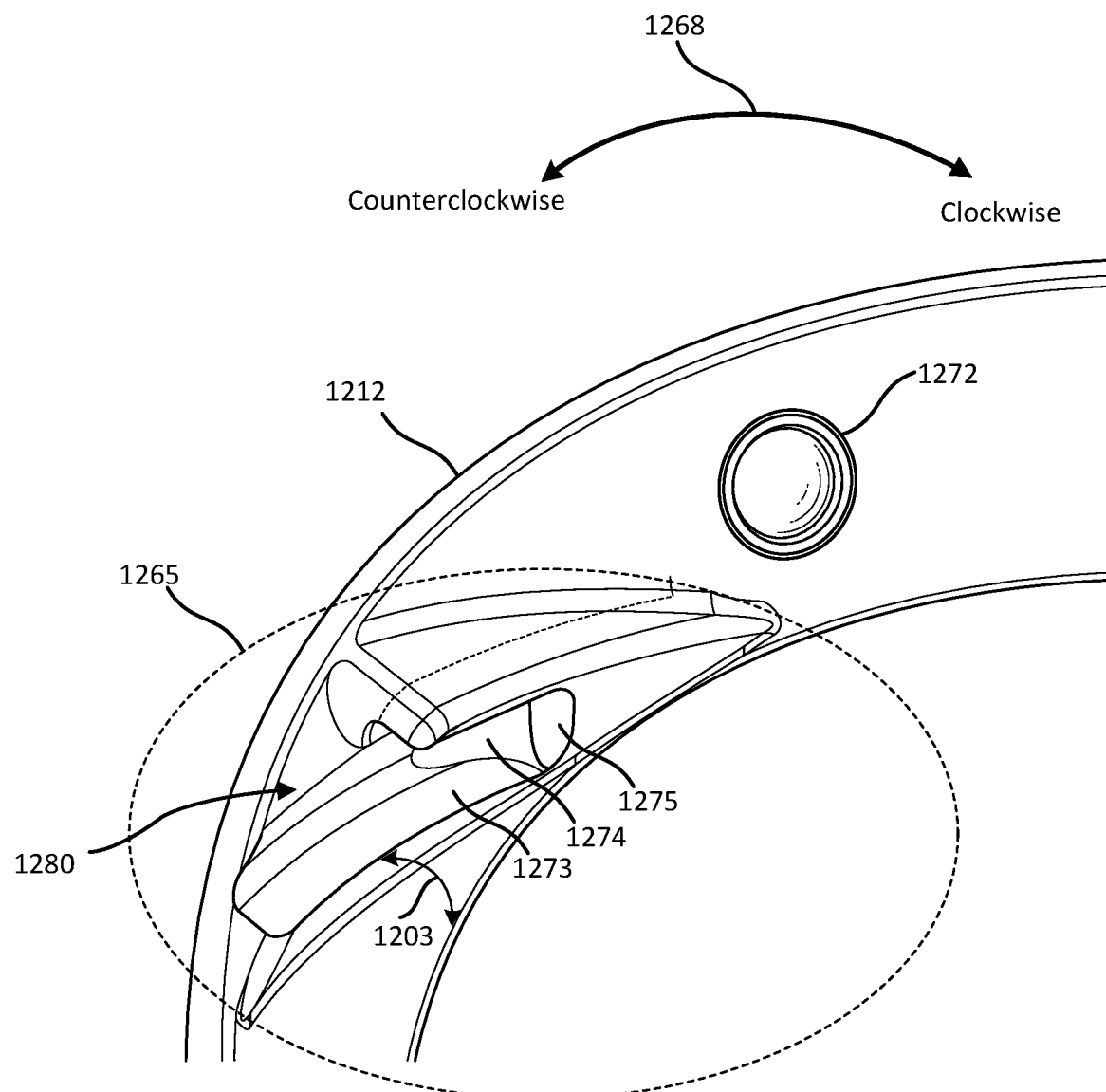
FIG. 12 is a detailed perspective view of a portion of an example watch band, according to at least one embodiment of the present disclosure.

FIG. 12 is a detailed perspective view of a portion of a watch band 1212 configured with a receiver 1265. As described above with reference to FIGS. 9-11, when an attraction between magnets disposed in watch band 1212 and a watch body aligns the watch body to a pre-coupled position relative to watch band 1212, a tab disposed on the watch body (e.g., tab 1174 of FIG. 11) may be aligned with an entry region 1280 of receiver 1265. By rotating the watch body in an engaging direction (e.g., a clockwise direction), as indicated by direction arrow 1268, when the watch body tab is aligned with entry region 1280, the watch body tab may be configured to travel along a ramp surface 1273 (e.g., a tapered surface) in receiver 1265 thereby drawing the watch body closer to watch band 1212. The watch body may be rotated relative to watch band 1212 to a point at which the watch body tab reaches ramp surface end stop 1275 preventing further rotation of the watch body. When the watch body tab reaches end stop 1275, a rounded corner of the watch body tab may abut against a rounded corner 1274 of ramp surface 1273. When the watch body tab reaches end stop 1275 preventing further rotation of the watch body, a latch pin on the watch body (e.g., latch pin 1328 of FIG. 13) may be aligned with recess 1272. The watch body may be rotated relative to watch band 1212 to a point at which a latch pin is aligned and configured to engage recess 1272 (e.g., a hole, an indentation) in watch band 1212. The latch pin (e.g., latch pin 1328 of FIG. 13) may be configured to secure the watch body to watch band 1212.

Ramp surface 1273 may be angled such that a rotating motion (e.g., a twisting motion) of the watch body relative to watch band 1212 allows the watch body to be rotated off watch band 1212 in a counterclockwise direction as indicated by direction arrow 1268. Ramp surface 1273 may be configure at an angle 1203. Angle 1203 may be defined as an angle of ramp surface 1273 relative to a bottom plane of watch band 1212. Angle 1203 may be configured to allow the watch body to be rotated smoothly off watch band 1212 in a counterclockwise direction.

Although FIG. 12 shows watch band 1212 configured to allow the watch body to couple to watch band 1212 through a clockwise rotation and uncouple through a counterclockwise direction, the present disclosure is not so limited and watch band 1212 may be configured to allow the watch body to couple to watch band 1212 through a counterclockwise rotation and uncouple through a clockwise direction. In some examples, angle 1203 may be between about 5 degrees and about 30 degrees, such as between about 10 degrees and 20 degrees (e.g., about 10 degrees, about 12 degrees, about 14 degrees, about 16 degrees, about 18 degrees, or about 20 degrees). In some examples, ramp surface 1273 may have a length such that rotation of the watch body may cause the watch body to be detached from watch band 1212 when a latch pin of the watch body leaves entry region 1280.

Figure 13:
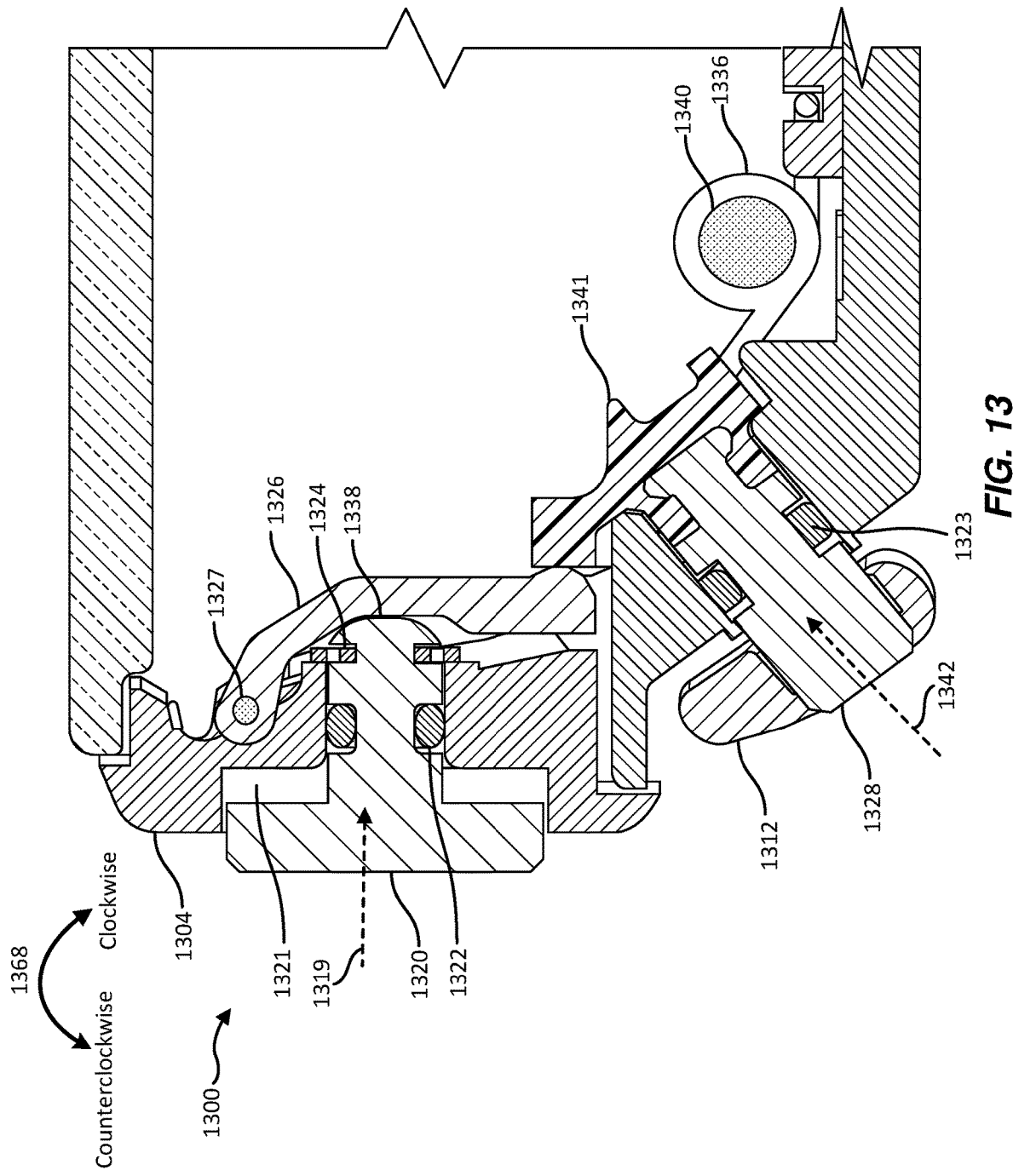
FIG. 13 is a cross-sectional view of a push-button unlatching mechanism, according to at least one embodiment of the present disclosure.

FIG. 13 is a cross-sectional view of a push-button decoupling mechanism 1300, according to at least one embodiment of the present disclosure. As described above with reference to FIGS. 9-12, watch body 1304 may decouple (e.g., physically detach) from watch band 1312 by rotating watch body 1304 relative to watch band 1312. In some embodiments, watch body 1304 may be configured to decouple from watch band 1312 by a user pressing button 1320 and rotating watch body 1304 relative to watch band 1312. Push-button decoupling mechanism 1300 may include button 1320 configured to travel within a recessed area 1321 of watch body 1304. In some examples, the mechanism used to couple and/or decouple watch band 1312 and watch body 1304 may include a latch, a clip, a bar, a bolt, a hasp, a snap, a pin, a spring, a cam, a clamp, a strap, a wedge, a hook, or a combination thereof. In some examples, an O-ring 1322 may surround a shaft of button 1320 and be sized and configured to protect watch body 1304 from ingression of foreign material (e.g., water, dust, hair, etc.).

Push-button decoupling mechanism 1300 may include a lever 1326 configured to pivot about axis 1327. A distal portion of the shaft of button 1320 may contact a middle region 1338 of lever 1326. When button 1320 is pressed in a direction indicated by arrow 1319, the shaft contacting middle region 1338 of lever 1326 may cause lever 1326 to pivot about axis 1327 in a counterclockwise direction (from the view of FIG. 13). When lever 1326 pivots about axis 1327, a lower region of lever 1326 may also pivot in a counterclockwise direction. When lever 1326 pivots counterclockwise due to button 1320 being pressed, a bottom region of lever 1326 may press against a top region of latch pin lever 1341 causing latch pin 1328 to pivot in a clockwise direction (from the view of FIG. 13) about latch axis 1340. When latch pin 1328 pivots in a clockwise direction about latch axis 1340 as indicated by direction arrow 1368, a bottom region of latch pin 1328 may travel in a direction indicated by arrow 1342 and withdraw from a recessed area within watch band 1312.

When the bottom region of latch pin 1328 is extended into the recessed area within watch band 1312, latch pin 1328 may be configured to secure watch body 1304 to watch band 1312. In some examples, watch body 1304 may include multiple push-button decoupling mechanisms 1300. In some examples, an O-ring 1323 may surround a shaft of latch pin 1328 and be sized and configured to protect watch body 1304 from ingression of foreign material (e.g., water, dust, hair, etc.).

Push-button decoupling mechanism 1300 may include a spring 1336 (e.g., a torsion spring, a helical compression spring, a leaf spring, etc.). Spring 1336 may be configured to rotate about axis 1340 and exert a force on latch pin 1328 in a direction opposite to the direction indicated by arrow 1342. Spring 1336 may be configured to exert a force on latch pin lever 1341 which may be transferred to latch pin 1328 such that the bottom region of latch pin 1328 is extended into the recessed area thereby retaining the coupling between watch body 1304 and watch band 1312. The force exerted on latch pin lever 1341 may be transferred to the bottom region of lever 1326 due to the upper region of latch pin 1328 overlapping the bottom region of lever 1326. The force transferred to the bottom region of lever 1326 may be transferred to the contact area between the middle region of lever 1326 and the shaft of button 1320 causing button 1320 to move to an extended position (e.g., not depressed). A retaining clip 1324 may be configured to limit the extend travel length of button 1320 and retain the shaft of button 1320 within watch body 1304.

Watch body 1304 may be configured to decouple from watch band 1312 by a user pressing button 1320 and rotating watch body 1304 relative to watch band 1312. By pressing button 1320, push-button decoupling mechanism 1300 may retract latch pin 1328 from a recess in watch band 1312 allowing a user to twist watch body 1304 off watch band 1312.

In some examples, button 1320 may be configured as a multi-function button. For example, button 1320 may be configured to retract latch pin 1328 from a recess in watch band 1312. Additionally or alternatively, button 1320 may be configured to enable and/or disable a function of watch body 1304. Button 1320 may be configured to sense a user pressing button 1320 and provide the status of the button 1320 (e.g., pressed or not pressed) to a processor (e.g., CPU 326 of FIG. 3). The processor may execute instructions to enable and/or disable a function of watch body 1304 based on the status of button 1320. For example, a user pressing button 1320 may be sensed by the processor. In response, the processor may execute instructions to capture an image (e.g., capture an image using front-facing image sensor 115A of FIG. 1).

In some examples, the multi-function capabilities of button 1320 may be based on a travel length of button 1320. For example, when button 1320 is not pressed and is fully extended, button 1320 may enable latch pin 1328 to remain extended into a recess in watch band 1312 thereby securing watch body 1304 to watch band 1312. When button 1320 is pressed through a first travel length, button 1320 may be configured to provide the status of the button press to a processor in order to execute a function. In some examples, the first travel length may be about 0.1 mm, about 0.2 mm, about 0.3 mm, or more. When button 1320 is pressed through a second travel length, button 1320 may be configured to retract latch pin 1328 from a recess in watch band 1312 allowing a user to twist watch body 1304 off watch band 1312. The second travel length may be about 0.2 mm, about 0.3 mm, about 0.4 mm, about 0.5 mm, or more.

In some examples, the second travel length may be longer than the first travel length. When pressing button 1320, a user may feel a first level of force pushing back on the user's finger (e.g., force feedback) as the button 1320 is pressed through the first travel length. As the user continues to press button 1320 the user may feel an increased force to indicate that the first travel length has been traveled and the second travel length is beginning. This force feedback may allow the user to control the travel lengths of button 1320 and therefore control the associated functions.

Figure 14B:
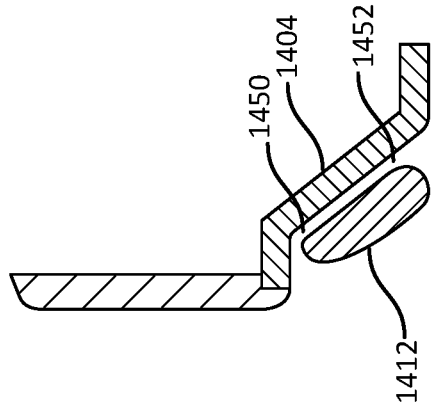
FIG. 14B is a cross-sectional view of an example watch band with a concentric profile, according to at least one embodiment of the present disclosure.
Figure 14C:
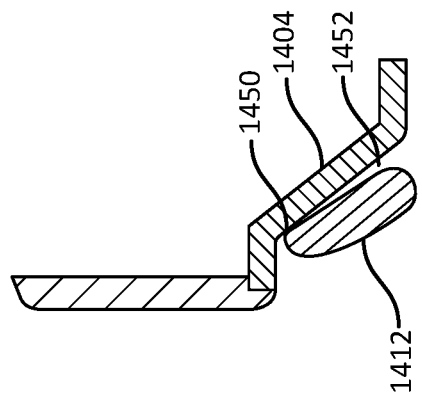
FIG. 14C is a cross-sectional view of an example watch band with a non-concentric profile, according to at least one embodiment of the present disclosure.
Figure 14A:
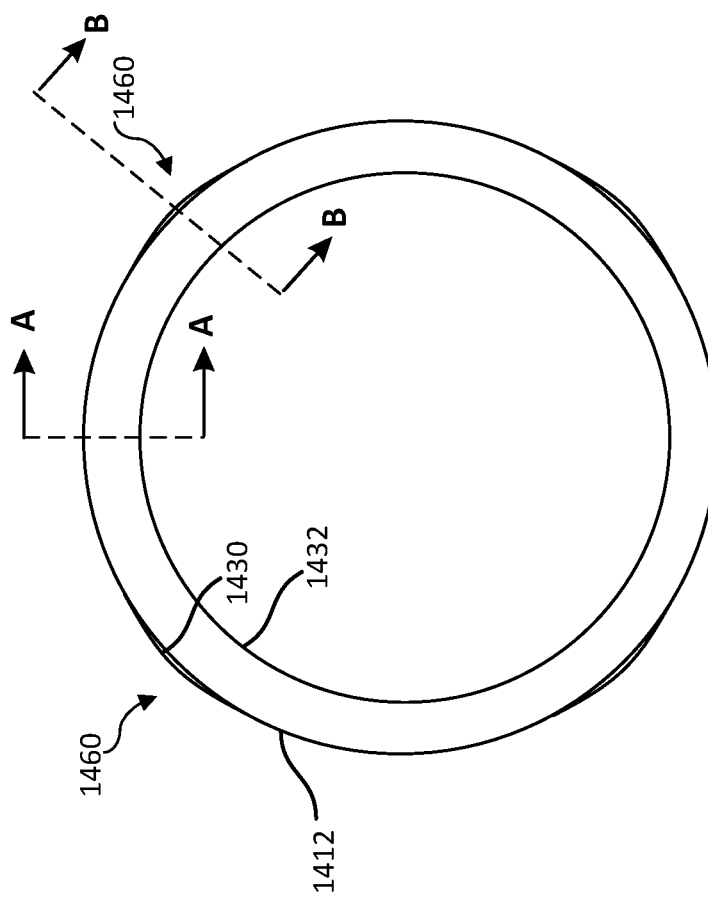
FIG. 14A is a top plan view of an example watch band profile, according to at least one embodiment of the present disclosure.

FIG. 14A is a top plan view of a watch band 1412, according to at least one embodiment of the present disclosure. Watch band 1412 (e.g., a watch cradle) may be worn on a wrist of a user. As described above with reference to FIGS. 9-13, watch band 1412 may couple to a watch body in a variety of ways. When coupling a watch body to watch band 1412, foreign material (e.g., arm hair of the user) may be disposed at the interface between the watch body and watch band 1412. Embodiments of the present disclosure may inhibit (e.g., prevent and/or reduce) a trapping of the foreign material at the interface between the watch body and watch band 1412. For example, watch band 1412 may be configured to include a spacing gap between the watch body and watch band 1412 to prevent a user's arm hair from being trapped (e.g., pinched) at the interface between the watch body and watch band 1412, thereby preventing user discomfort.

Watch band 1412 may include a first profile 1432 between watch band 1412 and the watch body along an inside perimeter edge (e.g., bottom side perimeter edge) of watch band 1412. The watch body and watch band 1412 may not be in contact with each other along the first profile when the watch body is coupled to watch band 1412. Watch band 1412 may also include a second profile 1430 between watch band 1412 and the watch body along an inside perimeter edge, on the opposite side (e.g., top side) of watch band 1412 that includes first profile 1432. The watch body and watch band 1412 may be in contact with each other along at least a portion of the second profile when the watch body is coupled to watch band 1412.

In some embodiments, first profile 1432 may be concentric (e.g., may have a same shape) relative to an adjacent surface of the watch body coupled to watch band 1412. In contrast, second profile 1430 may be non-concentric (e.g., may have a different shape) relative to an adjacent surface of the watch body coupled to watch band 1412. For example, second profile 1430 may have one or more inward protrusions that may abut against the watch body when the watch body is coupled to watch band 1412.

FIG. 14B shows a cross-sectional view of watch band 1412 across cutting plane A-A of FIG. 14A. As shown with reference to FIG. 14B, first profile 1432 may be sized and configured such that a substantially uniform spacing gap 1452 is created between watch body 1404 and watch band 1412 around the entire perimeter of watch band 1412. Spacing gap 1452 may have a width of about 0.1 mm, about 0.2 mm, about 0.3 mm, about 0.4 mm, or more. Spacing gap 1452 disposed between watch body 1404 and watch band 1412 may be sized and configured to prevent a user's arm hair from being trapped (e.g., pinched) at the interface between watch body 1404 and watch band 1412.

FIG. 14C shows a cross-sectional view of watch band 1412 across cutting plane B-B of FIG. 14A. As shown with reference to FIG. 14C, second profile 1430 may be sized and configured such that a non-uniform spacing gap 1450 is created between watch body 1404 and watch band 1412 around the entire perimeter of watch band 1412. Spacing gap 1450 may be smaller in certain regions of second profile 1430 than in other regions. For example, spacing gap 1450 may be 0 mm (e.g., no gap) in corner regions 1460 where one or more inward protrusions may be present. At corner regions 1460, watch body 1404 and watch band 1412 may contact one another when watch body 1404 is coupled to watch band 1412.

By configuring watch body 1404 to contact watch band 1412 in corner regions 1460, the mechanical stability of the watch assembly (e.g., watch body 1404 coupled to watch band 1412) may be increased. In regions of second profile 1430 other than corner regions 1460 (e.g., the side regions), spacing gap 1450 may have a width of about 0.1 mm, about 0.2 mm, about 0.3 mm, about 0.4 mm, or more. Spacing gap 1450 between watch body 1404 and watch band 1412 in regions of second profile 1430 other than corner regions 1460 may be configured to prevent a user's arm hair from being trapped (e.g., pinched) at the interface between watch body 1404 and watch band 1412.

FIG. 15 is a flow diagram illustrating an example method 1500 of offloading a computing task from a head-mounted display to a watch body. At operation 1510, method 1500 may include determining at least one computing task of a head-mounted display (HMD) that is suitable for processing on available computing resources of a watch body. Operation 1510 may be performed in a variety of ways, as will be understood by one skilled in the art considering the present disclosure. The offloaded computing task may be determined based on computing requirements, power consumption, latency requirements, or a combination thereof.

At operation 1520, method 1500 may include selectively offloading the at least one computing task of the HMD that is suitable for processing on the available computing resources of the watch body to the watch body. Operation 1520 may be performed in a variety of ways. For example, the task offloaded from the HMD to the watch body may include an image processing task. Sensors (e.g., image sensors) of the HMD may acquire data that captures images surrounding the HMD. The images may include certain features and/or objects (e.g., people, faces, devices, backgrounds, etc.) of the captured image. The watch body may process these images to subtract, add, and/or enhance the objects before displaying on the HMD and/or a display of the watch body (e.g., display screen 102). In some examples, offloading computing tasks from the HMD to the wristband system may reduce power consumption and/or decrease computing task execution latency in the HMD.

In some examples, the task offloaded from the HMD to the watch body may include a location determining task. Sensors (e.g., LiDAR sensors, radar sensors) and/or receivers (e.g., RF receivers, WiFi receivers, GPS receivers) of the HMD may acquire data that requires processing (e.g., triangulation) in order to determine the location, orientation, and/or position of an object relative to the HMD (e.g., a 3D location of the HMD relative to the watch body). The data acquired by the HMD may be transmitted to the watch body for processing. The watch body may execute the location determining task by processing the data and returning the resultant location of the object to the HMD. In some examples, the task offloaded from the HMD to the watch body may include a neural network processing task. For example, data acquired by sensors of the HMD (e.g., neuromuscular sensors disposed on a surface of an HMD strap contacting the user's head) may require processing in order to train a neural network (e.g., a recurrent neural network, a long short term memory network, a convolutional neural network) to accurately predict an event. The data acquired by the HMD may be transmitted to the watch body for processing. The watch body may train the neural network using the acquired and return a trained model to the HMD.

In some examples, the task offloaded from the HMD to the watch body may include a graphics processing task. For example, graphics data of an artificial-reality application (e.g., a gaming application) running on the HMD may require processing in order to properly render on the HMD. At least a portion of the graphics data may be transmitted to the watch body for processing. The watch body may process the graphics data (e.g., execute a rendering algorithm) and return the processed graphics data to the HMD and/or display an image based on the processed graphics data on a display of the watch body (e.g., display screen 102).

At operation 1530, method 1500 may include processing, by the available computing resources of the watch body, the at least one computing task. Operation 1530 may be performed in a variety of ways. For example, the at least one computing task may be performed using processor(s) and memory of the watch body such as those described above with reference to FIG. 3.

At operation 1540, method 1500 may include sending results of the processed at least one computing task to the HMD. For example, the watch band may transmit the results to the HMD using a wireless communication method.

As described in detail above, the present disclosure details systems, devices, and methods related to a wristband system that includes a watch body that detachably couples to a watch band. The watch body may decouple from the watch band in order to reduce an encumbrance to a user wearing the watch band. The wristband system may have a split architecture that allows the watch band and the watch body to operate both independently and in communication with one another. For example, the watch band may independently acquire sensor data (e.g., neuromuscular sensor data) when the watch body is detached and transmit that data to the watch body. The mechanical architecture may include a coupling mechanism on the watch band and/or the watch body that allows a user to conveniently attach and detach the watch body from the watch band. The watch body may modify a function based on whether the watch body is coupled or decoupled from the watch band.

In some embodiments, one or more objects (e.g., data associated with sensors, and/or activity information) of a computing system may be associated with one or more privacy settings. These objects may be stored on or otherwise associated with any suitable computing system or application, such as, for example, a social-networking system, a client system, a third-party system, a messaging application, a photo-sharing application, a biometric data acquisition application, an artificial-reality application, and/or any other suitable computing system or application.

Privacy settings (or "access settings") for an object may be stored in any suitable manner; such as, for example, in association with the object, in an index on an authorization server, in another suitable manner, or any suitable combination thereof. A privacy setting for an object may specify how the object (or particular information associated with the object) can be accessed, stored, or otherwise used (e.g., viewed, shared, modified, copied, executed, surfaced, or identified) within an application (such as an artificial-reality application). When privacy settings for an object allow a particular user or other entity to access that object, the object may be described as being "visible" with respect to that user or other entity. As an example, a user of an artificial-reality application may specify privacy settings for a user-profile page that identify a set of users that may access the artificial-reality application information on the user-profile page, thus excluding other users from accessing that information. As another example, an artificial-reality application may store privacy policies/guidelines. The privacy policies/guidelines may specify what information of users may be accessible by which entities and/or by which processes (e.g., internal research, advertising algorithms, machine-learning algorithms), thus ensuring only certain information of the user may be accessed by certain entities or processes.

In some embodiments, privacy settings for an object may specify a "blocked list" of users or other entities that should not be allowed to access certain information associated with the object. In some cases, the blocked list may include third-party entities. The blocked list may specify one or more users or entities for which an object is not visible.

Privacy settings associated with an object may specify any suitable granularity of permitted access or denial of access. As an example, access or denial of access may be specified for particular users (e.g., only me, my roommates, my boss), users within a particular degree-of-separation (e.g., friends, friends-of-friends), user groups (e.g., the gaming club, my family), user networks (e.g., employees of particular employers, students or alumni of particular university), all users ("public"), no users ("private"), users of third-party systems, particular applications (e.g., third-party applications, external websites), other suitable entities, or any suitable combination thereof. In some embodiments, different objects of the same type associated with a user may have different privacy settings. In addition, one or more default privacy settings may be set for each object of a particular object-type.

Embodiments of the present disclosure may include or be implemented in conjunction with various types of artificial-reality systems. Artificial reality is a form of reality that has been adjusted in some manner before presentation to a user, which may include, for example, a virtual reality, an augmented reality, a mixed reality, a hybrid reality, or some combination and/or derivative thereof. Artificial-reality content may include completely computer-generated content or computer-generated content combined with captured (e.g., real-world) content. The artificial-reality content may include video, audio, haptic feedback, or some combination thereof, any of which may be presented in a single channel or in multiple channels (such as stereo video that produces a three-dimensional (3D) effect to the viewer). Additionally, in some embodiments, artificial reality may also be associated with applications, products, accessories, services, or some combination thereof, that are used to, for example, create content in an artificial reality and/or are otherwise used in (e.g., to perform activities in) an artificial reality.

Artificial-reality systems may be implemented in a variety of different form factors and configurations. Some artificial-reality systems may be designed to work without near-eye displays (NEDs). Other artificial-reality systems may include an NED that also provides visibility into the real world (such as, e.g., augmented-reality system 1600 in FIG. 16) or that visually immerses a user in an artificial reality (such as, e.g., virtual-reality system 1700 in FIG. 17). While some artificial-reality devices may be self-contained systems, other artificial-reality devices may communicate and/or coordinate with external devices to provide an artificial-reality experience to a user. Examples of such external devices include handheld controllers, mobile devices, desktop computers, devices worn by a user, devices worn by one or more other users, and/or any other suitable external system.

Turning to FIG. 16, augmented-reality system 1600 may include an eyewear device 1602 with a frame 1610 configured to hold a left display device 1615(A) and a right display device 1615(B) in front of a user's eyes. Display devices 1615(A) and 1615(B) may act together or independently to present an image or series of images to a user. While augmented-reality system 1600 includes two displays, embodiments of this disclosure may be implemented in augmented-reality systems with a single NED or more than two NEDs.

In some embodiments, augmented-reality system 1600 may include one or more sensors, such as sensor 1640. Sensor 1640 may generate measurement signals in response to motion of augmented-reality system 1600 and may be located on substantially any portion of frame 1610. Sensor 1640 may represent one or more of a variety of different sensing mechanisms, such as a position sensor, an inertial measurement unit (IMU), a depth camera assembly, a structured light emitter and/or detector, or any combination thereof. In some embodiments, augmented-reality system 1600 may or may not include sensor 1640 or may include more than one sensor. In embodiments in which sensor 1640 includes an IMU, the IMU may generate calibration data based on measurement signals from sensor 1640. Examples of sensor 1640 may include, without limitation, accelerometers, gyroscopes, magnetometers, other suitable types of sensors that detect motion, sensors used for error correction of the IMU, or some combination thereof.

In some examples, augmented-reality system 1600 may also include a microphone array with a plurality of acoustic transducers 1620(A)-1620(J), referred to collectively as acoustic transducers 1620. Acoustic transducers 1620 may represent transducers that detect air pressure variations induced by sound waves. Each acoustic transducer 1620 may be configured to detect sound and convert the detected sound into an electronic format (e.g., an analog or digital format). The microphone array in FIG. 16 may include, for example, ten acoustic transducers: 1620(A) and 1620(B), which may be designed to be placed inside a corresponding ear of the user, acoustic transducers 1620(C), 1620(D), 1620(E), 1620(F), 1620(G), and 1620(H), which may be positioned at various locations on frame 1610, and/or acoustic transducers 1620(I) and 1620(J), which may be positioned on a corresponding neckband 1605.

In some embodiments, one or more of acoustic transducers 1620(A)-(J) may be used as output transducers (e.g., speakers). For example, acoustic transducers 1620(A) and/or 1620(B) may be earbuds or any other suitable type of headphone or speaker.

The configuration of acoustic transducers 1620 of the microphone array may vary. While augmented-reality system 1600 is shown in FIG. 16 as having ten acoustic transducers 1620, the number of acoustic transducers 1620 may be greater or less than ten. In some embodiments, using higher numbers of acoustic transducers 1620 may increase the amount of audio information collected and/or the sensitivity and accuracy of the audio information. In contrast, using a lower number of acoustic transducers 1620 may decrease the computing power required by an associated controller 1650 to process the collected audio information. In addition, the position of each acoustic transducer 1620 of the microphone array may vary. For example, the position of an acoustic transducer 1620 may include a defined position on the user, a defined coordinate on frame 1610, an orientation associated with each acoustic transducer 1620, or some combination thereof.

Acoustic transducers 1620(A) and 1620(B) may be positioned on different parts of the user's ear, such as behind the pinna, behind the tragus, and/or within the auricle or fossa. Or, there may be additional acoustic transducers 1620 on or surrounding the ear in addition to acoustic transducers 1620 inside the ear canal. Having an acoustic transducer 1620 positioned next to an ear canal of a user may enable the microphone array to collect information on how sounds arrive at the ear canal. By positioning at least two of acoustic transducers 1620 on either side of a user's head (e.g., as binaural microphones), augmented-reality device 1600 may simulate binaural hearing and capture a 3D stereo sound field around about a user's head. In some embodiments, acoustic transducers 1620(A) and 1620(B) may be connected to augmented-reality system 1600 via a wired connection 1630, and in other embodiments acoustic transducers 1620(A) and 1620(B) may be connected to augmented-reality system 1600 via a wireless connection (e.g., a Bluetooth connection). In still other embodiments, acoustic transducers 1620(A) and 1620(B) may not be used at all in conjunction with augmented-reality system 1600.

Acoustic transducers 1620 on frame 1610 may be positioned in a variety of different ways, including along the length of the temples, across the bridge, above or below display devices 1615(A) and 1615(B), or some combination thereof. Acoustic transducers 1620 may also be oriented such that the microphone array is able to detect sounds in a wide range of directions surrounding the user wearing the augmented-reality system 1600. In some embodiments, an optimization process may be performed during manufacturing of augmented-reality system 1600 to determine relative positioning of each acoustic transducer 1620 in the microphone array.

In some examples, augmented-reality system 1600 may include or be connected to an external device (e.g., a paired device), such as neckband 1605. Neckband 1605 generally represents any type or form of paired device. Thus, the following discussion of neckband 1605 may also apply to various other paired devices, such as charging cases, smart watches, smart phones, wrist bands, other wearable devices, hand-held controllers, tablet computers, laptop computers, other external compute devices, etc.

As shown, neckband 1605 may be coupled to eyewear device 1602 via one or more connectors. The connectors may be wired or wireless and may include electrical and/or non-electrical (e.g., structural) components. In some cases, eyewear device 1602 and neckband 1605 may operate independently without any wired or wireless connection between them. While FIG. 16 illustrates the components of eyewear device 1602 and neckband 1605 in example locations on eyewear device 1602 and neckband 1605, the components may be located elsewhere and/or distributed differently on eyewear device 1602 and/or neckband 1605. In some embodiments, the components of eyewear device 1602 and neckband 1605 may be located on one or more additional peripheral devices paired with eyewear device 1602, neckband 1605, or some combination thereof.

Pairing external devices, such as neckband 1605, with augmented-reality eyewear devices may enable the eyewear devices to achieve the form factor of a pair of glasses while still providing sufficient battery and computation power for expanded capabilities. Some or all of the battery power, computational resources, and/or additional features of augmented-reality system 1600 may be provided by a paired device or shared between a paired device and an eyewear device, thus reducing the weight, heat profile, and form factor of the eyewear device overall while still retaining desired functionality. For example, neckband 1605 may allow components that would otherwise be included on an eyewear device to be included in neckband 1605 since users may tolerate a heavier weight load on their shoulders than they would tolerate on their heads. Neckband 1605 may also have a larger surface area over which to diffuse and disperse heat to the ambient environment. Thus, neckband 1605 may allow for greater battery and computation capacity than might otherwise have been possible on a stand-alone eyewear device. Since weight carried in neckband 1605 may be less invasive to a user than weight carried in eyewear device 1602, a user may tolerate wearing a lighter eyewear device and carrying or wearing the paired device for greater lengths of time than a user would tolerate wearing a heavy stand-alone eyewear device, thereby enabling users to more fully incorporate artificial-reality environments into their day-to-day activities.

Neckband 1605 may be communicatively coupled with eyewear device 1602 and/or to other devices. These other devices may provide certain functions (e.g., tracking, localizing, depth mapping, processing, storage, etc.) to augmented-reality system 1600. In the embodiment of FIG. 16, neckband 1605 may include two acoustic transducers (e.g., 1620(I) and 1620(J)) that are part of the microphone array (or potentially form their own microphone subarray). Neckband 1605 may also include a controller 1625 and a power source 1635.

Acoustic transducers 1620(I) and 1620(J) of neckband 1605 may be configured to detect sound and convert the detected sound into an electronic format (analog or digital). In the embodiment of FIG. 16, acoustic transducers 1620(I) and 1620(J) may be positioned on neckband 1605, thereby increasing the distance between the neckband acoustic transducers 1620(I) and 1620(J) and other acoustic transducers 1620 positioned on eyewear device 1602. In some cases, increasing the distance between acoustic transducers 1620 of the microphone array may improve the accuracy of beamforming performed via the microphone array. For example, if a sound is detected by acoustic transducers 1620(C) and 1620(D) and the distance between acoustic transducers 1620(C) and 1620(D) is greater than, e.g., the distance between acoustic transducers 1620(D) and 1620(E), the determined source location of the detected sound may be more accurate than if the sound had been detected by acoustic transducers 1620(D) and 1620(E).

Controller 1625 of neckband 1605 may process information generated by the sensors on neckband 1605 and/or augmented-reality system 1600. For example, controller 1625 may process information from the microphone array that describes sounds detected by the microphone array. For each detected sound, controller 1625 may perform a direction-of-arrival (DOA) estimation to estimate a direction from which the detected sound arrived at the microphone array. As the microphone array detects sounds, controller 1625 may populate an audio data set with the information. In embodiments in which augmented-reality system 1600 includes an inertial measurement unit, controller 1625 may compute all inertial and spatial calculations from the IMU located on eyewear device 1602. A connector may convey information between augmented-reality system 1600 and neckband 1605 and between augmented-reality system 1600 and controller 1625. The information may be in the form of optical data, electrical data, wireless data, or any other transmittable data form. Moving the processing of information generated by augmented-reality system 1600 to neckband 1605 may reduce weight and heat in eyewear device 1602, making it more comfortable to the user.

Power source 1635 in neckband 1605 may provide power to eyewear device 1602 and/or to neckband 1605. Power source 1635 may include, without limitation, lithium ion batteries, lithium-polymer batteries, primary lithium batteries, alkaline batteries, or any other form of power storage. In some cases, power source 1635 may be a wired power source. Including power source 1635 on neckband 1605 instead of on eyewear device 1602 may help better distribute the weight and heat generated by power source 1635.

As noted, some artificial-reality systems may, instead of blending an artificial reality with actual reality, substantially replace one or more of a user's sensory perceptions of the real world with a virtual experience. One example of this type of system is a head-worn display system, such as virtual-reality system 1700 in FIG. 17, that mostly or completely covers a user's field of view. Virtual-reality system 1700 may include a front rigid body 1702 and a band 1704 shaped to fit around a user's head. Virtual-reality system 1700 may also include output audio transducers 1706(A) and 1706(B). Furthermore, while not shown in FIG. 17, front rigid body 1702 may include one or more electronic elements, including one or more electronic displays, one or more inertial measurement units (IMUS), one or more tracking emitters or detectors, and/or any other suitable device or system for creating an artificial-reality experience.

Artificial-reality systems may include a variety of types of visual feedback mechanisms. For example, display devices in augmented-reality system 1600 and/or virtual-reality system 1700 may include one or more liquid crystal displays (LCDs), light emitting diode (LED) displays, organic LED (OLED) displays, digital light project (DLP) micro-displays, liquid crystal on silicon (LCoS) micro-displays, and/or any other suitable type of display screen. These artificial-reality systems may include a single display screen for both eyes or may provide a display screen for each eye, which may allow for additional flexibility for varifocal adjustments or for correcting a user's refractive error. Some of these artificial-reality systems may also include optical subsystems having one or more lenses (e.g., conventional concave or convex lenses, Fresnel lenses, adjustable liquid lenses, etc.) through which a user may view a display screen. These optical subsystems may serve a variety of purposes, including to collimate (e.g., make an object appear at a greater distance than its physical distance), to magnify (e.g., make an object appear larger than its actual size), and/or to relay (to, e.g., the viewer's eyes) light. These optical subsystems may be used in a non-pupil-forming architecture (such as a single lens configuration that directly collimates light but results in so-called pincushion distortion) and/or a pupil-forming architecture (such as a multi-lens configuration that produces so-called barrel distortion to nullify pincushion distortion).

In addition to or instead of using display screens, some of the artificial-reality systems described herein may include one or more projection systems. For example, display devices in augmented-reality system 1600 and/or virtual-reality system 1700 may include micro-LED projectors that project light (using, e.g., a waveguide) into display devices, such as clear combiner lenses that allow ambient light to pass through. The display devices may refract the projected light toward a user's pupil and may enable a user to simultaneously view both artificial-reality content and the real world. The display devices may accomplish this using any of a variety of different optical components, including waveguide components (e.g., holographic, planar, diffractive, polarized, and/or reflective waveguide elements), light-manipulation surfaces and elements (such as diffractive, reflective, and refractive elements and gratings), coupling elements, etc. Artificial-reality systems may also be configured with any other suitable type or form of image projection system, such as retinal projectors used in virtual retina displays.

The artificial-reality systems described herein may also include various types of computer vision components and subsystems. For example, augmented-reality system 1600 and/or virtual-reality system 1700 may include one or more optical sensors, such as two-dimensional (2D) or 3D cameras, structured light transmitters and detectors, time-of-flight depth sensors, single-beam or sweeping laser rangefinders, 3D LiDAR sensors, and/or any other suitable type or form of optical sensor. An artificial-reality system may process data from one or more of these sensors to identify a location of a user, to map the real world, to provide a user with context about real-world surroundings, and/or to perform a variety of other functions.

The artificial-reality systems described herein may also include one or more input and/or output audio transducers. Output audio transducers may include voice coil speakers, ribbon speakers, electrostatic speakers, piezoelectric speakers, bone conduction transducers, cartilage conduction transducers, tragus-vibration transducers, and/or any other suitable type or form of audio transducer. Similarly, input audio transducers may include condenser microphones, dynamic microphones, ribbon microphones, and/or any other type or form of input transducer. In some embodiments, a single transducer may be used for both audio input and audio output.

In some embodiments, the artificial-reality systems described herein may also include tactile (e.g., haptic) feedback systems, which may be incorporated into headwear, gloves, body suits, handheld controllers, environmental devices (e.g., chairs, floormats, etc.), and/or any other type of device or system. Haptic feedback systems may provide various types of cutaneous feedback, including vibration, force, traction, texture, and/or temperature. Haptic feedback systems may also provide various types of kinesthetic feedback, such as motion and compliance. Haptic feedback may be implemented using motors, piezoelectric actuators, fluidic systems, and/or a variety of other types of feedback mechanisms. Haptic feedback systems may be implemented independent of other artificial-reality devices, within other artificial-reality devices, and/or in conjunction with other artificial-reality devices.

By providing haptic sensations, audible content, and/or visual content, artificial-reality systems may create an entire virtual experience or enhance a user's real-world experience in a variety of contexts and environments. For instance, artificial-reality systems may assist or extend a user's perception, memory, or cognition within a particular environment. Some systems may enhance a user's interactions with other people in the real world or may enable more immersive interactions with other people in a virtual world. Artificial-reality systems may also be used for educational purposes (e.g., for teaching or training in schools, hospitals, government organizations, military organizations, business enterprises, etc.), entertainment purposes (e.g., for playing video games, listening to music, watching video content, etc.), and/or for accessibility purposes (e.g., as hearing aids, visual aids, etc.). The embodiments disclosed herein may enable or enhance a user's artificial-reality experience in one or more of these contexts and environments and/or in other contexts and environments.

As noted, artificial-reality systems 1600 and 1700 may be used with a variety of other types of devices to provide a more compelling artificial-reality experience. These devices may be haptic interfaces with transducers that provide haptic feedback and/or that collect haptic information about a user's interaction with an environment. The artificial-reality systems disclosed herein may include various types of haptic interfaces that detect or convey various types of haptic information, including tactile feedback (e.g., feedback that a user detects via nerves in the skin, which may also be referred to as cutaneous feedback) and/or kinesthetic feedback (e.g., feedback that a user detects via receptors located in muscles, joints, and/or tendons).

Figure 18:
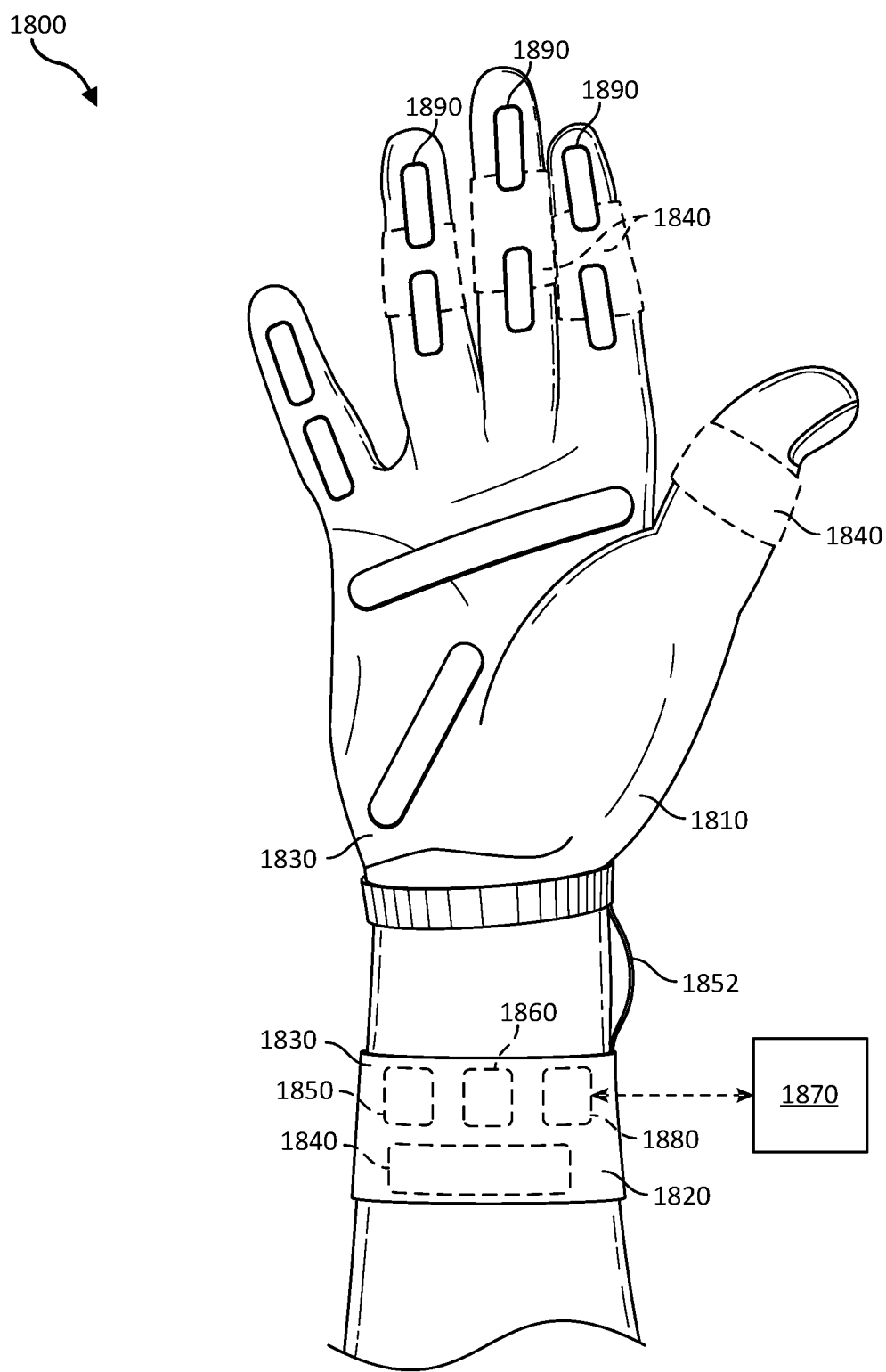
FIG. 18 is an illustration of exemplary haptic devices that may be used in connection with embodiments of this disclosure.

Haptic feedback may be provided by interfaces positioned within a user's environment (e.g., chairs, tables, floors, etc.) and/or interfaces on articles that may be worn or carried by a user (e.g., gloves, wristbands, etc.). As an example, FIG. 18 illustrates a vibrotactile system 1800 in the form of a wearable glove (haptic device 1810) and wristband (haptic device 1820). Haptic device 1810 and haptic device 1820 are shown as examples of wearable devices that include a flexible, wearable textile material 1830 that is shaped and configured for positioning against a user's hand and wrist, respectively. This disclosure also includes vibrotactile systems that may be shaped and configured for positioning against other human body parts, such as a finger, an arm, a head, a torso, a foot, or a leg. By way of example and not limitation, vibrotactile systems according to various embodiments of the present disclosure may also be in the form of a glove, a headband, an armband, a sleeve, a head covering, a sock, a shirt, or pants, among other possibilities. In some examples, the term "textile" may include any flexible, wearable material, including woven fabric, non-woven fabric, leather, cloth, a flexible polymer material, composite materials, etc.

One or more vibrotactile devices 1840 may be positioned at least partially within one or more corresponding pockets formed in textile material 1830 of vibrotactile system 1800. Vibrotactile devices 1840 may be positioned in locations to provide a vibrating sensation (e.g., haptic feedback) to a user of vibrotactile system 1800. For example, vibrotactile devices 1840 may be positioned against the user's finger(s), thumb, or wrist, as shown in FIG. 18. Vibrotactile devices 1840 may, in some examples, be sufficiently flexible to conform to or bend with the user's corresponding body part(s).

A power source 1850 (e.g., a battery) for applying a voltage to the vibrotactile devices 1840 for activation thereof may be electrically coupled to vibrotactile devices 1840, such as via conductive wiring 1852. In some examples, each of vibrotactile devices 1840 may be independently electrically coupled to power source 1850 for individual activation. In some embodiments, a processor 1860 may be operatively coupled to power source 1850 and configured (e.g., programmed) to control activation of vibrotactile devices 1840.

Vibrotactile system 1800 may be implemented in a variety of ways. In some examples, vibrotactile system 1800 may be a standalone system with integral subsystems and components for operation independent of other devices and systems. As another example, vibrotactile system 1800 may be configured for interaction with another device or system 1870. For example, vibrotactile system 1800 may, in some examples, include a communications interface 1880 for receiving and/or sending signals to the other device or system 1870. The other device or system 1870 may be a mobile device, a gaming console, an artificial-reality (e.g., virtual-reality, augmented-reality, mixed-reality) device, a personal computer, a tablet computer, a network device (e.g., a modem, a router, etc.), a handheld controller, etc. Communications interface 1880 may enable communications between vibrotactile system 1800 and the other device or system 1870 via a wireless (e.g., Wi-Fi, Bluetooth, cellular, radio, etc.) link or a wired link. If present, communications interface 1880 may be in communication with processor 1860, such as to provide a signal to processor 1860 to activate or deactivate one or more of the vibrotactile devices 1840.

Vibrotactile system 1800 may optionally include other subsystems and components, such as touch-sensitive pads 1890, pressure sensors, motion sensors, position sensors, lighting elements, and/or user interface elements (e.g., an on/off button, a vibration control element, etc.). During use, vibrotactile devices 1840 may be configured to be activated for a variety of different reasons, such as in response to the user's interaction with user interface elements, a signal from the motion or position sensors, a signal from the touch-sensitive pads 1890, a signal from the pressure sensors, a signal from the other device or system 1870, etc.

Although power source 1850, processor 1860, and communications interface 1880 are illustrated in FIG. 18 as being positioned in haptic device 1820, the present disclosure is not so limited. For example, one or more of power source 1850, processor 1860, or communications interface 1880 may be positioned within haptic device 1810 or within another wearable textile.

Haptic wearables, such as those shown in and described in connection with FIG. 18, may be implemented in a variety of types of artificial-reality systems and environments. FIG. 19 shows an example artificial-reality environment 1900 including one head-mounted virtual-reality display and two haptic devices (e.g., gloves), and in other embodiments any number and/or combination of these components and other components may be included in an artificial-reality system. For example, in some embodiments there may be multiple head-mounted displays each having an associated haptic device, with each head-mounted display and each haptic device communicating with the same console, portable computing device, or other computing system.

Head-mounted display 1902 generally represents any type or form of virtual-reality system, such as virtual-reality system 1700 in FIG. 17. Haptic device 1904 generally represents any type or form of wearable device, worn by a user of an artificial-reality system, that provides haptic feedback to the user to give the user the perception that he or she is physically engaging with a virtual object. In some embodiments, haptic device 1904 may provide haptic feedback by applying vibration, motion, and/or force to the user.

For example, haptic device 1904 may limit or augment a user's movement. To give a specific example, haptic device 1904 may limit a user's hand from moving forward so that the user has the perception that his or her hand has come in physical contact with a virtual wall. In this specific example, one or more actuators within the haptic device may achieve the physical-movement restriction by pumping fluid into an inflatable bladder of the haptic device. In some examples, a user may also use haptic device 1904 to send action requests to a console. Examples of action requests include, without limitation, requests to start an application and/or end the application and/or requests to perform a particular action within the application.

While haptic interfaces may be used with virtual-reality systems, as shown in FIG. 19, haptic interfaces may also be used with augmented-reality systems, as shown in FIG. 20. FIG. 20 is a perspective view of a user 2010 interacting with an augmented-reality system 2000. In this example, user 2010 may wear a pair of augmented-reality glasses 2020 that may have one or more displays 2022 and that are paired with a haptic device 2030. In this example, haptic device 2030 may be a wristband that includes a plurality of band elements 2032 and a tensioning mechanism 2034 that connects band elements 2032 to one another.

One or more of band elements 2032 may include any type or form of actuator suitable for providing haptic feedback. For example, one or more of band elements 2032 may be configured to provide one or more of various types of cutaneous feedback, including vibration, force, traction, texture, and/or temperature. To provide such feedback, band elements 2032 may include one or more of various types of actuators. In one example, each of band elements 2032 may include a vibrotactor (e.g., a vibrotactile actuator) configured to vibrate in unison or independently to provide one or more of various types of haptic sensations to a user. Alternatively, only a single band element or a subset of band elements may include vibrotactors.

Haptic devices 1810, 1820, 1904, and 2030 may include any suitable number and/or type of haptic transducer, sensor, and/or feedback mechanism. For example, haptic devices 1810, 1820, 1904, and 2030 may include one or more mechanical transducers, piezoelectric transducers, and/or fluidic transducers. Haptic devices 1810, 1820, 1904, and 2030 may also include various combinations of different types and forms of transducers that work together or independently to enhance a user's artificial-reality experience. In one example, each of band elements 2032 of haptic device 2030 may include a vibrotactor (e.g., a vibrotactile actuator) configured to vibrate in unison or independently to provide one or more of various types of haptic sensations to a user.

Figure 21A:
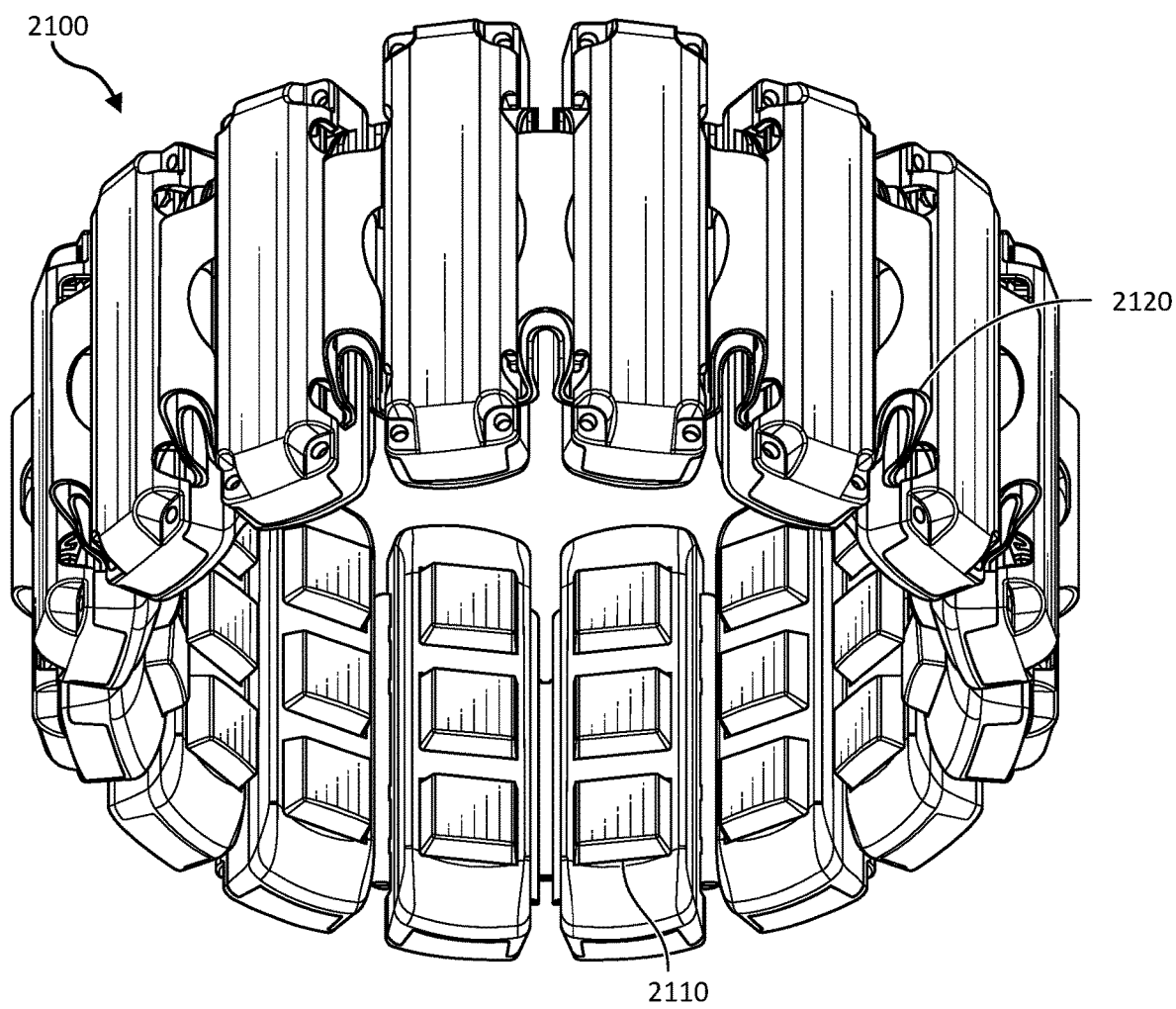
FIGS. 21A and 21B are illustrations of an exemplary human-machine interface configured to be worn around a user's lower arm or wrist.
Figure 21B:
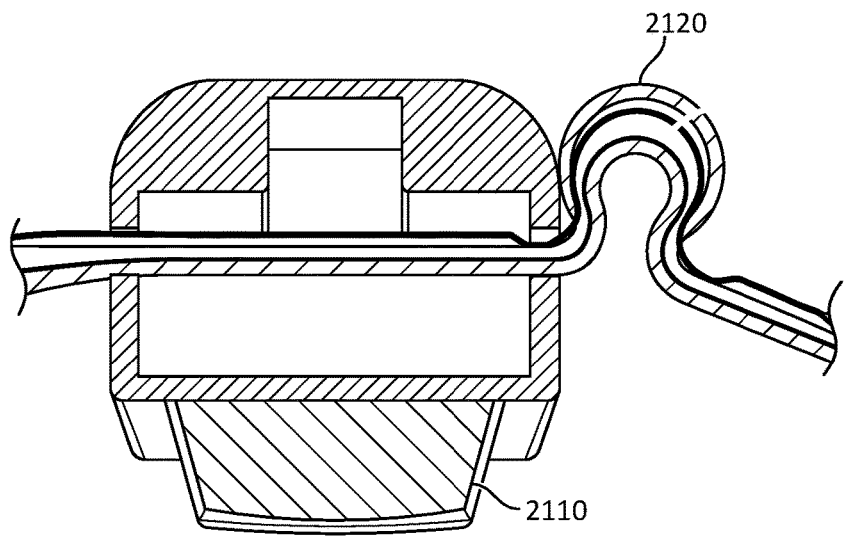

FIG. 21A illustrates an exemplary human-machine interface (also referred to herein as an EMG control interface) configured to be worn around a user's lower arm or wrist as a wearable system 900. In this example, wearable system 2100 may include sixteen neuromuscular sensors 2110 (e.g., EMG sensors) arranged circumferentially around an elastic band 2120. However, any suitable number of neuromuscular sensors may be used. The number and arrangement of neuromuscular sensors may depend on the particular application for which the wearable device is used. For example, a wearable armband or wristband may be used to generate control information for controlling an augmented reality system, a robot, controlling a vehicle, scrolling through text, controlling a virtual avatar, or any other suitable control task. As shown, the sensors may be coupled together using flexible electronics incorporated into the wireless device. FIG. 21B illustrates a cross-sectional view through one of the sensors of the wearable device shown in FIG. 21A. In some embodiments, the output of one or more of the sensing components may be optionally processed using hardware signal processing circuitry (e.g., to perform amplification, filtering, and/or rectification). In other embodiments, at least some signal processing of the output of the sensing components may be performed in software. Thus, signal processing of signals sampled by the sensors may be performed in hardware, software, or by any suitable combination of hardware and software, as aspects of the technology described herein are not limited in this respect. A non-limiting example of a signal processing chain used to process recorded data from sensors 2110 is discussed in more detail below with reference to FIGS. 22A and 22B.

FIGS. 22A and 22B illustrate an exemplary schematic diagram with internal components of a wearable system with EMG sensors. As shown, the wearable system may include a wearable portion 2210 (FIG. 22A) and a dongle portion 2220 (FIG. 22B) in communication with the wearable portion 2210 (e.g., via BLUETOOTH or another suitable wireless communication technology). As shown in FIG. 22A, the wearable portion 2210 includes sensors 2110, examples of which are described in connection with FIGS. 21A and 21B. The output of the sensors 2110 is provided to analog front end 2230, which may be configured to perform analog processing (e.g., amplification, noise reduction, filtering, etc.) on the recorded signals. The processed analog signals are then provided to analog-to-digital converter 2232, which may convert the analog signals to digital signals that may be processed by one or more computer processors. An example of a computer processor that may be used in accordance with some embodiments is microcontroller (MCU) 2234, illustrated in FIG. 22A. As shown, MCU 2234 may also include inputs from other sensors (e.g., IMU sensor 2240), and power and battery module 2242. The output of the processing performed by MCU may be provided to antenna 2250 for transmission to dongle portion 2220 shown in FIG. 22B.

Dongle portion 2220 includes antenna 2252 configured to communicate with antenna 2250 included as part of wearable portion 2210. Communication between antenna 2250 and 2252 may occur using any suitable wireless technology and protocol, non-limiting examples of which include radiofrequency signaling and BLUETOOTH. As shown, the signals received by antenna 2252 of dongle portion 2220 may be provided to a host computer for further processing, display, and/or for effecting control of a particular physical or virtual object or objects.

Although the examples provided with reference to FIGS. 21A-21B and FIGS. 22A-22B are discussed in the context of interfaces with EMG sensors, the techniques described herein for reducing electromagnetic interference may also be implemented in wearable interfaces with other types of sensors including, but not limited to, mechanomyography (MMG) sensors, sonomyography (SMG) sensors, and electrical impedance tomography (EIT) sensors. The techniques described herein for reducing electromagnetic interference may also be implemented in wearable interfaces that communicate with computer hosts through wires and cables (e.g., USB cables, optical fiber cables, etc.).

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware or with one or more processors programmed using microcode or software to perform the functions recited above.

In this respect, it should be appreciated that one implementation of the embodiments of the present invention comprises at least one non-transitory computer readable storage medium (e.g., a computer memory, a portable memory, a compact disk, etc.) encoded with a computer program (e.g., a plurality of instructions), that, when executed on a processor, performs the above-discussed functions of the embodiments of the present invention. The computer-readable storage medium can be transportable such that the program stored thereon can be loaded onto any computer resource to implement the aspects of the present invention discussed herein. In addition, it should be appreciated that the reference to a computer program that, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of that an example has been provided. The acts performed as part of the method(s) may be ordered in any suitable way. Accordingly, embodiments may be constructed in that acts are performed in an order different than illustrated, that may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in that acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing," "involving," and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting.

By way of non-limiting examples, the following embodiments are included in the present disclosure.

Example 1: A system comprising a watch band, a watch body comprising at least one image sensor configured to capture a wide-angle image, a coupling mechanism configured to detachably couple the watch body to the watch band, and at least one biometric sensor on at least one of the watch band or the watch body.

Example 2: The system of Example 1, wherein the watch body is configured to operate independently from the watch band, and the watch body and the watch band are configured to communicate with each other.

Example 3: The system of Example 1 or Example 2, wherein a level of functionality of at least one of the watch band or the watch body is modified when the watch body is detached from the watch band.

Example 4: The system of any of Examples 1 through 3, wherein the wide-angle image comprises a plurality of images stitched together from a plurality of image sensors of the watch body.

Example 5: The system of any of Examples 1 through 4, wherein the system is configured to determine an orientation of a display of the watch body relative to an eye gaze direction of a user and orient content viewed on the display to the eye gaze direction of the user.

Example 6: The system of any of Examples 1 through 5, further comprising a head-mounted display, wherein the watch body is communicatively coupled to the head-mounted display and the head-mounted display is configured to display at least a portion of the captured image.

Example 7: The system of Example 6, further comprising at least one neuromuscular sensor, wherein the watch body is configured to transmit data captured by the at least one neuromuscular sensor to the head-mounted display and the data captured by the at least one neuromuscular sensor comprises a muscle intention of a user.

Example 8: The system of Example 7, wherein the head-mounted display is configured to enhance a user interaction with an object within an artificial-reality environment based on the muscle intention.

Example 9: The system of any of Examples 1 through 8, wherein the head-mounted display is configured to enhance a user interaction with an object within an artificial-reality environment based on the muscle intention.

Example 10: The system of any of Examples 1 through 9, further comprising a head-mounted display, wherein the watch band further comprises a haptic actuator that is configured to provide haptic feedback to a user based on at least one of instructions from the watch body or instructions from the head-mounted display.

Example 11: The system of any of Examples 1 through 10, wherein the coupling mechanism is configured to couple the watch body to the watch band by application of at least one of a substantially linear force to the watch body towards the watch band in a first direction or a substantially rotational force to the watch body relative to the watch band in a second direction and decouple the watch body from the watch band by application of at least one of a substantially linear force to the watch body towards the watch band in a third direction opposite the first direction or a substantially rotational force to the watch body relative to the watch band in a fourth direction opposite the second direction.

Example 12: The system of any of Examples 1 through 11, wherein the coupling mechanism comprises at least one spring-loaded button disposed on the watch body, at least one first magnet disposed on the watch body, at least one second magnet disposed on the watch band, wherein a magnetic attraction between the at least one first magnet and the at least one second magnet aligns the watch body relative to the watch band prior to coupling the watch body to the watch band, and at least one pin configured to retract and to decouple the watch body from the watch band as a result of pressing the at least one spring-loaded button.

Example 13: The system of any of Examples 1 through 12, wherein the coupling mechanism comprises at least one spring-loaded button disposed on the watch body, wherein pressing the at least one spring-loaded button is configured to cause at least one of modifying a function of the watch body or decoupling the watch body from the watch band.

Example 14: The system of any of Examples 1 through 13, wherein the watch band comprises a first profile between the watch body and the watch band along a first perimeter edge of the watch band and a second profile between the watch body and the watch band along a second perimeter edge of the watch band, wherein the watch body and the watch band are not in contact with each other along the first profile when the watch body is coupled to the watch band and the watch body and the watch band are in contact with each other along at least a portion of the second profile when the watch body is coupled to the watch band.

Example 15: The system of any of Examples 1 through 14, wherein the coupling mechanism comprises at least one first spring configured to apply a radially outward force to at least one first pawl, at least one second spring configured to apply a radially outward force to at least one second pawl, a first angled surface disposed on an upper end of the at least one first pawl that is configured to engage a first lock surface of the watch band to secure the watch body to the watch band in a linear direction, and a second angled surface disposed on a side of the at least one second pawl that is configured to engage a second lock surface of the watch band to secure the watch body to the watch band in a rotational direction.

Example 16: The system of any of Examples 1 through 15, wherein the coupling mechanism is configured to couple the watch body to the watch band by application of a substantially linear force to the watch body towards the watch band and decouple the watch body from the watch band by pressing at least one spring loaded button disposed on the watch body.

Example 17: The system of any of Examples 1 through 16 wherein the coupling mechanism comprises at least one spring-loaded button disposed on the watch body, at least one lock bar configured to shift in position as a result of pressing the at least one spring-loaded button, and at least one pin configured to retract and to decouple the watch body from the watch band as a result of the shifting of the position of the at least one lock bar.

Example 18: The system of any of Examples 1 through 17, wherein the coupling mechanism further comprises a lock bar spring configured to apply a retaining force to the at least one lock bar, and an angled surface on the at least one lock bar configured to transfer the retaining force to the at least one pin, wherein the at least one pin is positioned to transfer the retaining force to the watch band with a force component in a direction to retain the watch body against the watch band.

Example 19: The system of any of Examples 1 through 18, further comprising first electrical contacts disposed on the watch body and complementary second electrical contacts disposed on the watch band, wherein the retaining force maintains an electrical connection between the first electrical contacts and the second electrical contacts when the watch body is coupled to the watch band.

Example 20: A method, comprising determining at least one computing task of a head-mounted display (HMD) that is suitable for processing on available computing resources of a watch body, selectively offloading the at least one computing task of the HMD that is suitable for processing on the available computing resources of the watch body to the watch body, processing, by the available computing resources of the watch body, the at least one computing task, and sending results of the processed at least one computing task to the HMD.

Example 21: The method of Example 20, wherein the at least one computing task comprises at least one of an image processing task, a location determining task, a neural network processing task, or a graphics processing task.

Example 22: The method of Example 20 or Example 21, further comprising reducing a power consumption of the HMD by selectively offloading the at least one computing task of the HMD to the watch body.

Example 23: The method of any of Examples 20 through 22, further comprising reducing heat generated within the HMD by selectively offloading the at least one computing task of the HMD to the watch body.

Example 24: A system comprising a watch band and a watch body detachably coupled to the watch band, the watch body comprising a front face, a rear face opposite the front face, a first image sensor in the front face, and a second image sensor in the rear face, Example 25: The system of Example 21, wherein the second image sensor is disposed adjacent to skin of a user of the wristband system when the watch body is coupled to the watch band and the wristband system is donned by the user, and the second image sensor is configured to acquire a biometric of the user.

Example 26: The system of any of Example 21 or Example 22, wherein the first image sensor is oriented to capture a first wide-angle image in a first direction, the second image sensor is oriented to capture a second wide-angle image in a second direction opposite the first direction, and a processor of the wristband system is configured to stitch the first wide-angle image and the second wide-angle image together to create a seamless panoramic image.

Example 27: The system of any of Examples 21 through 23, wherein the second image sensor is activated in response to the watch body being detached from the watch band.

Example 28: The system of any of Examples 21 through 24, further comprising at least one biometric sensor in the rear face, wherein the biometric sensor is activated in response to the watch body being attached to the watch band.

Example 29: A method, comprising determining at least one computing task of a watch body that is suitable for processing on available computing resources of a head-mounted display (HMD), selectively offloading the at least one computing task of the watch body that is suitable for processing on the available computing resources of the HMD to the HMD, processing, by the available computing resources of the HMD, the at least one computing task, and sending results of the processed at least one computing task to the watch body.

Example 30: A system comprising a wearable device, a head-mounted display (HMD), a smartphone, a server, and an electronic device, wherein the wearable device selectively offloads at least one computing task of the wearable device to available computing resources of at least one of the HMD, the smartphone, the server, or the electronic device.

Example 31: A system comprising a wearable device, a head-mounted display (HMD), a smartphone, a server, and an electronic device, wherein at least one of the HMD, the smartphone, the server, or the electronic device selectively offloads at least one computing task to available computing resources of the wearable device.

Example 32: A non-transitory computer-readable medium encoded with instructions that, when executed by at least one computer processor performs a method of determining at least one computing task of a head-mounted display (HMD) that is suitable for processing on available computing resources of a watch body, selectively offloading the at least one computing task of the HMD that is suitable for processing on the available computing resources of the watch body to the watch body, processing, by the available computing resources of the watch body, the at least one computing task, and sending results of the processed at least one computing task to the HMD.

Example 33: A wearable device, comprising a watch band, a watch body comprising (i) a front face, (ii) a rear face opposite the front face, (iii) a first image sensor in the front face; and (iv) a second image sensor in the rear face, a coupling mechanism configured to detachably couple the watch body to the watch band, and one or more processors, and memory storing one or more programs configured to be executed by the one or more processors, the one or more programs including instructions for detecting, at a first time, that the watch body is coupled to the watch band via the coupling mechanism, in response to detecting that the watch body is coupled to the watch body via the coupling mechanism, permitting activation of the first image sensor by a user, detecting, at a second time, that the watch body is not coupled to the watch band via the coupling mechanism, and in response to detecting that the watch body is not coupled to the watch band via the coupling mechanism, activating the second image sensor without user input.

Example 34: The wearable device of Example 33, wherein the one or more programs further include instructions for not permitting activation of the second image sensor by the user in response to detecting that the watch body is coupled to the watch body via the coupling mechanism.

Example 35: The wearable device of Example 33 or Example 34 further comprising at least one additional sensor coupled to the wrist band, the watch body, or the coupling mechanism, the at least one additional sensor being configured to measure coupling between the watch body is coupled to the watch band, wherein detecting that the watch body is coupled to the watch band comprises evaluating coupling data generated by the at least one additional sensor.

Example 36: The wearable device of any of Examples 3 through 35, further comprising one or more electrical contacts that connect when the watch body is coupled to the watch band, wherein detecting that the watch body is coupled to the watch band comprises detecting a disconnect between the one or more electrical contacts.

Example 37: The wearable device of any of Examples 33 through 36, wherein the one or more programs further include instructions for receiving test image data from the second image sensor, and determining whether the test image data satisfies an image capture criterion, wherein activating the second image sensor is performed in response to determining that the test image data satisfies the image capture criterion.

Example 38: A system, comprising a watch band comprising at least one biometric sensor that is configured to collect biometric information, a watch body comprising at least one image sensor configured to capture a wide-angle image, and a coupling mechanism configured to detachably couple the watch body to the watch band.

Example 39: The system of Example 38, wherein the watch body is configured to operate independently from the watch band, the watch band is configured to operate independently from the watch body, and the watch body and the watch band are configured to communicate with each other.

Example 40: The system of Example 38 or Example 39, wherein a level of functionality of at least one of the watch band or the watch body is modified when the watch body is detached from the watch band.

Example 41: The system of any of Examples 38 through 40, wherein the system is configured to determine an orientation of a display of the watch body relative to an eye gaze direction of a user and orient content viewed on the display to the eye gaze direction of the user.

Example 42: The system of any of Examples 38 through 41, further comprising a head-mounted display, wherein the watch body is communicatively coupled to the head-mounted display and the head-mounted display is configured to display at least a portion of the captured wide-angle image.

Example 43: The system of any of Examples 38 through 42, further comprising at least one neuromuscular sensor, wherein the watch body is configured to transmit data captured by the at least one neuromuscular sensor to the head-mounted display and the data captured by the at least one neuromuscular sensor comprises a muscle intention of a user.

Example 44: The system of any of Examples 38 through 43 wherein the head-mounted display is configured to enhance a user interaction with an object within an artificial-reality environment based on the muscle intention.

Example 45: The system of any of Examples 38 through 44, further comprising a head-mounted display, wherein the watch band further comprises a haptic actuator that is configured to provide haptic feedback to a user based on at least one of instructions from the watch body or instructions from the head-mounted display.

Example 46: The system of any of Examples 38 through 45, wherein the coupling mechanism is configured to couple the watch body to the watch band by application of a substantially linear force to the watch body towards the watch band and decouple the watch body from the watch band by at least one of pressing at least one spring loaded button disposed on the watch body or application of a substantially rotational force to the watch body relative to the watch band.

Example 47: The system of any of Examples 38 through 46, wherein the coupling mechanism comprises at least one first spring configured to apply a radially outward force to at least one first pawl, at least one second spring configured to apply a radially outward force to at least one second pawl, a first angled surface disposed on an upper end of the at least one first pawl that is configured to engage a first lock surface of the watch band to secure the watch body to the watch band in a linear direction, and a second angled surface disposed on a side of the at least one second pawl that is configured to engage a second lock surface of the watch band to secure the watch body to the watch band in a rotational direction.

Example 48: The system of any of Examples 38 through 47, wherein the coupling mechanism comprises at least one spring-loaded button disposed on the watch body, at least one lock bar configured to shift in position as a result of pressing the at least one spring-loaded button, and at least one pin configured to retract and to decouple the watch body from the watch band as a result of the shift of the position of the at least one lock bar.

Example 49: The system of any of Examples 38 through 48, wherein the coupling mechanism further comprises a lock bar spring configured to apply a retaining force to the at least one lock bar and an angled surface on the at least one lock bar configured to transfer the retaining force to the at least one pin, wherein the at least one pin is positioned to transfer the retaining force to the watch band with a force component in a direction to retain the watch body against the watch band.

Example 50: The system of any of Examples 38 through 49, wherein the at least one image sensor comprises a first image sensor and a second image sensor the first image sensor is oriented to capture a first wide-angle image in a first direction the second image sensor is oriented to capture a second wide-angle image in a second direction opposite the first direction, and a processor of the system is configured to stitch the first wide-angle image and the second wide-angle image together to create a combined image.

Example 51: The system of any of Examples 38 through 50, wherein the at least one biometric sensor is disposed on a rear face of the watch body and the at least one biometric sensor is configured to be activated in response to the watch body being attached to the watch band.

Example 52: A wearable device, comprising a watch band, a watch body comprising (i) a front face, (ii) a rear face opposite the front face, (iii) a first image sensor in the front face, and (iv) a second image sensor in the rear face, a coupling mechanism configured to detachably couple the watch body to the watch band, one or more processors, and memory storing one or more programs configured to be executed by the one or more processors, the one or more programs including instructions for detecting, at a first time, that the watch body is coupled to the watch band via the coupling mechanism, in response to detecting that the watch body is coupled to the watch band via the coupling mechanism, permitting activation of the first image sensor by a user, detecting, at a second time, that the watch body is not coupled to the watch band via the coupling mechanism, and in response to detecting that the watch body is not coupled to the watch band via the coupling mechanism, activating the second image sensor without user input.

Example 53: The wearable device of Example 52, wherein the one or more programs further include instructions for not permitting activation of the second image sensor by the user in response to detecting that the watch body is coupled to the watch band via the coupling mechanism.

Example 54: The wearable device of Example 52 or Example 53, further comprising at least one proximity sensor coupled to the watch band, the watch body, or the coupling mechanism, the at least one proximity sensor being configured to measure coupling between the watch body and the watch band, wherein detecting that the watch body is coupled to the watch band comprises evaluating coupling data generated by the at least one proximity sensor.

Example 55: The wearable device of any of Examples 52 through 54 further comprising one or more electrical contacts that connect when the watch body is coupled to the watch band, wherein detecting that the watch body is coupled to the watch band comprises detecting an electrical connection between the one or more electrical contacts.

Example 56: The wearable device of any of Examples 52 through 55, wherein the one or more programs further include instructions for receiving test image data from the second image sensor; and determining whether the test image data satisfies an image capture criterion, wherein activating the second image sensor is performed in response to determining that the test image data satisfies the image capture criterion.

Example 57: A non-transitory computer-readable medium encoded with instructions that, when executed by at least one computer processor, performs determining at least one computing task, determining whether to perform the at least one computing task on a watch body or a head-mounted display (HMD), performing the at least one computing task on the watch body or the HMD based on the determination of whether to perform the at least one computing task on the watch body or the HMD, sending results of the at least one computing task to the watch body when the HMD performs the at least one computing task, and sending results of the at least one computing task to the HMD when the watch body performs the at least one computing task.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

The preceding description has been provided to enable others skilled in the art to best utilize various aspects of the example embodiments disclosed herein. This example description is not intended to be exhaustive or to be limited to any precise form disclosed. Many modifications and variations are possible without departing from the spirit and scope of the present disclosure. The embodiments disclosed herein should be considered in all respects illustrative and not restrictive. Reference should be made to the appended claims and their equivalents in determining the scope of the present disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A system comprising:
   at least one physical processor; and
   physical memory comprising computer-executable instructions that, when executed by the physical processor, cause the physical processor to:
      determine whether a watch body is attached to or detached from a watch band;
      deactivate, in response to determining that the watch body is attached to the watch band, an image sensor in a rear face of the watch body; and
      activate, in response to determining that the watch body is detached from the watch band, the image sensor in the rear face of the watch body.

2. The system of claim 1, wherein determining whether the watch body is attached to or detached from the watch band comprises sensing, with a sensor, a proximity of the watch body to the watch band.

3. The system of claim 1, wherein activating the image sensor in the rear face of the watch body is performed as a result of the watch body detaching from the watch band without any further user input.

4. The system of claim 1, wherein the computer-executable instructions further cause the at least one processor to, when the watch body is attached to the watch band, activate a biometric sensor of the watch body.

5. The system of claim 1, wherein the computer-executable instructions further cause the at least one processor to, when the watch body is detached from the watch band, activate a biometric sensor of the watch band.

6. The system of claim 1, wherein the computer-executable instructions further cause the at least one processor to sense, with a neuromuscular sensor of the watch band, a neuromuscular signal of a user wearing the watch band.

7. The system of claim 6, wherein the sensing of the neuromuscular signal is performed when the watch body is detached from the watch band.

8. The system of claim 7, wherein the sensing of the neuromuscular signal comprises determining a muscle intention of the user and capturing an image with the activated image sensor in the rear face of the watch body based on the determined muscle intention.

9. The system of claim 1, wherein the computer-executable instructions further cause the at least one processor to sense, with at least one biometric sensor of the watch band, biometric data from a user wearing the watch band.

10. The system of claim 9, wherein the biometric data comprises at least one of:
a neuromuscular signal of the user;
a heart rate of the user; or
a blood oxygen saturation of the user.

11. The system of claim 9, wherein the sensing of the biometric data is performed when the watch body is detached from the watch band.

12. The system of claim 1, wherein the computer-executable instructions further cause the at least one processor to transfer data from at least one of the watch body or the watch band to another user device.

13. The system of claim 12, wherein the other user device comprises a head-mounted display.

14. The system of claim 13, wherein the data transferred to the head-mounted display comprises image data from the image sensor in the rear face of the watch body.

15. The system of claim 12, wherein the computer-executable instructions further cause the at least one processor to share at least one computing task with another processor of the other user device.

16. A wearable device, comprising:
a watch band;
a watch body comprising:
a first image sensor in a front face of the watch body; and
a second image sensor in a rear face of the watch body opposite the front face;
a coupling mechanism configured to detachably couple the watch body to the watch band;
one or more processors; and
memory storing one or more programs configured to be executed by the one or more processors,
the one or more programs including instructions for:
detecting, at a first time, that the watch body is coupled to the watch band via the coupling mechanism;
based on detecting that the watch body is coupled to the watch band, permitting activation of the first image sensor;
detecting, at a second time, that the watch body is not coupled to the watch band; and
based on detecting that the watch body is not coupled to the watch band, permitting activation of the second image sensor.

17. The wearable device of claim 16, wherein the one or more programs based on response to detecting that the watch body is coupled to the watch band.

18. The wearable device of claim 16, further comprising at least one proximity sensor coupled to at least one of the watch band, the watch body, or the coupling mechanism, the at least one proximity sensor being configured to determine whether the watch body is coupled to the watch band.

19. The wearable device of claim 16, further comprising one or more electrical contacts that connect when the watch body is coupled to the watch band, wherein detecting that the watch body is coupled to the watch band comprises detecting an electrical connection between the one or more electrical contacts.

20. The wearable device of claim 16, wherein the one or more programs further include instructions for:
receiving test image data from the second image sensor;
determining whether the test image data satisfies an image capture criterion; and
activating the second image sensor is performed in response to determining that the test image data satisfies the image capture criterion.

21. A non-transitory computer-readable medium encoded with instructions that, when executed by at least one computer processor, performs:
receiving, via a processor of a wearable device, instructions from another electronic device to perform at least one computing task offloaded from the other electronic device to reduce computing requirements of the other electronic device;
executing, via the processor of the wearable device, the at least one computing task; and
sending results of the at least one computing task from the wearable device to the other electronic device.

* * * * *